（12）United States Patent
Rodenbeck et al.

(10) Patent No.: US 11,458,214 B2
(45) Date of Patent: Oct. 4, 2022

(54) FLUID DELIVERY SYSTEM INCLUDING A DISINFECTANT DEVICE

(71) Applicant: Delta Faucet Company, Indianapolis, IN (US)

(72) Inventors: Robert W. Rodenbeck, Indianapolis, IN (US); John Noble, Carmel, IN (US); Anthony G. Spangler, Indianapolis, IN (US); Joel D. Sawaski, Indianapolis, IN (US); Jayashanger Goundiah Ramasamy, Fishers, IN (US); Patrick B. Jonte, Zionsville, IN (US); Garry R. Marty, Fishers, IN (US)

(73) Assignee: Delta Faucet Company, Indianapolis, IN (US)

( * ) Notice: Subject to any disclaimer, the term of this patent is extended or adjusted under 35 U.S.C. 154(b) by 1131 days.

(21) Appl. No.: 16/064,422

(22) PCT Filed: Dec. 21, 2016

(86) PCT No.: PCT/US2016/068081
§ 371 (c)(1),
(2) Date: Jun. 20, 2018

(87) PCT Pub. No.: WO2017/112795
PCT Pub. Date: Jun. 29, 2017

(65) Prior Publication Data
US 2019/0001006 A1    Jan. 3, 2019

Related U.S. Application Data

(60) Provisional application No. 62/270,395, filed on Dec. 21, 2015.

(51) Int. Cl.
*A61L 2/20* (2006.01)
*A61L 2/00* (2006.01)
(Continued)

(52) U.S. Cl.
CPC ............. *A61L 2/0088* (2013.01); *A61L 2/18* (2013.01); *A61L 2/24* (2013.01); *A61L 2/28* (2013.01);
(Continued)

(58) Field of Classification Search
CPC ..................................................... A61L 2/202
See application file for complete search history.

(56) References Cited

U.S. PATENT DOCUMENTS 2,778,800 A    1/1957  Sheahan
3,653,514 A    4/1972  Holler
(Continued)

FOREIGN PATENT DOCUMENTS

CA    2945136         10/2015
CA    2946465 A1    5/2017
(Continued)

OTHER PUBLICATIONS

US 7,959,787 B2, 06/2011, Field et al. (withdrawn)
(Continued)

*Primary Examiner* — Donald R Spamer
(74) *Attorney, Agent, or Firm* — Bose McKinney & Evans LLP

(57) ABSTRACT

A fluid delivery system illustratively includes a spout, at least one valve in fluid communication with the spout, and a disinfectant device, illustratively an antibacterial device, fluidly coupled to the spout. The faucet is configured to selectively flow water through the disinfectant device in response to a user input to the faucet. In another illustrative embodiment, the fluid delivery system includes an outer housing, a plurality of fluid devices supported by the outer housing, and an ozone generator fluidly coupled to the fluid devices.

32 Claims, 15 Drawing Sheets

(51) Int. Cl.
*A61L 2/24* (2006.01)
*F16K 37/00* (2006.01)
*E03C 1/05* (2006.01)
*A61L 2/18* (2006.01)
*C02F 1/467* (2006.01)
*A61L 2/28* (2006.01)
*C01B 13/11* (2006.01)
*C02F 1/78* (2006.01)

(52) U.S. Cl.
CPC .......... *C01B 13/115* (2013.01); *C02F 1/4672* (2013.01); *E03C 1/055* (2013.01); *F16K 37/00* (2013.01); *A61L 2202/11* (2013.01); *A61L 2202/14* (2013.01); *A61L 2202/17* (2013.01); *C01B 2201/60* (2013.01); *C02F 1/78* (2013.01); *C02F 2201/4614* (2013.01); *C02F 2209/005* (2013.01); *C02F 2209/02* (2013.01); *C02F 2209/04* (2013.01); *C02F 2209/40* (2013.01); *C02F 2303/04* (2013.01); *C02F 2307/06* (2013.01)

(56) References Cited

U.S. PATENT DOCUMENTS

| | | | |
|---|---|---|---|
| 3,805,481 | A | 4/1974 | Armstrong |
| 3,987,617 | A * | 10/1976 | Slob .................. G02F 1/134309 368/242 |
| 4,214,962 | A | 7/1980 | Pincon |
| 4,219,367 | A | 8/1980 | Cary, Jr. |
| 4,352,740 | A | 10/1982 | Grader et al. |
| 4,599,166 | A | 7/1986 | Gesslauer |
| 4,650,573 | A | 3/1987 | Nathanson |
| 4,901,922 | A * | 2/1990 | Kessener .............. G02B 6/0001 239/12 |
| 4,955,535 | A | 9/1990 | Tsutsui et al. |
| 4,971,687 | A | 11/1990 | Anderson |
| 5,103,856 | A | 4/1992 | Fleischmann |
| 5,173,178 | A | 12/1992 | Kawashima et al. |
| 5,199,639 | A | 4/1993 | Kobayashi et al. |
| 5,205,994 | A | 4/1993 | Sawamoto et al. |
| 5,312,624 | A | 5/1994 | Richter et al. |
| 5,354,541 | A | 10/1994 | Sali |
| 5,368,815 | A | 11/1994 | Kasting, Jr. |
| 5,405,631 | A | 4/1995 | Rosenthal |
| 5,578,280 | A | 11/1996 | Kazi et al. |
| 5,635,059 | A | 6/1997 | Johnson |
| 5,670,094 | A | 9/1997 | Sasaki |
| 5,680,658 | A | 10/1997 | Ho |
| 5,728,287 | A | 3/1998 | Hough et al. |
| 5,766,462 | A | 6/1998 | Jones |
| 5,803,139 | A | 9/1998 | Kennedy |
| 5,807,473 | A | 9/1998 | Sadler et al. |
| 5,811,014 | A | 9/1998 | Green |
| 5,824,274 | A | 10/1998 | Long |
| 5,837,142 | A | 11/1998 | Mullerheim |
| 5,843,291 | A | 12/1998 | Eki et al. |
| 5,843,307 | A | 12/1998 | Faivre et al. |
| 5,853,562 | A | 12/1998 | Eki et al. |
| 5,858,201 | A | 1/1999 | Otsuka et al. |
| 5,858,215 | A | 1/1999 | Burchard et al. |
| 5,858,435 | A | 1/1999 | Gallo |
| 5,879,732 | A | 3/1999 | Caracciolo |
| 5,900,143 | A | 5/1999 | Dalton et al. |
| 5,911,870 | A | 6/1999 | Hough |
| 5,932,171 | A | 8/1999 | Malchesky |
| 5,939,030 | A | 8/1999 | Moxley |
| 5,945,068 | A | 8/1999 | Ferone |
| 5,948,374 | A | 9/1999 | Kuzumoto |
| 5,961,920 | A | 10/1999 | Soremark |
| 5,962,383 | A | 10/1999 | Doyel |
| 5,985,108 | A | 11/1999 | Arai |
| 5,985,223 | A | 11/1999 | Saxena |
| 5,989,407 | A | 11/1999 | Andrews |
| 5,992,431 | A | 11/1999 | Weber |
| 6,017,862 | A | 1/2000 | Doyel |
| 6,019,950 | A | 2/2000 | Lai |
| 6,024,882 | A | 2/2000 | McNeilly et al. |
| 6,030,586 | A | 2/2000 | Kuan |
| 6,035,871 | A | 3/2000 | Oh |
| 6,039,884 | A | 3/2000 | Burris |
| 6,045,588 | A | 4/2000 | Estes |
| 6,058,940 | A | 5/2000 | Lane |
| 6,060,439 | A | 5/2000 | Doyel |
| 6,066,257 | A | 5/2000 | Venkatesh |
| 6,086,833 | A | 7/2000 | Conners |
| 6,096,219 | A | 8/2000 | Green |
| 6,096,221 | A | 8/2000 | Kerchouche |
| 6,106,731 | A | 8/2000 | Hayes |
| 6,110,292 | A | 8/2000 | Jewett |
| 6,123,759 | A | 9/2000 | Mise |
| 6,132,629 | A | 10/2000 | Boley |
| 6,135,146 | A * | 10/2000 | Koganezawa .......... A61L 2/202 137/551 |
| 6,139,710 | A | 10/2000 | Powell |
| 6,153,105 | A | 11/2000 | Tadlock |
| 6,153,151 | A | 11/2000 | Moxley |
| 6,167,709 | B1 | 1/2001 | Caracciolo |
| 6,171,469 | B1 | 1/2001 | Hough et al. |
| 6,178,973 | B1 | 1/2001 | Franca |
| 6,180,014 | B1 | 1/2001 | Salama |
| 6,197,268 | B1 | 3/2001 | Hwang |
| 6,197,321 | B1 | 3/2001 | Richter et al. |
| 6,197,573 | B1 | 3/2001 | Suryanarayan |
| 6,210,801 | B1 | 4/2001 | Luo |
| 6,217,833 | B1 | 4/2001 | Kolu |
| 6,221,487 | B1 | 4/2001 | Luo |
| 6,231,769 | B1 | 5/2001 | Pean |
| 6,235,392 | B1 | 5/2001 | Luo |
| 6,245,229 | B1 | 6/2001 | Kool et al. |
| 6,251,172 | B1 | 6/2001 | Conrad |
| 6,267,125 | B1 | 7/2001 | Bergman |
| 6,267,878 | B1 | 7/2001 | Kerchouche |
| 6,273,108 | B1 | 8/2001 | Bergman |
| 6,280,696 | B1 | 8/2001 | Hsu |
| 6,299,668 | B1 | 10/2001 | Penth |
| 6,299,778 | B1 | 10/2001 | Penth |
| 6,300,255 | B1 | 10/2001 | Venkataranan |
| 6,306,334 | B1 | 10/2001 | Luo |
| 6,309,545 | B1 | 10/2001 | Penth |
| 6,319,390 | B1 | 11/2001 | Kono |
| 6,328,044 | B1 | 12/2001 | Crisinel |
| 6,331,354 | B1 | 12/2001 | Sealey |
| 6,340,379 | B1 | 1/2002 | Penth |
| 6,348,155 | B1 | 2/2002 | Conway |
| 6,348,227 | B1 | 2/2002 | Caracciolo |
| 6,357,727 | B1 | 3/2002 | Cho |
| 6,363,656 | B1 | 4/2002 | Byun |
| 6,365,026 | B1 | 4/2002 | Andrews |
| 6,368,503 | B1 | 4/2002 | Williamson et al. |
| 6,375,717 | B1 | 4/2002 | Peteln |
| 6,375,721 | B1 | 4/2002 | Holter |
| 6,379,633 | B1 | 4/2002 | Garlick |
| 6,379,746 | B1 | 4/2002 | Birch |
| 6,380,119 | B1 | 4/2002 | Grosch |
| 6,386,751 | B1 | 5/2002 | Wootan et al. |
| 6,387,348 | B1 | 5/2002 | Ferrell |
| 6,391,191 | B2 | 5/2002 | Conrad |
| 6,399,492 | B1 | 6/2002 | Andreas |
| 6,405,491 | B1 | 6/2002 | Gallant |
| 6,419,831 | B2 | 7/2002 | Wang |
| 6,426,005 | B1 | 7/2002 | Larsson |
| 6,428,710 | B1 | 8/2002 | Kempen et al. |
| 6,431,189 | B1 | 8/2002 | Deibert |
| 6,436,445 | B1 | 8/2002 | Hei |
| 6,436,826 | B1 | 8/2002 | Pyo |
| 6,440,523 | B1 | 8/2002 | Sealey |
| 6,440,547 | B1 | 8/2002 | Luo |
| 6,444,314 | B1 | 9/2002 | Luo |
| 6,447,633 | B1 | 9/2002 | Peace |
| 6,451,066 | B2 | 9/2002 | Estes |
| 6,453,584 | B1 | 9/2002 | Buckner |
| 6,455,017 | B1 | 9/2002 | Kasting, Jr. |

(56) References Cited

U.S. PATENT DOCUMENTS

| | | |
|---|---|---|
| 6,458,257 B1 | 10/2002 | Andrews |
| 6,461,487 B1 | 10/2002 | Andrews |
| 6,471,727 B2 | 10/2002 | Luo |
| 6,482,370 B2 | 11/2002 | Holsclaw et al. |
| 6,485,769 B2 | 11/2002 | Audy |
| 6,488,835 B1 | 12/2002 | Powell |
| 6,489,281 B1 | 12/2002 | Smith |
| 6,491,788 B2 | 12/2002 | Sealey |
| 6,491,879 B2 | 12/2002 | Conrad |
| 6,492,284 B2 | 12/2002 | Peace |
| 6,494,228 B2 | 12/2002 | Guillaume |
| 6,497,768 B2 | 12/2002 | Bergman |
| 6,506,309 B1 | 1/2003 | Daniels et al. |
| 6,506,351 B1 | 1/2003 | Jain |
| 6,511,914 B2 | 1/2003 | Wirth |
| 6,511,930 B1 | 1/2003 | Luo |
| 6,514,613 B2 | 2/2003 | Luo |
| 6,516,536 B2 | 2/2003 | Ryden |
| 6,521,194 B2 | 2/2003 | Yeh |
| 6,523,193 B2 | 2/2003 | Saraya |
| 6,528,163 B2 | 3/2003 | Sealey |
| 6,537,494 B2 | 3/2003 | Garlick |
| 6,548,411 B2 | 4/2003 | Wirth |
| 6,551,182 B2 | 4/2003 | Caracciolo |
| 6,551,409 B1 | 4/2003 | DeGendt et al. |
| 6,551,490 B2 | 4/2003 | Andrews et al. |
| 6,555,053 B1 | 4/2003 | Aoyagi |
| 6,561,134 B1 | 5/2003 | Mikami |
| 6,562,386 B2 | 5/2003 | Ruan |
| 6,565,927 B1 | 5/2003 | Drzal |
| 6,576,096 B1 | 6/2003 | Andrews |
| 6,579,810 B2 | 6/2003 | Chang |
| 6,581,215 B1 | 6/2003 | Tai |
| 6,582,525 B2 | 6/2003 | Bergman |
| 6,585,867 B1 | 7/2003 | Asano |
| 6,591,638 B2 | 7/2003 | Estes |
| 6,591,845 B1 | 7/2003 | Bergman |
| 6,592,677 B1 | 7/2003 | Tomimori |
| 6,595,440 B2 | 7/2003 | Moriarty et al. |
| 6,596,033 B1 | 7/2003 | Luo |
| 6,601,594 B2 | 8/2003 | Bergman |
| 6,605,350 B1 | 8/2003 | Sealey |
| 6,609,863 B1 | 8/2003 | Morioka et al. |
| 6,615,854 B1 | 9/2003 | Hongo |
| 6,626,212 B2 | 9/2003 | Morioka et al. |
| 6,632,292 B1 | 10/2003 | Aegerter |
| 6,637,049 B2 | 10/2003 | Gallant |
| 6,637,438 B1 | 10/2003 | Lane |
| 6,638,364 B2 | 10/2003 | Harkins et al. |
| 6,645,255 B2 | 11/2003 | Sanduja et al. |
| 6,645,569 B2 | 11/2003 | Cramer et al. |
| 6,645,874 B1 | 11/2003 | Torek |
| 6,649,052 B2 | 11/2003 | Lee |
| 6,651,134 B1 | 11/2003 | Phelan |
| 6,652,816 B2 | 11/2003 | Hwang |
| 6,664,095 B1 | 12/2003 | Suryanarayan |
| 6,671,563 B1 | 12/2003 | Engelson et al. |
| 6,673,248 B2 | 1/2004 | Chowdbury |
| 6,680,253 B2 | 1/2004 | Wirth |
| 6,681,417 B2 | 1/2004 | Brunelle |
| 6,691,536 B2 | 2/2004 | Severns et al. |
| 6,692,613 B2 | 2/2004 | Peace |
| 6,692,827 B2 | 2/2004 | Luo |
| 6,696,228 B2 | 2/2004 | Muraoka |
| 6,699,330 B1 | 3/2004 | Muraoka |
| 6,701,941 B1 | 3/2004 | Bergman |
| 6,702,941 B1 | 3/2004 | Haq |
| 6,702,949 B2 | 3/2004 | Wood |
| 6,706,237 B2 | 3/2004 | Luo |
| 6,706,876 B2 | 3/2004 | Luo |
| 6,709,599 B1 | 3/2004 | Rosenberger |
| 6,710,002 B2 | 3/2004 | Grosch |
| 6,712,951 B2 | 3/2004 | Andrews |
| 6,723,233 B1 | 4/2004 | Barnes |
| 6,726,749 B2 | 4/2004 | Peteln |
| 6,727,818 B1 | 4/2004 | Wildman et al. |
| 6,730,176 B2 | 5/2004 | Kuyel |
| 6,731,989 B2 | 5/2004 | Engleson et al. |
| 6,738,996 B1 | 5/2004 | Malek et al. |
| 6,743,301 B2 | 6/2004 | Matsuno |
| 6,746,580 B2 | 6/2004 | Andrews |
| 6,757,921 B2 | 7/2004 | Esche |
| 6,766,670 B2 | 7/2004 | Estes |
| 6,766,963 B2 | 7/2004 | Hansen |
| 6,769,568 B2 | 8/2004 | Bonini et al. |
| 6,770,168 B1 | 8/2004 | Stigsson |
| 6,771,916 B2 | 8/2004 | Hoffman |
| 6,774,056 B2 | 8/2004 | Kuntz |
| 6,786,221 B2 | 9/2004 | Lane |
| 6,790,429 B2 | 9/2004 | Ciampi |
| 6,794,291 B2 | 9/2004 | Peace |
| 6,797,156 B2 | 9/2004 | Chau |
| 6,800,206 B2 | 10/2004 | Robinson |
| 6,802,984 B1 | 10/2004 | Perkins |
| 6,803,066 B2 | 10/2004 | Traeder et al. |
| 6,806,194 B2 | 10/2004 | Wirth |
| 6,808,637 B2 | 10/2004 | Cho |
| 6,810,548 B2 | 11/2004 | Yoshioka |
| 6,811,811 B2 | 11/2004 | Gerald France et al. |
| 6,814,876 B1 | 11/2004 | Neal |
| 6,817,370 B2 | 11/2004 | Bergman |
| 6,821,443 B2 | 11/2004 | Kim |
| 6,837,252 B2 | 1/2005 | Bergman |
| 6,837,944 B2 | 1/2005 | Kashkoush |
| 6,838,376 B2 | 1/2005 | Matsuse |
| 6,841,075 B2 | 1/2005 | Penth |
| 6,843,835 B2 | 1/2005 | Fornai |
| 6,844,742 B2 | 1/2005 | Centanni |
| 6,851,873 B2 | 2/2005 | Muraoka |
| 6,858,571 B2 | 2/2005 | Pham et al. |
| 6,860,277 B2 | 3/2005 | Lee |
| 6,861,023 B2 | 3/2005 | Sealey |
| 6,861,356 B2 | 3/2005 | Matsuse |
| 6,863,933 B2 | 3/2005 | Cramer et al. |
| 6,866,806 B2 | 3/2005 | Andrews |
| 6,869,487 B1 | 3/2005 | Bergman |
| 6,869,540 B2 | 3/2005 | Robinson |
| 6,872,366 B2 | 3/2005 | Thomas |
| 6,872,444 B2 | 3/2005 | McDonald et al. |
| 6,874,535 B2 | 4/2005 | Parsons et al. |
| 6,876,303 B2 | 4/2005 | Reeder et al. |
| 6,881,243 B1 | 4/2005 | Khitrik |
| 6,883,563 B2 | 4/2005 | Smith |
| 6,893,469 B1 | 5/2005 | Van Hauwermeiren et al. |
| 6,897,661 B2 | 5/2005 | Allen |
| 6,897,832 B2 | 5/2005 | Essig |
| 6,898,951 B2 | 5/2005 | Severns et al. |
| 6,904,920 B2 | 6/2005 | Bexten |
| 6,908,976 B2 | 6/2005 | Sanduja et al. |
| 6,913,028 B2 | 7/2005 | Morioka et al. |
| 6,915,170 B2 | 7/2005 | Engleson et al. |
| 6,919,032 B2 | 7/2005 | Mulgrew |
| 6,921,476 B2 | 7/2005 | Abe |
| 6,927,176 B2 | 8/2005 | Verhaverbeke |
| 6,929,903 B2 | 8/2005 | Itoh |
| 6,930,046 B2 | 8/2005 | Hanson |
| 6,932,903 B2 | 8/2005 | Chang |
| 6,932,907 B2 | 8/2005 | Haq |
| 6,933,733 B2 | 8/2005 | Korenev |
| 6,946,080 B2 | 9/2005 | Perkins |
| 6,946,852 B2 | 9/2005 | Centanni |
| 6,949,145 B2 | 9/2005 | Banerjee |
| 6,953,525 B2 | 10/2005 | LeCraw |
| 6,964,739 B2 | 11/2005 | Boyd |
| 6,969,682 B2 | 11/2005 | Hanson |
| 6,970,574 B1 | 11/2005 | Johnson |
| 6,974,562 B2 | 12/2005 | Ciampi et al. |
| 6,982,006 B1 | 1/2006 | Boyers |
| 6,982,241 B2 | 1/2006 | Smith |
| 6,983,756 B2 | 1/2006 | Matsuno |
| 6,984,295 B2 | 1/2006 | Shiue |
| 6,988,568 B2 | 1/2006 | Buckner |
| 6,990,868 B2 | 1/2006 | Hardcastle |
| 6,991,820 B2 | 1/2006 | Ming et al. |

(56) References Cited

U.S. PATENT DOCUMENTS

| | | |
|---|---|---|
| 7,001,086 B2 | 2/2006 | Itoh |
| 7,008,523 B2 | 3/2006 | Herrington |
| 7,008,535 B1 | 3/2006 | Spears |
| 7,008,592 B2 | 3/2006 | Sias |
| 7,013,504 B2 | 3/2006 | Brunelle |
| 7,014,684 B2 | 3/2006 | Dietrich |
| 7,015,816 B2 | 3/2006 | Wildman et al. |
| 7,018,481 B2 | 3/2006 | Hayasaki |
| 7,029,577 B2 | 4/2006 | Cummins |
| 7,029,637 B2 | 4/2006 | Hogarth |
| 7,037,853 B2 | 5/2006 | Hongo |
| 7,041,226 B2 | 5/2006 | Vaideeswaran |
| 7,041,270 B2 | 5/2006 | Hammel |
| 7,043,855 B2 | 5/2006 | Heilman |
| 7,047,663 B2 | 5/2006 | Zhang |
| 7,059,065 B2 | 6/2006 | Gerlach |
| 7,067,057 B2 | 6/2006 | Rosenberger |
| 7,067,444 B2 | 6/2006 | Luo |
| 7,070,125 B2 | 7/2006 | Williams et al. |
| 7,070,769 B2 | 7/2006 | Ascione et al. |
| 7,071,175 B1 | 7/2006 | Linschoten |
| 7,074,751 B2 | 7/2006 | Singh et al. |
| 7,081,095 B2 | 7/2006 | Lynn et al. |
| 7,083,510 B2 | 8/2006 | Caracciolo |
| 7,083,704 B2 | 8/2006 | Sealey |
| 7,086,407 B2 | 8/2006 | Lynn |
| 7,087,123 B2 | 8/2006 | Lynn |
| 7,087,124 B2 | 8/2006 | Lynn |
| 7,087,504 B2 | 8/2006 | Nakajima |
| 7,087,805 B2 | 8/2006 | Centanni |
| 7,089,763 B2 | 8/2006 | Forsberg |
| 7,090,744 B2 | 8/2006 | Sealey |
| 7,093,734 B2 | 8/2006 | Garwood |
| 7,094,522 B2 | 8/2006 | Itoh |
| 7,096,072 B2 | 8/2006 | Engleson et al. |
| 7,103,419 B2 | 9/2006 | Engleson et al. |
| 7,105,133 B2 | 9/2006 | Kim |
| 7,107,106 B2 | 9/2006 | Engleson et al. |
| 7,112,621 B2 | 9/2006 | Rohrbaugh et al. |
| 7,117,041 B2 | 10/2006 | Engleson et al. |
| 7,118,672 B2 | 10/2006 | Husain |
| 7,122,484 B2 | 10/2006 | Perng |
| 7,128,278 B2 | 10/2006 | Achambeau |
| 7,135,108 B1 | 11/2006 | Barnes |
| 7,146,749 B2 | 12/2006 | Barron |
| 7,147,692 B2 | 12/2006 | Fornai |
| 7,153,370 B2 | 12/2006 | Lee |
| 7,160,441 B2 | 1/2007 | Gannon |
| 7,160,472 B2 | 1/2007 | Van Vliet |
| 7,163,588 B2 | 1/2007 | Bergman |
| 7,166,219 B2 | 1/2007 | Kohler |
| 7,169,295 B2 | 1/2007 | Husain |
| 7,171,277 B2 | 1/2007 | Engleson et al. |
| 7,174,601 B1 | 2/2007 | Palmer |
| 7,179,746 B2 | 2/2007 | Ohmi |
| 7,186,375 B2 | 3/2007 | Centanni |
| 7,188,632 B2 | 3/2007 | Lynn |
| 7,192,553 B2 | 3/2007 | Crowe |
| 7,199,516 B2 | 4/2007 | Seo |
| 7,205,018 B2 | 4/2007 | Sherwood et al. |
| 7,211,185 B2 | 5/2007 | Powell |
| 7,211,187 B2 | 5/2007 | Lumbert |
| 7,214,356 B2 | 5/2007 | Hsieh et al. |
| 7,217,325 B2 | 5/2007 | Hanson |
| 7,217,952 B2 | 5/2007 | Nakajima |
| 7,223,822 B2 | 5/2007 | Abhari et al. |
| 7,242,306 B2 | 7/2007 | Wildman et al. |
| 7,244,354 B2 | 7/2007 | Burris |
| 7,255,332 B2 | 8/2007 | Osborn |
| 7,255,831 B2 | 8/2007 | Wei |
| 7,258,798 B2 | 8/2007 | LeCraw |
| 7,258,802 B2 | 8/2007 | Miks |
| 7,264,680 B2 | 9/2007 | Gebhart |
| 7,271,728 B2 | 9/2007 | Taylor et al. |
| 7,272,947 B2 | 9/2007 | Anderson |
| 7,273,562 B2 | 9/2007 | Van Leeuwen |
| 7,273,716 B2 | 9/2007 | McDermott |
| 7,275,400 B2 | 10/2007 | Severns et al. |
| 7,275,551 B2 | 10/2007 | Kanaya |
| 7,278,434 B2 | 10/2007 | Huang |
| 7,279,451 B2 | 10/2007 | Singh et al. |
| 7,285,256 B2 | 10/2007 | Wan |
| 7,293,658 B2 | 11/2007 | Cummins |
| 7,294,278 B2 | 11/2007 | Spears |
| 7,294,681 B2 | 11/2007 | Jiang et al. |
| 7,297,225 B2 | 11/2007 | Thomas |
| 7,300,571 B2 | 11/2007 | Cote |
| 7,303,676 B2 | 12/2007 | Husain |
| 7,303,677 B2 | 12/2007 | Cote |
| 7,307,188 B2 | 12/2007 | Wytcherley |
| 7,314,600 B2 | 1/2008 | Matsuzaki |
| 7,320,756 B2 | 1/2008 | Mukhopadhyay |
| 7,322,535 B2 | 1/2008 | Erdely |
| 7,332,095 B2 | 2/2008 | Johnston |
| 7,341,984 B2 | 3/2008 | Wilson et al. |
| 7,344,640 B2 | 3/2008 | Gannon |
| 7,354,933 B2 | 4/2008 | Patek |
| 7,371,637 B2 | 5/2008 | Ramkumar |
| 7,373,787 B2 | 5/2008 | Forsberg |
| 7,378,084 B2 | 5/2008 | Dueva-Koganov |
| 7,378,355 B2 | 5/2008 | Bergman |
| 7,381,244 B2 | 6/2008 | Tyndall |
| 7,381,338 B2 | 6/2008 | Van Leeuwen |
| 7,382,332 B2 | 6/2008 | Essig |
| 7,387,719 B2 | 6/2008 | Carson |
| 7,387,736 B2 | 6/2008 | Phillips |
| 7,388,649 B2 | 6/2008 | Kobayashi et al. |
| 7,390,365 B2 | 6/2008 | Itoh |
| 7,392,600 B2 | 7/2008 | Gerlach |
| 7,399,713 B2 | 7/2008 | Aegerter |
| 7,402,253 B2 | 7/2008 | Van Leeuwen |
| 7,404,863 B2 | 7/2008 | Bergman |
| 7,407,592 B2 | 8/2008 | Van Leeuwen |
| 7,407,633 B2 | 8/2008 | Potember |
| 7,408,470 B2 | 8/2008 | Wildman et al. |
| 7,413,650 B2 | 8/2008 | Lumbert |
| 7,415,781 B2 | 8/2008 | Barron |
| 7,416,581 B2 | 8/2008 | Raetz |
| 7,416,611 B2 | 8/2008 | Bergman |
| 7,416,660 B2 | 8/2008 | Van Leeuwen |
| 7,422,684 B1 | 9/2008 | Davis |
| 7,423,728 B2 | 9/2008 | Matsunaga |
| 7,429,537 B2 | 9/2008 | Aegerter |
| 7,438,392 B2 | 10/2008 | Vaideeswaran |
| 7,442,352 B2 | 10/2008 | Lu |
| 7,443,302 B2 | 10/2008 | Reeder et al. |
| 7,443,305 B2 | 10/2008 | Verdiramo |
| 7,446,121 B2 | 11/2008 | Pfefferkorn |
| 7,449,127 B2 | 11/2008 | Verhaverbeke |
| 7,450,024 B2 | 11/2008 | Wildman et al. |
| 7,456,113 B2 | 11/2008 | Rayandayan |
| 7,458,520 B2 | 12/2008 | Belz et al. |
| 7,459,075 B2 | 12/2008 | Burns |
| 7,462,608 B2 | 12/2008 | Chen et al. |
| 7,464,418 B2 | 12/2008 | Seggio et al. |
| 7,469,883 B2 | 12/2008 | Verhaverbeke |
| 7,470,172 B2 | 12/2008 | Caracciolo |
| 7,479,215 B2 | 1/2009 | Carson |
| 7,479,477 B2 | 1/2009 | Wilson et al. |
| 7,481,935 B2 | 1/2009 | Olivier |
| 7,482,207 B2 | 1/2009 | Brown et al. |
| 7,483,756 B2 | 1/2009 | Engleson et al. |
| 7,488,409 B1 | 2/2009 | Carson |
| 7,488,419 B1 | 2/2009 | Wang et al. |
| 7,493,906 B2 | 2/2009 | Mulgrew |
| 7,494,074 B2 | 2/2009 | Berstead |
| 7,494,549 B2 | 2/2009 | Eitoku |
| 7,494,962 B2 | 2/2009 | Kin et al. |
| 7,501,103 B2 | 3/2009 | Oeste |
| 7,501,550 B2 | 3/2009 | Klaptchuk |
| 7,503,127 B2 | 3/2009 | DuVal |
| 7,503,134 B2 | 3/2009 | Buckner |
| 7,504,267 B2 | 3/2009 | Liang |
| 7,514,008 B2 | 4/2009 | Burnes |

(56) References Cited

U.S. PATENT DOCUMENTS

| | | | |
|---|---|---|---|
| 7,517,445 | B2 | 4/2009 | Carson |
| 7,524,466 | B2 | 4/2009 | Long |
| 7,524,618 | B2 | 4/2009 | Ito |
| 7,524,805 | B2 | 4/2009 | Singh et al. |
| 7,524,910 | B2 | 4/2009 | Jiang et al. |
| 7,531,463 | B2 | 5/2009 | Koos |
| 7,531,710 | B2 | 5/2009 | Carson |
| 7,531,730 | B2 | 5/2009 | Everly |
| 7,534,288 | B2 | 5/2009 | Bromberg |
| 7,534,304 | B2 | 5/2009 | Conrad |
| 7,534,366 | B2 | 5/2009 | Singh et al. |
| 7,534,400 | B2 | 5/2009 | Hsieh et al. |
| 7,537,023 | B2 | 5/2009 | Marty et al. |
| 7,537,640 | B2 | 5/2009 | Wan |
| 7,541,402 | B2 | 6/2009 | Abhari et al. |
| 7,542,586 | B2 | 6/2009 | Johnson |
| 7,550,528 | B2 | 6/2009 | Abhari et al. |
| 7,559,973 | B2 | 7/2009 | Wan |
| 7,566,387 | B2 | 7/2009 | Nam |
| 7,569,232 | B2 | 8/2009 | Man et al. |
| 7,581,264 | B2 | 9/2009 | Mangiardi |
| 7,581,549 | B2 | 9/2009 | Johnson |
| 7,582,539 | B2 | 9/2009 | Lee |
| 7,585,406 | B2 | 9/2009 | Khadzhiev |
| 7,589,145 | B2 | 9/2009 | Brant et al. |
| 7,604,735 | B1 | 10/2009 | Barnes |
| 7,605,117 | B2 | 10/2009 | Wilson et al. |
| 7,607,443 | B2 | 10/2009 | Barnhill |
| 7,610,115 | B2 | 10/2009 | Rob |
| 7,611,620 | B2 | 11/2009 | Carson |
| 7,612,735 | B2 | 11/2009 | Essig |
| 7,622,435 | B2 | 11/2009 | Wilson et al. |
| 7,628,924 | B2 | 12/2009 | Jack |
| 7,628,967 | B2 | 12/2009 | Johnson |
| 7,629,306 | B2 | 12/2009 | Shankland et al. |
| 7,631,372 | B2 | 12/2009 | Marty et al. |
| 7,632,475 | B2 | 12/2009 | Suchak et al. |
| 7,638,067 | B2 | 12/2009 | Hilgren |
| 7,638,070 | B2 | 12/2009 | Johnson |
| 7,640,766 | B2 | 1/2010 | Shelton |
| 7,644,523 | B2 | 1/2010 | Buckner |
| 7,645,829 | B2 | 1/2010 | Tse et al. |
| 7,648,584 | B2 | 1/2010 | Freer |
| 7,649,015 | B2 | 1/2010 | Arimili et al. |
| 7,654,728 | B2 | 2/2010 | Wood |
| 7,655,610 | B2 | 2/2010 | Singh et al. |
| 7,662,293 | B2 | 2/2010 | Brolin et al. |
| 7,669,608 | B2 | 3/2010 | Hayasaki |
| 7,674,339 | B2 | 3/2010 | Silberberg et al. |
| 7,679,879 | B2 | 3/2010 | Furuhashi |
| 7,686,962 | B2 | 3/2010 | Burns |
| 7,690,395 | B2 | 4/2010 | Jonte et al. |
| 7,691,251 | B2 | 4/2010 | Carson |
| 7,696,141 | B2 | 4/2010 | Freer |
| 7,699,985 | B2 | 4/2010 | Cote |
| 7,699,988 | B2 | 4/2010 | McGuire |
| 7,699,994 | B2 | 4/2010 | McGuire |
| 7,700,049 | B2 | 4/2010 | Clark |
| 7,700,707 | B2 | 4/2010 | Abhari et al. |
| 7,702,970 | B2 | 4/2010 | Ha et al. |
| 7,708,958 | B2 | 5/2010 | Namespetra |
| 7,726,906 | B2 | 6/2010 | Essig |
| 7,728,513 | B2 | 6/2010 | Seo |
| 7,731,800 | B2 | 6/2010 | Puri |
| 7,733,459 | B2 | 6/2010 | Dierichs |
| 7,736,599 | B2 | 6/2010 | Chiu |
| 7,736,600 | B2 | 6/2010 | Clark |
| 7,737,097 | B2 | 6/2010 | Freer |
| 7,737,101 | B2 | 6/2010 | Thonhauser et al. |
| 7,740,686 | B2 | 6/2010 | Metteer |
| 7,740,815 | B2 | 6/2010 | Smith |
| 7,755,494 | B2 | 7/2010 | Melker et al. |
| 7,758,742 | B2 | 7/2010 | Powell |
| 7,766,043 | B2 | 8/2010 | Thomas et al. |
| 7,766,995 | B2 | 8/2010 | Suchak et al. |
| 7,767,095 | B2 | 8/2010 | Phillips |
| 7,767,168 | B2 | 8/2010 | Namespetra |
| 7,767,638 | B2 | 8/2010 | Singh et al. |
| 7,768,146 | B2 | 8/2010 | Balzano |
| 7,770,782 | B2 | 8/2010 | Sahud |
| 7,771,737 | B2 | 8/2010 | Man et al. |
| 7,780,856 | B2 | 8/2010 | Liou |
| 7,780,858 | B2 | 8/2010 | Miks |
| 7,781,963 | B2 | 8/2010 | Yoshida et al. |
| 7,782,214 | B1 | 8/2010 | Lynn |
| 7,783,383 | B2 | 8/2010 | Eliuk |
| 7,785,470 | B2 | 8/2010 | McGuire |
| 7,790,127 | B1 | 9/2010 | Lee |
| 7,790,477 | B2 | 9/2010 | Liang |
| 7,794,770 | B2 | 9/2010 | Sherwood et al. |
| 7,799,141 | B2 | 9/2010 | Korolik |
| 7,799,363 | B2 | 9/2010 | Sherwood et al. |
| 7,806,584 | B2 | 10/2010 | Wood |
| 7,806,988 | B2 | 10/2010 | Rana |
| 7,812,730 | B2 | 10/2010 | Wildman et al. |
| 7,817,046 | B2 | 10/2010 | Coveley et al. |
| 7,819,947 | B2 | 10/2010 | Weist |
| 7,821,616 | B2 | 10/2010 | Ito |
| 7,824,505 | B2 | 11/2010 | Rana |
| 7,825,081 | B2 | 11/2010 | Singh et al. |
| 7,829,144 | B2 | 11/2010 | Matsuse |
| 7,836,543 | B2 | 11/2010 | Field et al. |
| 7,837,882 | B2 | 11/2010 | Van Vliet |
| 7,841,737 | B2 | 11/2010 | Mangiardi |
| 7,842,326 | B2 | 11/2010 | Sherwood et al. |
| 7,846,263 | B1 | 12/2010 | Marcantel |
| 7,850,098 | B2 | 12/2010 | Vogel et al. |
| 7,857,995 | B2 | 12/2010 | Johnson |
| 7,860,583 | B2 | 12/2010 | Condurso et al. |
| 7,862,662 | B2 | 1/2011 | Freer |
| 7,863,233 | B2 | 1/2011 | Thonhauser |
| 7,875,173 | B1 | 1/2011 | Barnes |
| 7,875,179 | B2 | 1/2011 | Suzuki |
| 7,880,860 | B2 | 2/2011 | Jansen |
| 7,886,557 | B2 | 2/2011 | Anderson |
| 7,887,679 | B2 | 2/2011 | Kitaori |
| 7,891,046 | B2 | 2/2011 | Field et al. |
| 7,892,326 | B2 | 2/2011 | Raetz |
| 7,896,947 | B2 | 3/2011 | Takahashi |
| 7,897,192 | B2 | 3/2011 | Sherwood et al. |
| 7,898,407 | B2 | 3/2011 | Hufton et al. |
| 7,901,276 | B2 | 3/2011 | McNaughton |
| 7,906,086 | B2 | 3/2011 | Comrie |
| 7,906,160 | B2 | 3/2011 | Sherwood et al. |
| 7,909,269 | B2 | 3/2011 | Erickson et al. |
| 7,914,365 | B2 | 3/2011 | McNaughton et al. |
| 7,922,668 | B2 | 4/2011 | Rimdzius |
| 7,922,824 | B2 | 4/2011 | Minsek et al. |
| 7,922,890 | B2 | 4/2011 | Sanchez et al. |
| 7,927,428 | B2 | 4/2011 | Shibazaki |
| 7,930,066 | B2 | 4/2011 | Eliuk |
| 7,931,813 | B2 | 4/2011 | Asokan et al. |
| 7,931,859 | B2 | 4/2011 | Eliuk |
| 7,932,425 | B2 | 4/2011 | Blessing |
| 7,932,618 | B2 | 4/2011 | Baarman et al. |
| 7,935,565 | B2 | 5/2011 | Brown et al. |
| 7,935,665 | B2 | 5/2011 | Leon et al. |
| 7,938,911 | B2 | 5/2011 | Zapilko |
| 7,943,040 | B2 | 5/2011 | Taylor |
| 7,943,087 | B2 | 5/2011 | McGuire |
| 7,946,299 | B2 | 5/2011 | Franklin |
| 7,946,304 | B2 | 5/2011 | Kim |
| 7,947,104 | B2 | 5/2011 | Burnham |
| 7,947,108 | B2 | 5/2011 | Wan |
| 7,952,484 | B2 | 5/2011 | Lynn |
| 7,955,631 | B2 | 6/2011 | Turatti |
| 7,956,480 | B2 | 6/2011 | Onodera et al. |
| 7,956,481 | B2 | 6/2011 | Baarman et al. |
| 7,959,943 | B2 | 6/2011 | Hissong et al. |
| 7,964,068 | B2 | 6/2011 | Kitaori |
| 7,964,166 | B2 | 6/2011 | Suchak |
| 7,967,800 | B2 | 6/2011 | Chewins |
| 7,968,006 | B2 | 6/2011 | Johnson |
| 7,972,441 | B2 | 7/2011 | Yokota |

(56) References Cited

U.S. PATENT DOCUMENTS

| | | |
|---|---|---|
| 7,976,873 B2 | 7/2011 | Myntti et al. |
| 7,976,875 B2 | 7/2011 | Myntti |
| 7,978,083 B2 | 7/2011 | Melker et al. |
| 7,981,297 B2 | 7/2011 | Sauvignet et al. |
| 7,985,188 B2 | 7/2011 | Felts et al. |
| 7,985,379 B2 | 7/2011 | Chiu |
| 7,986,395 B2 | 7/2011 | Chang et al. |
| 7,993,601 B2 | 8/2011 | Weiss |
| 7,993,675 B2 | 8/2011 | Oliver et al. |
| 8,002,614 B2 | 8/2011 | McNaughton et al. |
| 8,004,183 B2 | 8/2011 | Seo |
| 8,007,654 B2 | 8/2011 | Field et al. |
| 8,007,666 B1 | 8/2011 | Davis |
| 8,008,860 B2 | 8/2011 | Yoshida et al. |
| 8,012,339 B2 | 9/2011 | Field |
| 8,012,340 B2 | 9/2011 | Field et al. |
| 8,012,521 B2 | 9/2011 | Garwood |
| 8,012,758 B2 | 9/2011 | Enzien |
| 8,016,996 B2 | 9/2011 | Field et al. |
| 8,017,040 B2 | 9/2011 | Johnson |
| 8,017,041 B2 | 9/2011 | Johnson |
| 8,017,813 B2 | 9/2011 | Kin et al. |
| 8,020,564 B2 | 9/2011 | Batch |
| 8,021,577 B2 | 9/2011 | Johnson |
| 8,025,786 B2 | 9/2011 | Field et al. |
| 8,025,787 B2 | 9/2011 | Field et al. |
| 8,025,807 B2 | 9/2011 | Centanni |
| 8,026,821 B2 | 9/2011 | Reeder et al. |
| 8,029,726 B2 | 10/2011 | Resch |
| 8,043,439 B2 | 10/2011 | Park |
| 8,043,441 B2 | 10/2011 | de Larios |
| 8,046,867 B2 | 11/2011 | Field et al. |
| 8,048,279 B2 | 11/2011 | Powell |
| 8,053,401 B2 | 11/2011 | Thonhauser et al. |
| 8,053,404 B2 | 11/2011 | Singh et al. |
| 8,057,812 B2 | 11/2011 | Man et al. |
| 8,065,882 B2 | 11/2011 | Singh et al. |
| 8,070,882 B2 | 12/2011 | Schwab |
| 8,071,526 B2 | 12/2011 | Lynn |
| 8,071,687 B2 | 12/2011 | Jiang et al. |
| 8,072,576 B2 | 12/2011 | Kobayashi et al. |
| 8,075,705 B2 | 12/2011 | Lynn |
| 8,082,857 B2 | 12/2011 | George et al. |
| 8,084,394 B2 | 12/2011 | Steffen |
| 8,085,381 B2 | 12/2011 | Kawai |
| 8,088,867 B2 | 1/2012 | Jiang et al. |
| 8,097,166 B2 | 1/2012 | Nakashima |
| 8,099,802 B2 | 1/2012 | Yamaguchi et al. |
| 8,105,494 B2 | 1/2012 | Miks |
| 8,105,558 B2 | 1/2012 | Comrie |
| 8,115,899 B2 | 2/2012 | Jansen |
| 8,118,240 B2 | 2/2012 | Rodenbeck et al. |
| 8,125,612 B2 | 2/2012 | Kobayashi et al. |
| 8,127,396 B2 | 3/2012 | Mangiardi |
| 8,128,888 B2 | 3/2012 | Bacik |
| 8,130,363 B2 | 3/2012 | Kobayashi et al. |
| 8,132,870 B2 | 3/2012 | Buczynski |
| 8,133,382 B2 | 3/2012 | Powell |
| 8,133,546 B2 | 3/2012 | Kumazawa |
| 8,134,682 B2 | 3/2012 | Kobayashi |
| 8,141,520 B2 | 3/2012 | Matsumura |
| 8,142,550 B2 | 3/2012 | Audunson |
| 8,147,889 B2 | 4/2012 | Kirkpatrick et al. |
| 8,148,317 B2 | 4/2012 | Singh et al. |
| 8,152,142 B2 | 4/2012 | Hirakui |
| 8,153,078 B2 | 4/2012 | Bacik |
| 8,156,608 B2 | 4/2012 | Field et al. |
| 8,158,152 B2 | 4/2012 | Palepu |
| 8,163,236 B1 | 4/2012 | Bacik |
| 8,163,243 B1 | 4/2012 | Burke |
| 8,163,689 B2 | 4/2012 | Singh et al. |
| 8,168,225 B2 | 5/2012 | Giner |
| 8,169,327 B2 | 5/2012 | Lynn |
| 8,169,592 B2 | 5/2012 | Kobayashi et al. |
| 8,174,668 B2 | 5/2012 | Kobayashi et al. |
| 8,182,743 B1 | 5/2012 | Bacik |
| 8,183,670 B2 | 5/2012 | Ohmi |
| 8,187,201 B2 | 5/2012 | Lynn |
| 8,192,968 B2 | 6/2012 | Edwards |
| 8,193,289 B2 | 6/2012 | Abhari et al. |
| 8,196,810 B2 | 6/2012 | Sahud |
| 8,197,698 B2 | 6/2012 | Johnson |
| 8,202,500 B2 | 6/2012 | Fahs |
| 8,206,647 B2 | 6/2012 | Kirkpatrick |
| 8,207,060 B2 | 6/2012 | Yang |
| 8,216,523 B2 | 7/2012 | Meilander |
| 8,216,630 B2 | 7/2012 | Autefage |
| 8,217,573 B2 | 7/2012 | Yoshida et al. |
| 8,222,345 B2 | 7/2012 | Abhari et al. |
| 8,226,832 B2 | 7/2012 | Angelilli |
| 8,237,558 B2 | 8/2012 | Seyed Momen et al. |
| 8,242,324 B2 | 8/2012 | Johnson |
| 8,243,195 B2 | 8/2012 | Eymard |
| 8,249,295 B2 | 8/2012 | Johnson |
| 8,252,359 B2 | 8/2012 | Ghosh |
| 8,258,965 B2 | 9/2012 | Reeder et al. |
| 8,262,741 B2 | 9/2012 | Estes |
| 8,263,045 B2 | 9/2012 | Dueva-Koganov |
| 8,267,101 B2 | 9/2012 | Beard |
| 8,268,931 B2 | 9/2012 | Tong |
| 8,269,946 B2 | 9/2012 | Kawai |
| 8,276,603 B2 | 10/2012 | Berklund |
| 8,279,063 B2 | 10/2012 | Wohltjen |
| 8,287,702 B2 | 10/2012 | Gomez |
| 8,293,669 B2 | 10/2012 | Kirkpatrick |
| 8,294,584 B2 | 10/2012 | Plost |
| 8,304,232 B2 | 11/2012 | Morgan |
| 8,316,866 B2 | 11/2012 | Freer |
| 8,317,993 B2 | 11/2012 | Kuriyama |
| 8,318,027 B2 | 11/2012 | McGuire |
| 8,318,188 B2 | 11/2012 | Man et al. |
| 8,330,359 B2 | 12/2012 | Yoshida et al. |
| 8,340,792 B2 | 12/2012 | Condurso et al. |
| 8,342,194 B2 | 1/2013 | Berner et al. |
| 8,343,341 B2 | 1/2013 | Davis |
| 8,343,359 B2 | 1/2013 | Daines |
| 8,343,437 B2 | 1/2013 | Patel |
| 8,350,706 B2 | 1/2013 | Wegelin et al. |
| 8,362,310 B2 | 1/2013 | Blessing |
| 8,366,920 B2 | 2/2013 | Davis |
| 8,367,007 B2 | 2/2013 | Otero |
| 8,367,025 B2 | 2/2013 | Comrie |
| 8,368,544 B2 | 2/2013 | Wildman et al. |
| 8,372,207 B1 | 2/2013 | Shields |
| 8,375,965 B2 | 2/2013 | Puri |
| 8,376,254 B2 | 2/2013 | Hatten |
| 8,377,279 B2 | 2/2013 | Jha |
| 8,384,877 B2 | 2/2013 | Kobayashi et al. |
| 8,388,731 B2 | 3/2013 | Metteer |
| 8,394,306 B2 | 3/2013 | Nishida et al. |
| 8,395,515 B2 | 3/2013 | Tokhtuev et al. |
| 8,409,334 B2 | 4/2013 | Audunson |
| 8,409,353 B2 | 4/2013 | Yokota |
| 8,414,748 B2 | 4/2013 | Carson |
| 8,425,857 B2 | 4/2013 | Glazer |
| 8,426,175 B2 | 4/2013 | Edwards |
| 8,440,154 B2 | 5/2013 | Fahs |
| 8,444,942 B2 | 5/2013 | Suchak |
| 8,445,381 B2 | 5/2013 | Ramkumar |
| 8,448,848 B2 | 5/2013 | Sahud |
| 8,449,690 B2 | 5/2013 | Jeong et al. |
| 8,449,777 B2 | 5/2013 | Bain |
| 8,450,925 B2 | 5/2013 | Seo |
| 8,454,754 B2 | 6/2013 | Shibata |
| 8,454,831 B2 | 6/2013 | Sauvignet |
| 8,459,277 B2 | 6/2013 | Varrin, Jr. et al. |
| 8,460,605 B2 | 6/2013 | Meilander |
| 8,461,055 B2 | 6/2013 | Radouane |
| 8,475,599 B2 | 7/2013 | Freer |
| 8,480,613 B2 | 7/2013 | Nakamura |
| 8,480,810 B2 | 7/2013 | Freer |
| 8,480,847 B2 | 7/2013 | Amano |
| 8,480,888 B2 | 7/2013 | Ashley |
| 8,482,406 B2 | 7/2013 | Snodgrass |

(56) References Cited

U.S. PATENT DOCUMENTS

| | | |
|---|---|---|
| 8,486,225 B2 | 7/2013 | Aono |
| 8,486,331 B2 | 7/2013 | Uhm |
| 8,487,774 B2 | 7/2013 | Reeder et al. |
| 8,492,327 B2 | 7/2013 | Singh et al. |
| 8,493,545 B2 | 7/2013 | Kawai |
| 8,496,759 B2 | 7/2013 | Heiligenmann et al. |
| 8,497,405 B1 | 7/2013 | Meilander |
| 8,502,680 B2 | 8/2013 | Tokhtuev |
| 8,505,477 B2 | 8/2013 | Makover |
| 8,506,724 B2 | 8/2013 | Kirkpatrick |
| 8,512,796 B2 | 8/2013 | Felts et al. |
| 8,518,269 B2 | 8/2013 | Fischmann T. |
| 8,518,634 B2 | 8/2013 | Yeh |
| 8,520,184 B2 | 8/2013 | Shiraishi |
| 8,522,799 B2 | 9/2013 | Freer |
| 8,522,801 B2 | 9/2013 | Freer |
| 8,525,666 B2 | 9/2013 | Melker et al. |
| 8,525,971 B2 | 9/2013 | Shiraishi |
| 8,563,647 B2 | 10/2013 | Jiang et al. |
| 8,564,759 B2 | 10/2013 | Chang et al. |
| 8,569,555 B2 | 10/2013 | Blessing |
| 8,571,708 B2 | 10/2013 | Rob |
| 8,572,826 B2 | 11/2013 | Bilgen et al. |
| 8,574,371 B2 | 11/2013 | Folz et al. |
| 8,574,502 B2 | 11/2013 | Uhm |
| 8,584,852 B2 | 11/2013 | Zucker |
| 8,587,437 B2 | 11/2013 | Kyle et al. |
| 8,591,660 B2 | 11/2013 | Silberberg et al. |
| 8,591,662 B2 | 11/2013 | Freer |
| 8,598,996 B2 | 12/2013 | Wildman et al. |
| 8,603,320 B2 | 12/2013 | Field |
| 8,609,120 B2 | 12/2013 | Heacox |
| 8,609,191 B2 | 12/2013 | Raetz |
| 8,618,219 B2 | 12/2013 | Jiang et al. |
| 8,623,808 B2 | 1/2014 | Singh et al. |
| 8,629,971 B2 | 1/2014 | Dierichs |
| 8,630,722 B2 | 1/2014 | Condurso et al. |
| 8,632,655 B2 | 1/2014 | Vehmaa |
| 8,632,656 B2 | 1/2014 | Vehmaa |
| 8,638,419 B2 | 1/2014 | Jansen |
| 8,646,121 B2 | 2/2014 | Nguyen |
| 8,652,404 B2 | 2/2014 | Glazer |
| 8,653,169 B2 | 2/2014 | Jiang et al. |
| 8,653,199 B2 | 2/2014 | Abhari et al. |
| 8,664,092 B2 | 3/2014 | Kawasaki |
| 8,667,817 B2 | 3/2014 | Smith |
| 8,670,103 B2 | 3/2014 | Hazelton |
| 8,670,104 B2 | 3/2014 | Hazelton |
| 8,671,959 B2 | 3/2014 | de Larios |
| 8,672,156 B2 | 3/2014 | Martinovic |
| 8,674,840 B2 | 3/2014 | Snodgrass |
| 8,679,999 B2 | 3/2014 | Kanagasabapathy |
| 8,685,446 B2 | 4/2014 | Moser |
| 8,696,873 B2 | 4/2014 | Karlstrom et al. |
| 8,698,998 B2 | 4/2014 | Nagasaka et al. |
| 8,703,006 B2 | 4/2014 | Basu |
| 8,703,605 B2 | 4/2014 | Yang |
| 8,704,997 B2 | 4/2014 | Shiraishi |
| 8,709,137 B2 | 4/2014 | Chan et al. |
| 8,716,210 B2 | 5/2014 | Freer |
| 8,719,999 B2 | 5/2014 | Field |
| 8,721,898 B2 | 5/2014 | McGuire |
| 8,722,565 B2 | 5/2014 | Mestl et al. |
| 8,725,526 B2 | 5/2014 | Cobbs et al. |
| 8,726,918 B2 | 5/2014 | Watanabe |
| 8,734,727 B2 | 5/2014 | Zimmerman |
| 8,734,741 B1 | 5/2014 | Suchak |
| 8,736,453 B2 | 5/2014 | Wilson et al. |
| 8,741,829 B2 | 6/2014 | Singh et al. |
| 8,742,932 B2 | 6/2014 | Casares |
| 8,747,178 B2 | 6/2014 | Seo |
| 8,753,449 B2 | 6/2014 | Chhabra |
| 8,753,518 B2 | 6/2014 | Brunsell |
| 8,753,520 B1 | 6/2014 | Fischmann |
| 8,758,621 B2 | 6/2014 | Zuback |
| 8,758,789 B2 | 6/2014 | Man et al. |
| 8,760,617 B2 | 6/2014 | Kobayashi et al. |
| 8,761,906 B2 | 6/2014 | Condurso et al. |
| 8,766,804 B2 | 7/2014 | Reeder et al. |
| 8,777,064 B2 | 7/2014 | Williams et al. |
| 8,784,669 B2 | 7/2014 | Bain |
| 8,784,762 B2 | 7/2014 | Moore |
| 8,795,620 B2 | 8/2014 | Moore |
| 8,808,550 B2 | 8/2014 | Dholakia |
| 8,808,809 B2 | 8/2014 | Makeover |
| 8,823,490 B2 | 9/2014 | Libbus et al. |
| 8,824,501 B2 | 9/2014 | Liu |
| 8,834,954 B2 | 9/2014 | Felts et al. |
| 8,841,545 B2 | 9/2014 | Wakayama |
| 8,844,324 B2 | 9/2014 | Tobi |
| 8,844,766 B2 | 9/2014 | Zaima et al. |
| 8,845,782 B2 | 9/2014 | Metteer |
| 8,845,976 B2 | 9/2014 | Beldring |
| 8,846,754 B2 | 9/2014 | Hulse |
| 8,852,437 B2 | 10/2014 | Zacharias |
| 8,862,196 B2 | 10/2014 | Lynn |
| 8,864,971 B2 | 10/2014 | Jha |
| 8,865,098 B2 | 10/2014 | Suchak |
| 8,872,665 B2 | 10/2014 | Snodgrass |
| 8,875,547 B2 | 11/2014 | Suzuki |
| 8,877,003 B2 | 11/2014 | Silberberg et al. |
| 8,883,083 B2 | 11/2014 | Law |
| 8,883,708 B2 | 11/2014 | Singh et al. |
| 8,888,902 B2 | 11/2014 | Galbraith |
| 8,889,253 B2 | 11/2014 | Kekicheff |
| 8,902,068 B2 | 12/2014 | Bechtel et al. |
| 8,904,846 B2 | 12/2014 | Mader et al. |
| 8,905,052 B2 | 12/2014 | Ulger et al. |
| 8,906,228 B2 | 12/2014 | O'Rear |
| 8,906,242 B2 | 12/2014 | McGuire |
| 8,911,755 B2 | 12/2014 | Curry |
| 8,911,783 B2 | 12/2014 | Giner |
| 8,919,743 B2 | 12/2014 | Osborn |
| 8,932,408 B2 | 1/2015 | Sellmer |
| 8,932,410 B2 | 1/2015 | Ulger et al. |
| 8,932,702 B2 | 1/2015 | Phillips et al. |
| 8,934,786 B2 | 1/2015 | Liu |
| 8,937,429 B2 | 1/2015 | Seo |
| 8,937,625 B2 | 1/2015 | Lee |
| 8,940,100 B2 | 1/2015 | Yoneda et al. |
| 8,940,101 B2 | 1/2015 | Jeong |
| 8,941,811 B2 | 1/2015 | Jansen |
| 8,945,310 B2 | 2/2015 | Zink et al. |
| 8,945,499 B2 | 2/2015 | Johnston et al. |
| 8,951,477 B2 | 2/2015 | Russell |
| 8,953,144 B2 | 2/2015 | Dierichs |
| 8,956,466 B2 | 2/2015 | Blaiss et al. |
| 8,957,159 B2 | 2/2015 | Jiang et al. |
| 8,958,468 B2 | 2/2015 | Servaes |
| 8,961,478 B2 | 2/2015 | Nakamura |
| 8,962,597 B2 | 2/2015 | Rieth et al. |
| 8,981,403 B2 | 3/2015 | Shatalov |
| 8,987,188 B2 | 3/2015 | Huboux et al. |
| 8,992,769 B2 | 3/2015 | O'Rear |
| 8,993,314 B2 | 3/2015 | Eckelberry |
| 8,999,072 B2 | 4/2015 | Varrin, Jr. et al. |
| 8,999,154 B2 | 4/2015 | McGuire |
| 8,999,173 B2 | 4/2015 | Schwartzel |
| 8,999,261 B2 | 4/2015 | Benedetto |
| 9,000,926 B2 | 4/2015 | Hollock et al. |
| 9,000,930 B2 | 4/2015 | Pelland et al. |
| 9,005,156 B2 | 4/2015 | Nakamura |
| 9,005,531 B2 | 4/2015 | Mole |
| 9,009,882 B2 | 4/2015 | Bucher |
| 9,011,682 B2 | 4/2015 | Volker |
| 9,011,787 B2 | 4/2015 | Dunkley et al. |
| 9,021,792 B2 | 5/2015 | Hosoya |
| 9,025,127 B2 | 5/2015 | Dierichs |
| 9,027,369 B2 | 5/2015 | Mueller |
| 9,027,795 B2 | 5/2015 | Zaima et al. |
| 9,028,695 B2 | 5/2015 | Noguchi et al. |
| 9,031,793 B2 | 5/2015 | Lynn et al. |
| 9,034,180 B2 | 5/2015 | McGuire |
| 9,034,183 B2 | 5/2015 | Davis |

(56) References Cited

U.S. PATENT DOCUMENTS

| | | |
|---|---|---|
| 9,043,019 B2 | 5/2015 | Eliuk |
| 9,051,193 B2 | 6/2015 | Fischmann T. |
| 9,051,404 B2 | 6/2015 | Jiang et al. |
| 9,060,667 B2 | 6/2015 | Jeong |
| 9,062,333 B2 | 6/2015 | Lehr |
| 9,069,887 B2 | 6/2015 | Gupta et al. |
| 9,073,762 B2 | 7/2015 | Cummins |
| 9,073,766 B2 | 7/2015 | Fahs |
| 9,074,286 B2 | 7/2015 | Mayer |
| 9,074,355 B2 | 7/2015 | Jallon |
| 9,085,842 B2 | 7/2015 | Ulger et al. |
| 9,089,811 B2 | 7/2015 | Vickery |
| 9,095,153 B2 | 8/2015 | Xu |
| 9,096,911 B2 | 8/2015 | Binder |
| 9,099,298 B2 | 8/2015 | Dobashi |
| 9,101,528 B2 | 8/2015 | Nakamura |
| 9,111,435 B2 | 8/2015 | Gips et al. |
| 9,114,183 B2 | 8/2015 | Campagna |
| 9,120,966 B2 | 9/2015 | Roccon |
| 9,123,233 B2 | 9/2015 | Hermann |
| 9,125,529 B2 | 9/2015 | Stine |
| 9,126,855 B2 | 9/2015 | Weist |
| 9,129,797 B2 | 9/2015 | Tokoshima |
| 9,131,826 B2 | 9/2015 | Heiligenmann |
| 9,133,109 B2 | 9/2015 | Antebi |
| 9,149,755 B2 | 10/2015 | Lee |
| 9,150,768 B2 | 10/2015 | Cook |
| 9,157,017 B2 | 10/2015 | Singh et al. |
| 9,169,146 B2 | 10/2015 | McGuire |
| 9,169,597 B2 | 10/2015 | Aharon |
| 9,174,845 B2 | 11/2015 | Lynn |
| 9,187,344 B2 | 11/2015 | Kolstad |
| 9,187,347 B2 | 11/2015 | Van Vliet |
| 9,187,884 B2 | 11/2015 | Belz et al. |
| 9,188,385 B2 | 11/2015 | Armellin |
| 9,192,686 B2 | 11/2015 | Graydon |
| 9,193,614 B2 | 11/2015 | McGuffin |
| 9,220,800 B2 | 12/2015 | Shenberg |
| 9,221,114 B2 | 12/2015 | Chen et al. |
| 9,226,495 B2 | 1/2016 | Berentsveig et al. |
| 9,227,283 B2 | 1/2016 | Zhu |
| 9,227,852 B2 | 1/2016 | Robinson |
| 9,230,421 B2 | 1/2016 | Reeder et al. |
| 9,249,252 B2 | 2/2016 | Ngantung |
| 9,254,358 B2 | 2/2016 | Volker |
| 9,259,006 B2 | 2/2016 | Lemons |
| 9,260,327 B2 | 2/2016 | Merayo |
| 9,266,760 B2 | 2/2016 | Wang |
| 9,278,153 B1 | 3/2016 | Tsang |
| 9,278,204 B2 | 3/2016 | Nakamura |
| 9,283,418 B2 | 3/2016 | Brunsell |
| 9,287,800 B2 | 3/2016 | Hruska |
| 9,295,623 B2 | 3/2016 | Curry |
| 9,295,966 B1 | 3/2016 | Appelbaum |
| 9,296,551 B2 | 3/2016 | Klein et al. |
| 9,296,629 B2 | 3/2016 | Van Vliet |
| 9,297,085 B2 | 3/2016 | Kitaori |
| 9,300,400 B2 | 3/2016 | Liu |
| 9,301,910 B2 | 4/2016 | Yontz |
| 9,303,394 B2 | 4/2016 | Mock |
| 9,304,392 B2 | 4/2016 | Kobayashi et al. |
| 9,305,191 B2 | 4/2016 | Long et al. |
| 9,307,907 B2 | 4/2016 | Condurso et al. |
| 9,308,492 B2 | 4/2016 | Obee |
| 9,311,809 B2 | 4/2016 | Diaz |
| 9,321,665 B2 | 4/2016 | Kolstad |
| 9,334,183 B2 | 5/2016 | Fahs |
| 9,334,518 B2 | 5/2016 | Medoff |
| 9,340,438 B2 | 5/2016 | Linguist |
| 9,340,918 B2 | 5/2016 | Lv |
| 9,349,267 B2 | 5/2016 | Wildman et al. |
| 9,359,234 B2 | 6/2016 | Kirk |
| 9,362,504 B2 | 6/2016 | Lee |
| 9,365,439 B1 | 6/2016 | Guardino |
| 9,370,745 B2 | 6/2016 | Xu et al. |
| 9,371,228 B2 | 6/2016 | Golden |
| 9,373,242 B1 | 6/2016 | Conrad et al. |
| 9,375,500 B2 | 6/2016 | Dunkley et al. |
| 9,375,663 B2 | 6/2016 | Pett |
| 9,380,920 B2 | 7/2016 | Pollack |
| 9,382,500 B2 | 7/2016 | Huboux et al. |
| 9,392,815 B2 | 7/2016 | Russell |
| 9,394,189 B2 | 7/2016 | Buchanan |
| 9,396,638 B2 | 7/2016 | Wildman et al. |
| 9,403,122 B2 | 8/2016 | Geckeler |
| 9,427,728 B2 | 8/2016 | Sidheswaran |
| 9,440,188 B2 | 9/2016 | Suchak |
| 9,440,964 B2 | 9/2016 | Crouse et al. |
| 9,445,719 B2 | 9/2016 | Libbus et al. |
| 9,446,352 B2 | 9/2016 | Tomimatsu et al. |
| 9,447,505 B2 | 9/2016 | Mayer |
| 9,449,841 B2 | 9/2016 | Suen |
| 9,451,759 B2 | 9/2016 | Kuo |
| 9,451,765 B2 | 9/2016 | Cuer |
| 9,451,787 B2 | 9/2016 | Russell |
| 9,451,866 B2 | 9/2016 | Franco |
| 9,451,867 B2 | 9/2016 | Beshears |
| 9,456,602 B2 | 10/2016 | DeMattei et al. |
| 9,458,536 B2 | 10/2016 | Felts et al. |
| 9,464,334 B2 | 10/2016 | Medoff |
| 9,472,089 B2 | 10/2016 | Alhazme |
| 9,475,065 B2 | 10/2016 | Ilmasti |
| 9,486,817 B2 | 11/2016 | Patton |
| 9,487,913 B2 | 11/2016 | Urbini |
| 9,491,965 B2 | 11/2016 | Man et al. |
| 9,492,781 B2 | 11/2016 | Galbraith |
| 9,493,364 B2 | 11/2016 | Johnston et al. |
| 9,497,428 B2 | 11/2016 | Gaisser et al. |
| 9,498,762 B2 | 11/2016 | Carlberg |
| 9,511,161 B2 | 12/2016 | Matts et al. |
| 9,518,225 B2 | 12/2016 | Singh et al. |
| 9,518,749 B2 | 12/2016 | Kim |
| 9,522,348 B2 | 12/2016 | Lynn |
| 9,529,267 B2 | 12/2016 | Rho |
| 9,536,415 B2 | 1/2017 | De Luca et al. |
| 9,538,886 B2 | 1/2017 | Marin |
| 9,539,193 B2 | 1/2017 | Rieth et al. |
| 9,545,360 B2 | 1/2017 | Felts et al. |
| 9,549,886 B2 | 1/2017 | Yontz et al. |
| 9,553,004 B2 | 1/2017 | Takemura |
| 9,562,318 B2 | 2/2017 | Youn |
| 9,564,039 B2 | 2/2017 | Hermann |
| 9,572,526 B2 | 2/2017 | Felts et al. |
| 9,579,255 B2 | 2/2017 | Eliuk |
| 9,581,914 B2 | 2/2017 | Dierichs |
| 9,586,244 B2 | 3/2017 | Glazer |
| 9,586,810 B2 | 3/2017 | Fuhrmann et al. |
| 9,592,413 B2 | 3/2017 | Hulse |
| 9,605,223 B2 | 3/2017 | Beldring |
| 9,613,518 B2 | 4/2017 | Dunn et al. |
| 9,617,177 B2 | 4/2017 | Kolstad |
| 9,630,866 B2 | 4/2017 | Fritz |
| 9,631,129 B2 | 4/2017 | Thomas et al. |
| 9,640,059 B2 | 5/2017 | Hyland |
| 9,645,505 B2 | 5/2017 | Shiraishi |
| 9,649,712 B2 | 5/2017 | Chen et al. |
| 9,650,270 B2 | 5/2017 | Kolstad |
| 9,652,969 B2 | 5/2017 | Herzog |
| 9,666,061 B2 | 5/2017 | Reeder et al. |
| 9,670,081 B2 | 6/2017 | Lynn |
| 9,672,726 B2 | 6/2017 | Borke et al. |
| 9,679,464 B2 | 6/2017 | Marra et al. |
| 9,694,317 B2 | 7/2017 | Littleford |
| 9,695,363 B2 | 7/2017 | Singh et al. |
| 9,696,049 B2 | 7/2017 | Metteer |
| 9,700,195 B2 | 7/2017 | Padtberg et al. |
| 9,703,210 B2 | 7/2017 | Jansen |
| 9,708,537 B2 | 7/2017 | Singh et al. |
| 9,708,761 B2 | 7/2017 | Medoff |
| 9,715,817 B2 | 7/2017 | Wildman et al. |
| 9,731,368 B2 | 8/2017 | Chen et al. |
| 9,735,026 B2 | 8/2017 | Brown |
| 9,738,548 B2 | 8/2017 | Guardino |
| 9,741,233 B2 | 8/2017 | Laufer et al. |

(56) References Cited

U.S. PATENT DOCUMENTS

| | | |
|---|---|---|
| 9,745,211 B2 | 8/2017 | Davis |
| 9,758,411 B2 | 9/2017 | Valdes Simancas |
| 9,758,716 B2 | 9/2017 | Roccon |
| 9,759,673 B2 | 9/2017 | Rapoport |
| 9,782,053 B2 | 10/2017 | Gilreath |
| 9,856,634 B2 | 1/2018 | Rodenbeck et al. |
| 9,919,939 B2 | 3/2018 | Rosko et al. |
| 10,640,878 B2 | 5/2020 | Jonte et al. |
| 10,767,270 B2 | 9/2020 | Jonte et al. |
| 11,220,754 B2 | 1/2022 | Jonte et al. |
| 2001/0040133 A1 | 11/2001 | Wang |
| 2002/0011257 A1 | 1/2002 | BeGendt et al. |
| 2002/0014951 A1 | 2/2002 | Kramer et al. |
| 2002/0019709 A1 | 2/2002 | Segal |
| 2002/0023419 A1 | 2/2002 | Penth |
| 2002/0036673 A1 | 3/2002 | Miyoshi |
| 2002/0040867 A1 | 4/2002 | Conrad |
| 2002/0044059 A1 | 4/2002 | Reeder et al. |
| 2002/0045421 A1 | 4/2002 | Demerath |
| 2002/0048539 A1 | 4/2002 | Mackay |
| 2002/0056163 A1 | 5/2002 | Estes |
| 2002/0060189 A1 | 5/2002 | Conrad |
| 2002/0066464 A1 | 6/2002 | Bergman |
| 2002/0071795 A1 | 6/2002 | Jensen |
| 2002/0088478 A1 | 7/2002 | DeGendt et al. |
| 2002/0094363 A1 | 7/2002 | Traeder et al. |
| 2002/0103674 A1 | 8/2002 | Reeder et al. |
| 2002/0104271 A1 | 8/2002 | Gallant |
| 2002/0121482 A1 | 9/2002 | Ciampi et al. |
| 2002/0130091 A1 | 9/2002 | Ekberg et al. |
| 2002/0133886 A1 | 9/2002 | Severns et al. |
| 2002/0134736 A1 | 9/2002 | Burris et al. |
| 2002/0146357 A1 | 10/2002 | Yeh |
| 2002/0150678 A1 | 10/2002 | Cramer et al. |
| 2002/0151634 A1 | 10/2002 | Rohrbaugh et al. |
| 2002/0152556 A1 | 10/2002 | Ascione et al. |
| 2002/0155044 A1 | 10/2002 | Ciampi et al. |
| 2002/0157686 A1 | 10/2002 | Kenny |
| 2002/0160159 A1 | 10/2002 | McDonald et al. |
| 2002/0174483 A1 | 11/2002 | Gallant |
| 2002/0192366 A1 | 12/2002 | Cramer et al. |
| 2002/0195127 A1 | 12/2002 | Morioka |
| 2002/0195131 A1 | 12/2002 | Morioka et al. |
| 2003/0000522 A1 | 1/2003 | Lynn et al. |
| 2003/0009244 A1 | 1/2003 | Engleson et al. |
| 2003/0009825 A1 | 1/2003 | Gallant et al. |
| 2003/0009952 A1 | 1/2003 | Gallant et al. |
| 2003/0014817 A1 | 1/2003 | Gallant et al. |
| 2003/0019165 A1 | 1/2003 | Gallant et al. |
| 2003/0019536 A1 | 1/2003 | Smith |
| 2003/0025909 A1 | 2/2003 | Hallstadius |
| 2003/0046770 A1 | 3/2003 | Sanduja et al. |
| 2003/0071069 A1 | 4/2003 | Shelton |
| 2003/0080467 A1 | 5/2003 | Andrews et al. |
| 2003/0091749 A1 | 5/2003 | France et al. |
| 2003/0099584 A1 | 5/2003 | Diang |
| 2003/0108460 A1 | 6/2003 | Andreev et al. |
| 2003/0108648 A1 | 6/2003 | Ming et al. |
| 2003/0140947 A1 | 7/2003 | Han |
| 2003/0146169 A1 | 8/2003 | Ciampi et al. |
| 2003/0168764 A1 | 9/2003 | Nishida et al. |
| 2003/0170988 A1 | 9/2003 | Izumi |
| 2003/0182019 A1 | 9/2003 | Bonini et al. |
| 2003/0226751 A1 | 12/2003 | Kasten |
| 2003/0235996 A1 | 12/2003 | Leon et al. |
| 2004/0009271 A1 | 1/2004 | Davidson |
| 2004/0033930 A1 | 2/2004 | Thonhauser |
| 2004/0035448 A1 | 2/2004 | Aegerter |
| 2004/0037932 A1 | 2/2004 | Garwood |
| 2004/0052957 A1 | 3/2004 | Cramer et al. |
| 2004/0062697 A1 | 4/2004 | Mortson |
| 2004/0065623 A1 | 4/2004 | Lee |
| 2004/0072948 A1 | 4/2004 | Sanduja et al. |
| 2004/0073329 A1 | 4/2004 | Engelson et al. |
| 2004/0087665 A1 | 5/2004 | Aubert et al. |
| 2004/0089839 A1 | 5/2004 | Thomas et al. |
| 2004/0090333 A1 | 5/2004 | Wildman et al. |
| 2004/0114596 A1 | 6/2004 | Ha et al. |
| 2004/0119047 A1 | 6/2004 | Singh et al. |
| 2004/0121316 A1 | 6/2004 | Birkus et al. |
| 2004/0123489 A1 | 7/2004 | Pancheri |
| 2004/0123490 A1 | 7/2004 | Pancheri |
| 2004/0127383 A1 | 7/2004 | Pham et al. |
| 2004/0127614 A1 | 7/2004 | Jiang et al. |
| 2004/0129032 A1 | 7/2004 | Severns et al. |
| 2004/0138392 A1 | 7/2004 | Jiang et al. |
| 2004/0139555 A1 | 7/2004 | Conrad |
| 2004/0140269 A1 | 7/2004 | Chang |
| 2004/0143459 A1 | 7/2004 | Engleson et al. |
| 2004/0152583 A1 | 8/2004 | Grosch |
| 2004/0161508 A1 | 8/2004 | Traeder et al. |
| 2004/0192135 A1 | 9/2004 | Lee |
| 2004/0220320 A1 | 11/2004 | Abhari et al. |
| 2004/0220336 A1 | 11/2004 | Abhari et al. |
| 2004/0220359 A1 | 11/2004 | Abhari et al. |
| 2004/0226106 A1 | 11/2004 | Gardner et al. |
| 2004/0226581 A1 | 11/2004 | Gardner et al. |
| 2004/0231371 A1 | 11/2004 | Scheper et al. |
| 2004/0232253 A1 | 11/2004 | Hansen |
| 2004/0242862 A1 | 12/2004 | Hammes |
| 2004/0249046 A1 | 12/2004 | Abhari et al. |
| 2004/0256594 A1 | 12/2004 | Singh et al. |
| 2004/0259750 A1 | 12/2004 | DuVal |
| 2004/0265200 A1 | 12/2004 | Kim |
| 2005/0000911 A1 | 1/2005 | Thorpe |
| 2005/0005954 A1 | 1/2005 | Barani |
| 2005/0008555 A1 | 1/2005 | Hsieh et al. |
| 2005/0017380 A1 | 1/2005 | Namespetra et al. |
| 2005/0032391 A1 | 2/2005 | Peace |
| 2005/0034745 A1 | 2/2005 | Bergman |
| 2005/0035862 A1 | 2/2005 | Wildman et al. |
| 2005/0043196 A1 | 2/2005 | Wright |
| 2005/0050644 A1 | 3/2005 | Severns et al. |
| 2005/0065060 A1 | 3/2005 | Kin et al. |
| 2005/0071928 A1 | 4/2005 | Wright |
| 2005/0072446 A1 | 4/2005 | Bergman |
| 2005/0087554 A1 | 4/2005 | Shelton |
| 2005/0093182 A1 | 5/2005 | Morita |
| 2005/0103329 A1 | 5/2005 | Essig |
| 2005/0103722 A1 | 5/2005 | Freydina et al. |
| 2005/0107913 A1 | 5/2005 | Engleson et al. |
| 2005/0107914 A1 | 5/2005 | Engleson et al. |
| 2005/0113945 A1 | 5/2005 | Engleson et al. |
| 2005/0118436 A1 | 6/2005 | Bhangale |
| 2005/0119788 A1 | 6/2005 | Engleson et al. |
| 2005/0119914 A1 | 6/2005 | Batch |
| 2005/0129571 A1 | 6/2005 | Centanni |
| 2005/0135306 A1 | 6/2005 | McAllen et al. |
| 2005/0136397 A1 | 6/2005 | McDermott |
| 2005/0152991 A1 | 7/2005 | Man et al. |
| 2005/0161433 A1 | 7/2005 | Silberberg et al. |
| 2005/0167368 A1 | 8/2005 | Gehringer |
| 2005/0167369 A1 | 8/2005 | Robinson |
| 2005/0168341 A1 | 8/2005 | Reeder et al. |
| 2005/0176604 A1 | 8/2005 | Lee |
| 2005/0192197 A1 | 9/2005 | Man et al. |
| 2005/0197320 A1 | 9/2005 | Chen et al. |
| 2005/0199484 A1 | 9/2005 | Olstowski |
| 2005/0209197 A1 | 9/2005 | Arimilli et al. |
| 2005/0214182 A1 | 9/2005 | Lu |
| 2005/0215063 A1 | 9/2005 | Bergman |
| 2005/0217706 A1 | 10/2005 | Banerjee |
| 2005/0217707 A1 | 10/2005 | Aegerter |
| 2005/0233589 A1 | 10/2005 | Aegerter |
| 2005/0233931 A1 | 10/2005 | Singh et al. |
| 2005/0238812 A1 | 10/2005 | Bhangale |
| 2005/0241805 A1 | 11/2005 | Singh et al. |
| 2005/0245421 A1 | 11/2005 | Singh et al. |
| 2005/0247905 A1 | 11/2005 | Singh et al. |
| 2005/0268944 A1 | 12/2005 | Bexten |
| 2005/0269256 A1 | 12/2005 | Haq |
| 2005/0274393 A1 | 12/2005 | Perng |
| 2005/0279686 A1 | 12/2005 | Hsu |
| 2005/0288204 A1 | 12/2005 | Matts et al. |

(56) References Cited

U.S. PATENT DOCUMENTS

| | | |
|---|---|---|
| 2006/0019857 A1 | 1/2006 | Wilson et al. |
| 2006/0020067 A1 | 1/2006 | Brant et al. |
| 2006/0021923 A1 | 2/2006 | Lin |
| 2006/0022166 A1 | 2/2006 | Wilson et al. |
| 2006/0027507 A1 | 2/2006 | Van Leeuwen |
| 2006/0029699 A1 | 2/2006 | Garwood |
| 2006/0032012 A1 | 2/2006 | Buckner |
| 2006/0033071 A1 | 2/2006 | Wilson et al. |
| 2006/0033072 A1 | 2/2006 | Wilson et al. |
| 2006/0043026 A1 | 3/2006 | Law |
| 2006/0043330 A1 | 3/2006 | Wilson et al. |
| 2006/0043331 A1 | 3/2006 | Shankland et al. |
| 2006/0046499 A1 | 3/2006 | Dolechek |
| 2006/0047538 A1 | 3/2006 | Condurso et al. |
| 2006/0051259 A1 | 3/2006 | Chiu |
| 2006/0054568 A1 | 3/2006 | Jones |
| 2006/0060226 A1 | 3/2006 | Yoon |
| 2006/0071799 A1 | 4/2006 | Verdiramo |
| 2006/0077367 A1 | 4/2006 | Kobayashi et al. |
| 2006/0078661 A1 | 4/2006 | Wang |
| 2006/0083844 A1 | 4/2006 | Sherwood et al. |
| 2006/0053546 A1 | 5/2006 | Gloodt |
| 2006/0108293 A1 | 5/2006 | Brolin et al. |
| 2006/0115815 A1 | 6/2006 | Birkus et al. |
| 2006/0116310 A1 | 6/2006 | Singh et al. |
| 2006/0118132 A1 | 6/2006 | Bergman |
| 2006/0118143 A1 | 6/2006 | Jeong et al. |
| 2006/0128692 A1 | 6/2006 | Chen et al. |
| 2006/0130907 A1 | 6/2006 | Marty et al. |
| 2006/0132316 A1 | 6/2006 | Wildman et al. |
| 2006/0137723 A1 | 6/2006 | Bergman |
| 2006/0141157 A1 | 6/2006 | Sekimoto |
| 2006/0146445 A1 | 7/2006 | Nolan et al. |
| 2006/0147602 A1 | 7/2006 | Sherwood et al. |
| 2006/0148167 A1 | 7/2006 | Brown et al. |
| 2006/0151007 A1 | 7/2006 | Bergman |
| 2006/0155206 A1 | 7/2006 | Lynn |
| 2006/0159813 A1 | 7/2006 | Ming et al. |
| 2006/0160276 A1 | 7/2006 | Brown et al. |
| 2006/0162180 A1 | 7/2006 | Heilman |
| 2006/0163169 A1 | 7/2006 | Eckhardt |
| 2006/0177987 A1 | 8/2006 | Bergman |
| 2006/0180532 A1 | 8/2006 | Cummins |
| 2006/0186215 A1 | 8/2006 | Logan |
| 2006/0191828 A1 | 8/2006 | Cummins |
| 2006/0195041 A1 | 8/2006 | Lynn et al. |
| 2006/0220329 A1 | 10/2006 | Dolechek |
| 2006/0235324 A1 | 10/2006 | Lynn |
| 2006/0260647 A1 | 11/2006 | Verhaverbeke |
| 2006/0264343 A1 | 11/2006 | Verhaverbeke |
| 2006/0266683 A1 | 11/2006 | Sung |
| 2007/0010489 A1 | 1/2007 | Arimilli et al. |
| 2007/0010592 A1 | 1/2007 | Bowman et al. |
| 2007/0020378 A1 | 1/2007 | Shirade |
| 2007/0021566 A1 | 1/2007 | Tse et al. |
| 2007/0026693 A1 | 2/2007 | Yokota |
| 2007/0028975 A1 | 2/2007 | Herring et al. |
| 2007/0064210 A1 | 3/2007 | Kobayashi et al. |
| 2007/0064986 A1 | 3/2007 | Johnson |
| 2007/0084829 A1 | 4/2007 | Hanson |
| 2007/0091287 A1 | 4/2007 | Chang et al. |
| 2007/0094046 A1 | 4/2007 | Cobbs et al. |
| 2007/0101867 A1 | 5/2007 | Hunter |
| 2007/0102280 A1 | 5/2007 | Hunter |
| 2007/0108135 A1 | 5/2007 | Davis |
| 2007/0113418 A1 | 5/2007 | Palmer |
| 2007/0116800 A1 | 5/2007 | Prakash et al. |
| 2007/0116819 A1 | 5/2007 | Prakash et al. |
| 2007/0116820 A1 | 5/2007 | Prakash et al. |
| 2007/0116821 A1 | 5/2007 | Prakash et al. |
| 2007/0116822 A1 | 5/2007 | Prakash et al. |
| 2007/0116823 A1 | 5/2007 | Prakash et al. |
| 2007/0116824 A1 | 5/2007 | Prakash et al. |
| 2007/0116825 A1 | 5/2007 | Prakash et al. |
| 2007/0116826 A1 | 5/2007 | Prakash et al. |
| 2007/0116827 A1 | 5/2007 | Prakash et al. |
| 2007/0116828 A1 | 5/2007 | Prakash et al. |
| 2007/0116829 A1 | 5/2007 | Prakash et al. |
| 2007/0116830 A1 | 5/2007 | Prakash et al. |
| 2007/0116831 A1 | 5/2007 | Prakash et al. |
| 2007/0116832 A1 | 5/2007 | Prakash et al. |
| 2007/0116833 A1 | 5/2007 | Prakash et al. |
| 2007/0116834 A1 | 5/2007 | Prakash et al. |
| 2007/0116835 A1 | 5/2007 | Prakash et al. |
| 2007/0116836 A1 | 5/2007 | Prakash et al. |
| 2007/0116837 A1 | 5/2007 | Prakash et al. |
| 2007/0116838 A1 | 5/2007 | Prakash et al. |
| 2007/0116839 A1 | 5/2007 | Prakash et al. |
| 2007/0116840 A1 | 5/2007 | Prakash et al. |
| 2007/0116841 A1 | 5/2007 | Prakash et al. |
| 2007/0117365 A1 | 5/2007 | Kuriyama |
| 2007/0124177 A1 | 5/2007 | Engleson et al. |
| 2007/0125230 A1 | 6/2007 | Powell et al. |
| 2007/0131254 A1 | 6/2007 | Kin |
| 2007/0132968 A1 | 6/2007 | Kobayashi et al. |
| 2007/0134390 A1 | 6/2007 | Prakash et al. |
| 2007/0134391 A1 | 6/2007 | Prakash et al. |
| 2007/0141974 A1 | 6/2007 | McNaughton et al. |
| 2007/0144565 A1 | 6/2007 | Lynn |
| 2007/0148305 A1 | 6/2007 | Sherwood et al. |
| 2007/0148307 A1 | 6/2007 | Sherwood et al. |
| 2007/0154364 A1 | 7/2007 | Tseng |
| 2007/0154614 A1 | 7/2007 | Sherwood et al. |
| 2007/0163935 A1* | 7/2007 | Chewins ............... A61M 27/00 422/292 |
| 2007/0169889 A1 | 7/2007 | Clark |
| 2007/0171390 A1 | 7/2007 | Hazelton |
| 2007/0178214 A1 | 8/2007 | Sherwood et al. |
| 2007/0186367 A1 | 8/2007 | Field et al. |
| 2007/0186368 A1 | 8/2007 | Field et al. |
| 2007/0186369 A1 | 8/2007 | Field et al. |
| 2007/0186954 A1 | 8/2007 | Field et al. |
| 2007/0186957 A1 | 8/2007 | Field et al. |
| 2007/0186958 A1 | 8/2007 | Field et al. |
| 2007/0187261 A1 | 8/2007 | Field et al. |
| 2007/0187262 A1 | 8/2007 | Field et al. |
| 2007/0187263 A1 | 8/2007 | Field et al. |
| 2007/0189949 A1 | 8/2007 | Hsieh et al. |
| 2007/0190469 A1 | 8/2007 | Clark |
| 2007/0190523 A1 | 8/2007 | Birkus et al. |
| 2007/0207923 A1 | 9/2007 | Lu |
| 2007/0207941 A1 | 9/2007 | Thonhauser |
| 2007/0210111 A1 | 9/2007 | Davis |
| 2007/0222599 A1 | 9/2007 | Coveley et al. |
| 2007/0235065 A1 | 10/2007 | Lin |
| 2007/0242247 A1 | 10/2007 | Shiraishi |
| 2007/0246564 A1 | 10/2007 | Rodenbeck et al. |
| 2007/0247316 A1 | 10/2007 | Wildman et al. |
| 2007/0247600 A1 | 10/2007 | Kobayashi et al. |
| 2007/0247601 A1 | 10/2007 | Hazelton |
| 2007/0251549 A1 | 11/2007 | Heiligenmann et al. |
| 2007/0253860 A1 | 11/2007 | Schroder |
| 2007/0253861 A1 | 11/2007 | Naka |
| 2007/0258072 A1 | 11/2007 | Nagasaka et al. |
| 2007/0264175 A1 | 11/2007 | Iversen |
| 2007/0264296 A1 | 11/2007 | Myntti |
| 2007/0264310 A1 | 11/2007 | Hissong et al. |
| 2007/0264342 A1 | 11/2007 | Oliver et al. |
| 2007/0264353 A1 | 11/2007 | Myntti et al. |
| 2007/0267334 A1 | 11/2007 | Osborn |
| 2007/0290177 A1 | 12/2007 | Singh et al. |
| 2007/0291239 A1 | 12/2007 | Shiraishi |
| 2007/0292559 A1 | 12/2007 | Garwood |
| 2007/0293640 A1 | 12/2007 | Jiang et al. |
| 2008/0001763 A1 | 1/2008 | Raja et al. |
| 2008/0002164 A1 | 1/2008 | Chang et al. |
| 2008/0014113 A1 | 1/2008 | Centanni |
| 2008/0017590 A1 | 1/2008 | Suchak et al. |
| 2008/0017613 A1 | 1/2008 | Nogami et al. |
| 2008/0021779 A1 | 1/2008 | Lynn et al. |
| 2008/0023411 A1 | 1/2008 | Liou |
| 2008/0030695 A1 | 2/2008 | Kobayashi et al. |
| 2008/0030696 A1 | 2/2008 | Kobayashi et al. |
| 2008/0035580 A1 | 2/2008 | de Rijk |

(56) References Cited

U.S. PATENT DOCUMENTS

| | | |
|---|---|---|
| 2008/0039176 A1 | 2/2008 | Okada |
| 2008/0050498 A1 | 2/2008 | Sherwood et al. |
| 2008/0066739 A1 | 3/2008 | LeMahieu |
| 2008/0066741 A1 | 3/2008 | LeMahieu |
| 2008/0067078 A1 | 3/2008 | Kitaori et al. |
| 2008/0073324 A1 | 3/2008 | Nogami |
| 2008/0078382 A1 | 4/2008 | LeMahieu |
| 2008/0081868 A1 | 4/2008 | Jiang et al. |
| 2008/0081878 A1 | 4/2008 | Jiang et al. |
| 2008/0087719 A1 | 4/2008 | Sahud |
| 2008/0093277 A1 | 4/2008 | Armour |
| 2008/0105764 A1 | 5/2008 | Jianglin et al. |
| 2008/0108710 A1 | 5/2008 | Prakash et al. |
| 2008/0121837 A1 | 5/2008 | Singh et al. |
| 2008/0142010 A1 | 6/2008 | Weaver |
| 2008/0157022 A1 | 7/2008 | Singh |
| 2008/0169290 A1 | 7/2008 | Mangiardi |
| 2008/0175777 A1 | 7/2008 | Suchak et al. |
| 2008/0179242 A1 | 7/2008 | Mukhopadhyay |
| 2008/0181832 A1 | 7/2008 | Shiue et al. |
| 2008/0189872 A9 | 8/2008 | Wright |
| 2008/0192483 A1 | 8/2008 | Mangiardi |
| 2008/0196334 A1 | 8/2008 | Mangiardi |
| 2008/0202994 A1 | 8/2008 | Hsu et al. |
| 2008/0203195 A1 | 8/2008 | Schmitt |
| 2008/0206415 A1 | 8/2008 | Sherwood |
| 2008/0209665 A1 | 9/2008 | Mangiardi |
| 2008/0210572 A1 | 9/2008 | Field |
| 2008/0212337 A1 | 9/2008 | Mangiardi |
| 2008/0214006 A1 | 9/2008 | Lee |
| 2008/0216241 A1 | 9/2008 | Davidson et al. |
| 2008/0216875 A1 | 9/2008 | Sharrock et al. |
| 2008/0225249 A1 | 9/2008 | Kobayashi et al. |
| 2008/0225250 A1 | 9/2008 | Kobayashi et al. |
| 2008/0230484 A1 | 9/2008 | Burnham et al. |
| 2008/0231825 A1 | 9/2008 | Kobayashi et al. |
| 2008/0236622 A1 | 10/2008 | Kim |
| 2008/0239260 A1 | 10/2008 | Shiraishi |
| 2008/0245092 A1 | 10/2008 | Forsberg |
| 2008/0245390 A1 | 10/2008 | Freer |
| 2008/0246599 A1 | 10/2008 | Hufton et al. |
| 2008/0251373 A1 | 10/2008 | Oke |
| 2008/0252865 A1 | 10/2008 | Nagasaka et al. |
| 2008/0260922 A1 | 10/2008 | Kirkpatrick et al. |
| 2008/0267840 A1 | 10/2008 | Yeh |
| 2008/0271238 A1 | 11/2008 | Reeder et al. |
| 2008/0287924 A1 | 11/2008 | Mangiardi |
| 2008/0296228 A1 | 12/2008 | Sauvignet et al. |
| 2008/0303658 A1 | 12/2008 | Melker et al. |
| 2008/0308763 A1 | 12/2008 | Singh et al. |
| 2008/0312125 A1 | 12/2008 | Kin et al. |
| 2008/0313799 A1 | 12/2008 | Nguyen |
| 2009/0011222 A1 | 1/2009 | Xiu |
| 2009/0017272 A1 | 1/2009 | Phillips et al. |
| 2009/0020016 A1 | 1/2009 | Christophersen |
| 2009/0026143 A1 | 1/2009 | Matsumura |
| 2009/0039032 A1 | 2/2009 | Patera et al. |
| 2009/0039176 A1 | 2/2009 | Davidson et al. |
| 2009/0051545 A1 | 2/2009 | Koblasz |
| 2009/0069475 A1 | 3/2009 | Jiang et al. |
| 2009/0071507 A1 | 3/2009 | Buschhardt |
| 2009/0081311 A1 | 3/2009 | Man et al. |
| 2009/0081317 A1 | 3/2009 | McNaughton et al. |
| 2009/0092556 A1 | 4/2009 | Singh et al. |
| 2009/0096615 A1 | 4/2009 | Reeder et al. |
| 2009/0099503 A1 | 4/2009 | Mitsuda |
| 2009/0110594 A1 | 4/2009 | Shin |
| 2009/0113619 A1 | 5/2009 | Tichenor et al. |
| 2009/0114605 A1 | 5/2009 | Salama et al. |
| 2009/0120473 A1 | 5/2009 | Lynn |
| 2009/0126763 A1 | 5/2009 | Park |
| 2009/0127128 A1 | 5/2009 | Kitaori |
| 2009/0133713 A1 | 5/2009 | Ohmi |
| 2009/0145463 A1 | 6/2009 | Oh |
| 2009/0149604 A1 | 6/2009 | Abhari et al. |
| 2009/0170852 A1 | 7/2009 | Choi |
| 2009/0189759 A1 | 7/2009 | Wildman et al. |
| 2009/0192231 A1 | 7/2009 | Lemons |
| 2009/0199872 A1 | 8/2009 | Kirkpatrick |
| 2009/0202396 A1 | 8/2009 | Long |
| 2009/0202661 A1 | 8/2009 | Kirkpatrick |
| 2009/0215658 A1 | 8/2009 | Minsek et al. |
| 2009/0218281 A1 | 9/2009 | Sauvignet |
| 2009/0223904 A1 | 9/2009 | Tanny |
| 2009/0225286 A1 | 9/2009 | Nagasaka et al. |
| 2009/0241807 A1 | 10/2009 | George et al. |
| 2009/0255299 A1 | 10/2009 | Hiro |
| 2009/0258086 A1 | 10/2009 | Myntti |
| 2009/0258160 A1 | 10/2009 | Kumazawa |
| 2009/0263548 A1 | 10/2009 | Sjoholm |
| 2009/0266383 A1 | 10/2009 | Wang |
| 2009/0269240 A1 | 10/2009 | Tanaka |
| 2009/0273103 A1 | 11/2009 | Watanabe |
| 2009/0278076 A1 | 11/2009 | Singh et al. |
| 2009/0283110 A1 | 11/2009 | Yoneda et al. |
| 2009/0284146 A1 | 11/2009 | Yoshida et al. |
| 2009/0285764 A1 | 11/2009 | Singh et al. |
| 2009/0301395 A1 | 12/2009 | Sekimoto |
| 2009/0301951 A1 | 12/2009 | Armour |
| 2009/0321365 A1 | 12/2009 | Eriksson |
| 2010/0001418 A1 | 1/2010 | Hirakui |
| 2010/0010422 A1 | 1/2010 | Watanabe |
| 2010/0018927 A1 | 1/2010 | Poole |
| 2010/0021513 A1 | 1/2010 | Garois |
| 2010/0021598 A1 | 1/2010 | Lynn |
| 2010/0029829 A9 | 2/2010 | Jiang et al. |
| 2010/0029851 A9 | 2/2010 | Jiang et al. |
| 2010/0056773 A1 | 3/2010 | Chandrasekhar |
| 2010/0065530 A1 | 3/2010 | Walker |
| 2010/0068109 A1 | 3/2010 | Comrie |
| 2010/0076128 A1 | 3/2010 | Abhari et al. |
| 2010/0012157 A1 | 4/2010 | Sellmer |
| 2010/0095715 A1 | 4/2010 | Ulger et al. |
| 2010/0100242 A1 | 4/2010 | Frank |
| 2010/0104988 A1 | 4/2010 | Hayasaki |
| 2010/0112677 A1 | 5/2010 | Onishi |
| 2010/0116369 A1 | 5/2010 | Lautzenheiser et al. |
| 2010/0117836 A1 | 5/2010 | Seyed Momen et al. |
| 2010/0119427 A1 | 5/2010 | Suchak |
| 2010/0119670 A1 | 5/2010 | Mazzariello |
| 2010/0127209 A1 | 5/2010 | Singh et al. |
| 2010/0134772 A1 | 6/2010 | Nagasaka et al. |
| 2010/0139691 A1 | 6/2010 | Silberberg et al. |
| 2010/0139709 A1 | 6/2010 | Saefkow et al. |
| 2010/0139779 A1 | 6/2010 | Lautzenheiser et al. |
| 2010/0139864 A1 | 6/2010 | Silberberg et al. |
| 2010/0143201 A1 | 6/2010 | Long |
| 2010/0155416 A1 | 6/2010 | Johnson |
| 2010/0164728 A1 | 7/2010 | Plost |
| 2010/0167973 A1 | 7/2010 | Thonhauser et al. |
| 2010/0170570 A1 | 7/2010 | Rodenbeck et al. |
| 2010/0179268 A9 | 7/2010 | Jiang et al. |
| 2010/0181260 A1 | 7/2010 | Vroom |
| 2010/0188228 A1 | 7/2010 | Hyland |
| 2010/0192987 A1 | 8/2010 | Steffen |
| 2010/0193977 A1 | 8/2010 | Yamamoto et al. |
| 2010/0195068 A1 | 8/2010 | Shibazaki |
| 2010/0209313 A1 | 8/2010 | Davis |
| 2010/0223944 A1 | 9/2010 | Tsujimoto |
| 2010/0224215 A1 | 9/2010 | Mertens |
| 2010/0224495 A1 | 9/2010 | McGuire |
| 2010/0231385 A1 | 9/2010 | Melker et al. |
| 2010/0236269 A1 | 9/2010 | Mamemoto |
| 2010/0243580 A1 | 9/2010 | Lobban |
| 2010/0252415 A1 | 10/2010 | Lynn |
| 2010/0258142 A1 | 10/2010 | Kawaguchi |
| 2010/0262430 A1 | 10/2010 | Gips et al. |
| 2010/0265059 A1 | 10/2010 | Melker et al. |
| 2010/0266445 A1 | 10/2010 | Campagna |
| 2010/0282773 A1 | 11/2010 | Lynn |
| 2010/0298738 A1 | 11/2010 | Felts et al. |
| 2010/0308037 A1 | 12/2010 | Mangiardi |
| 2010/0311573 A1 | 12/2010 | Mestl et al. |
| 2010/0315243 A1 | 12/2010 | Tokhtuev et al. |

(56) References Cited

U.S. PATENT DOCUMENTS

| | | |
|---|---|---|
| 2010/0315244 A1 | 12/2010 | Tokhtuev et al. |
| 2010/0326472 A1* | 12/2010 | Glenn .................... G16H 40/63 |
| | | 134/18 |
| 2010/0326476 A1 | 12/2010 | Rho |
| 2010/0328076 A1 | 12/2010 | Kyle et al. |
| 2010/0332022 A1 | 12/2010 | Wegelin et al. |
| 2011/0011886 A1 | 1/2011 | Zaima et al. |
| 2011/0016643 A1 | 1/2011 | DuVal |
| 2011/0030823 A1 | 2/2011 | Seal et al. |
| 2011/0036761 A1 | 2/2011 | Chen et al. |
| 2011/0037016 A1 | 2/2011 | Singh et al. |
| 2011/0046921 A1 | 2/2011 | Sahud |
| 2011/0048038 A1 | 3/2011 | Merritt |
| 2011/0048452 A1 | 3/2011 | Zink et al. |
| 2011/0060257 A1 | 3/2011 | Nakamura |
| 2011/0067730 A1 | 3/2011 | Folz et al. |
| 2011/0068060 A1 | 3/2011 | Hatten |
| 2011/0068930 A1 | 3/2011 | Wildman et al. |
| 2011/0074585 A1 | 3/2011 | Harmon et al. |
| 2011/0075119 A1 | 3/2011 | Ito |
| 2011/0075507 A1 | 3/2011 | Wootan |
| 2011/0076190 A1 | 3/2011 | Tanaka |
| 2011/0079519 A1 | 4/2011 | Widler et al. |
| 2011/0081299 A1 | 4/2011 | Thonhauser |
| 2011/0132749 A1 | 6/2011 | Field |
| 2011/0135548 A1 | 6/2011 | Comrie |
| 2011/0135847 A1 | 6/2011 | Phillips et al. |
| 2011/0136882 A1 | 6/2011 | McNaughton et al. |
| 2011/0140596 A1 | 6/2011 | Yoshida et al. |
| 2011/0150625 A1 | 6/2011 | Enkhbold |
| 2011/0152995 A1 | 6/2011 | Mader et al. |
| 2011/0174222 A1 | 7/2011 | Lee |
| 2011/0175351 A1 | 7/2011 | Baarman et al. |
| 2011/0178590 A1 | 7/2011 | Zucker |
| 2011/0186095 A1 | 8/2011 | Kim |
| 2011/0203620 A1 | 8/2011 | Ulger et al. |
| 2011/0207300 A1 | 8/2011 | Brown et al. |
| 2011/0208539 A1 | 8/2011 | Lynn |
| 2011/0209730 A1 | 9/2011 | Varrin, Jr. et al. |
| 2011/0212018 A1 | 9/2011 | Otero |
| 2011/0226292 A1 | 9/2011 | Ulger et al. |
| 2011/0227740 A1 | 9/2011 | Wohltjen |
| 2011/0252899 A1 | 10/2011 | Felts et al. |
| 2011/0256027 A1 | 10/2011 | Chen et al. |
| 2011/0274634 A1 | 11/2011 | Rieth et al. |
| 2011/0274643 A1 | 11/2011 | Yontz |
| 2011/0284476 A1 | 11/2011 | Otero |
| 2011/0289748 A1 | 12/2011 | Singh et al. |
| 2011/0291840 A1 | 12/2011 | Pelland et al. |
| 2011/0291841 A1 | 12/2011 | Hollock et al. |
| 2011/0297696 A1 | 12/2011 | Casares |
| 2011/0298376 A1 | 12/2011 | Kanegae |
| 2011/0300083 A1 | 12/2011 | Yontz et al. |
| 2011/0303247 A1 | 12/2011 | Varrin, Jr. et al. |
| 2012/0012134 A1 | 1/2012 | Tsukamoto |
| 2012/0013465 A1 | 1/2012 | Reeder et al. |
| 2012/0013470 A1 | 1/2012 | Lynn |
| 2012/0016215 A1 | 1/2012 | Condurso et al. |
| 2012/0018386 A1 | 1/2012 | McGuire |
| 2012/0024794 A1 | 2/2012 | Fischmann T. |
| 2012/0031838 A1 | 2/2012 | Noguchi et al. |
| 2012/0055557 A1* | 3/2012 | Belz ...................... E03C 1/057 |
| | | 137/1 |
| 2012/0055986 A1 | 3/2012 | Sahud |
| 2012/0067738 A1 | 3/2012 | Field |
| 2012/0077877 A1 | 3/2012 | Man et al. |
| 2012/0080451 A1 | 4/2012 | Williams et al. |
| 2012/0091888 A1 | 4/2012 | Yoshida et al. |
| 2012/0094881 A1 | 4/2012 | Thonhauser et al. |
| 2012/0095157 A1 | 4/2012 | Jiang et al. |
| 2012/0096768 A1 | 4/2012 | Johnson |
| 2012/0097201 A1 | 4/2012 | Field |
| 2012/0100701 A1 | 4/2012 | Kawasaki |
| 2012/0108917 A1 | 5/2012 | Libbus et al. |
| 2012/0121488 A1 | 5/2012 | Comrie |
| 2012/0138155 A1 | 6/2012 | Brensing et al. |
| 2012/0142575 A1 | 6/2012 | Lynn |
| 2012/0160660 A1 | 6/2012 | Karlstrom et al. |
| 2012/0167926 A1 | 7/2012 | Nakamura |
| 2012/0167997 A1 | 7/2012 | Brensing et al. |
| 2012/0177803 A1 | 7/2012 | Xu |
| 2012/0179491 A1 | 7/2012 | Liu et al. |
| 2012/0187331 A1 | 7/2012 | Singh et al. |
| 2012/0194338 A1 | 8/2012 | Snodgrass |
| 2012/0198870 A1 | 8/2012 | Erbs |
| 2012/0204594 A1 | 8/2012 | Singh et al. |
| 2012/0205301 A1 | 8/2012 | McGuire |
| 2012/0207664 A1 | 8/2012 | Moore |
| 2012/0207665 A1 | 8/2012 | Moore |
| 2012/0208375 A1 | 8/2012 | Ohmi |
| 2012/0216828 A1 | 8/2012 | Tanaka |
| 2012/0218106 A1 | 8/2012 | Zaima et al. |
| 2012/0225171 A1 | 9/2012 | Garwood |
| 2012/0227586 A1 | 9/2012 | Chan et al. |
| 2012/0228149 A1 | 9/2012 | Boal |
| 2012/0230880 A1 | 9/2012 | Dunkley et al. |
| 2012/0240964 A1 | 9/2012 | Kirkpatrick |
| 2012/0251681 A1 | 10/2012 | Zacharias |
| 2012/0263800 A1 | 10/2012 | Berentsveig et al. |
| 2012/0267295 A1 | 10/2012 | Kim |
| 2012/0279498 A1 | 11/2012 | Nakamura |
| 2012/0285825 A1 | 11/2012 | Benedetto |
| 2012/0303385 A1 | 11/2012 | Darling |
| 2012/0319836 A1 | 12/2012 | Reeder et al. |
| 2012/0330118 A1 | 12/2012 | Lynn et al. |
| 2013/0008870 A1 | 1/2013 | Nogami et al. |
| 2013/0011303 A1 | 1/2013 | Shim |
| 2013/0011520 A1 | 1/2013 | Wang |
| 2013/0014362 A1 | 1/2013 | Bilgen et al. |
| 2013/0019348 A1 | 1/2013 | Crouse et al. |
| 2013/0025714 A1 | 1/2013 | Hermann |
| 2013/0031872 A1 | 2/2013 | Blaiss et al. |
| 2013/0034966 A1 | 2/2013 | Yeh |
| 2013/0041241 A1 | 2/2013 | Felts et al. |
| 2013/0047655 A1 | 2/2013 | White |
| 2013/0061884 A1 | 3/2013 | Yang |
| 2013/0068260 A1 | 3/2013 | Yamakawa |
| 2013/0068701 A1 | 3/2013 | Bain |
| 2013/0070786 A1 | 3/2013 | Liu |
| 2013/0089677 A1 | 4/2013 | Makover |
| 2013/0096444 A1 | 4/2013 | Condurso et al. |
| 2013/0120120 A1 | 5/2013 | Long et al. |
| 2013/0120142 A1 | 5/2013 | Wildman et al. |
| 2013/0121892 A1 | 5/2013 | Furhmann et al. |
| 2013/0130331 A1 | 5/2013 | Binder |
| 2013/0136669 A1 | 5/2013 | Feldain |
| 2013/0140242 A1 | 6/2013 | De Oliveira |
| 2013/0150531 A1 | 6/2013 | Abhari et al. |
| 2013/0169945 A1 | 7/2013 | Kobayashi et al. |
| 2013/0172417 A1 | 7/2013 | Man et al. |
| 2013/0186465 A1 | 7/2013 | Zhou |
| 2013/0204433 A1 | 8/2013 | Gupta et al. |
| 2013/0206654 A1* | 8/2013 | Lutz ...................... C02F 1/4672 |
| | | 210/88 |
| 2013/0213899 A1 | 8/2013 | Fahs |
| 2013/0216432 A1 | 8/2013 | Lemons |
| 2013/0217784 A1 | 8/2013 | Singh et al. |
| 2013/0228176 A1 | 9/2013 | Nakamura |
| 2013/0233357 A1 | 9/2013 | Minamihonoki |
| 2013/0240344 A1 | 9/2013 | Johnson |
| 2013/0244320 A1 | 9/2013 | Morgan |
| 2013/0247835 A1 | 9/2013 | Liimatta |
| 2013/0260058 A1 | 10/2013 | Brown et al. |
| 2013/0269518 A1 | 10/2013 | Ilmasti |
| 2013/0269733 A1 | 10/2013 | Chakrabortty |
| 2013/0284217 A1 | 10/2013 | Freer |
| 2013/0284219 A1 | 10/2013 | Yoneda et al. |
| 2013/0285814 A1 | 10/2013 | Snodgrass |
| 2013/0287637 A1 | 10/2013 | Vickery |
| 2013/0288947 A1 | 10/2013 | Huboux et al. |
| 2013/0291632 A1 | 11/2013 | Felts et al. |
| 2013/0299608 A1 | 11/2013 | Spangler et al. |
| 2013/0300558 A1 | 11/2013 | Reeder et al. |
| 2013/0306532 A1 | 11/2013 | Fischmann T. |

(56) References Cited

U.S. PATENT DOCUMENTS

| | | |
|---|---|---|
| 2013/0306573 A1 | 11/2013 | Appelbaum |
| 2013/0335717 A1 | 12/2013 | Shiraishi |
| 2013/0337226 A1 | 12/2013 | Curran et al. |
| 2013/0344201 A1 | 12/2013 | Sherwood |
| 2014/0017364 A1 | 1/2014 | Liimatta |
| 2014/0022079 A1 | 1/2014 | Wilson |
| 2014/0034088 A1 | 2/2014 | Padtberg et al. |
| 2014/0035744 A1 | 2/2014 | Wildman et al. |
| 2014/0048719 A1 | 2/2014 | Johnson |
| 2014/0059789 A1 | 3/2014 | Freer |
| 2014/0066567 A1 | 3/2014 | Jiang et al. |
| 2014/0070950 A1 | 3/2014 | Snodgrass |
| 2014/0077124 A1 | 3/2014 | Singh et al. |
| 2014/0080974 A1 | 3/2014 | Jiang et al. |
| 2014/0081654 A1 | 3/2014 | Bechtel et al. |
| 2014/0088014 A1 | 3/2014 | Nishio |
| 2014/0090606 A1 | 4/2014 | Heacox |
| 2014/0100516 A1 | 4/2014 | Hunt |
| 2014/0100868 A1 | 4/2014 | Condurso et al. |
| 2014/0107242 A1 | 4/2014 | Singh et al. |
| 2014/0108041 A1 | 4/2014 | Bechtel et al. |
| 2014/0121316 A1 | 5/2014 | Monsallier et al. |
| 2014/0127107 A1 | 5/2014 | Suchak |
| 2014/0140913 A1 | 5/2014 | Suchak |
| 2014/0158167 A1 | 6/2014 | de Larios |
| 2014/0166588 A1 | 6/2014 | Fischmann |
| 2014/0178312 A1 | 6/2014 | Basu |
| 2014/0191019 A1 | 7/2014 | Chen et al. |
| 2014/0202182 A1 | 7/2014 | Singh et al. |
| 2014/0212334 A1 | 7/2014 | Klein et al. |
| 2014/0213845 A1 | 7/2014 | Bechtel et al. |
| 2014/0216075 A1 | 8/2014 | Singh et al. |
| 2014/0216499 A1 | 8/2014 | Li |
| 2014/0227405 A1 | 8/2014 | Beland |
| 2014/0286831 A1 | 9/2014 | Moore |
| 2014/0292518 A1 | 10/2014 | Wildman et al. |
| 2014/0293249 A1 | 10/2014 | Kobayashi et al. |
| 2014/0294744 A1 | 10/2014 | Rieth et al. |
| 2014/0295053 A1 | 10/2014 | Felts et al. |
| 2014/0296350 A1 | 10/2014 | DeMattei et al. |
| 2014/0297313 A1 | 10/2014 | Condurso et al. |
| 2014/0297327 A1 | 10/2014 | Heil et al. |
| 2014/0299552 A1 | 10/2014 | Stewart |
| 2014/0320290 A1 | 10/2014 | Reeder et al. |
| 2014/0320291 A1 | 10/2014 | De Luca et al. |
| 2014/0322089 A1 | 10/2014 | Moore |
| 2014/0322096 A1 | 10/2014 | Pelfrey |
| 2014/0322407 A1 | 10/2014 | Man et al. |
| 2014/0327545 A1 | 11/2014 | Bolling et al. |
| 2014/0329223 A1 | 11/2014 | Morgan |
| 2014/0347185 A1 | 11/2014 | Smith et al. |
| 2014/0352799 A1 | 12/2014 | Rosko et al. |
| 2014/0353256 A1 | 12/2014 | Kaschek |
| 2014/0354436 A1 | 12/2014 | Nix et al. |
| 2014/0361897 A1 | 12/2014 | Smith et al. |
| 2014/0367417 A1 | 12/2014 | Zaima et al. |
| 2014/0375457 A1 | 12/2014 | Diaz |
| 2015/0000704 A1 | 1/2015 | Yeh |
| 2015/0015417 A1 | 1/2015 | Libbus et al. |
| 2015/0017059 A1 | 1/2015 | Arlemark |
| 2015/0017432 A1 | 1/2015 | Shoseyov |
| 2015/0022361 A1 | 1/2015 | Gaisser et al. |
| 2015/0033295 A1 | 1/2015 | Huster |
| 2015/0044116 A1 | 2/2015 | Suschak |
| 2015/0048160 A1 | 2/2015 | Graydon |
| 2015/0057635 A1 | 2/2015 | Bechtel et al. |
| 2015/0059085 A1 | 3/2015 | Seibt |
| 2015/0064124 A1 | 3/2015 | Yontz et al. |
| 2015/0081335 A1 | 3/2015 | Dixon et al. |
| 2015/0099008 A1 | 4/2015 | Curry |
| 2015/0111284 A1 | 4/2015 | Urbini |
| 2015/0114819 A1 | 4/2015 | Denton |
| 2015/0121628 A1 | 5/2015 | McCullough |
| 2015/0125212 A1 | 5/2015 | Fischmann |
| 2015/0126941 A1 | 5/2015 | Felts et al. |
| 2015/0127365 A1 | 5/2015 | Rizvi et al. |
| 2015/0128993 A1 | 5/2015 | Berg et al. |
| 2015/0136346 A1 | 5/2015 | Bogren |
| 2015/0136666 A1 | 5/2015 | Zamir |
| 2015/0136709 A1 | 5/2015 | Kolstad |
| 2015/0140621 A1 | 5/2015 | Herrema |
| 2015/0144831 A1 | 5/2015 | Mennell |
| 2015/0152352 A1 | 6/2015 | Huboux et al. |
| 2015/0157754 A1 | 6/2015 | Rutter |
| 2015/0158055 A1 | 6/2015 | Kirkpatrick |
| 2015/0182649 A1 | 7/2015 | Dunkley et al. |
| 2015/0183673 A1 | 7/2015 | Musale |
| 2015/0194043 A1 | 7/2015 | Dunn et al. |
| 2015/0197514 A1 | 7/2015 | Crouse et al. |
| 2015/0203360 A1 | 7/2015 | Johnston et al. |
| 2015/0208591 A1 | 7/2015 | Steffen |
| 2015/0213202 A1 | 7/2015 | Amarasingham et al. |
| 2015/0213205 A1 | 7/2015 | Van De Sluis et al. |
| 2015/0213206 A1 | 7/2015 | Amarasingham et al. |
| 2015/0213217 A1 | 7/2015 | Amarasingham et al. |
| 2015/0213222 A1 | 7/2015 | Amarasingham et al. |
| 2015/0213223 A1 | 7/2015 | Amarasingham et al. |
| 2015/0213224 A1 | 7/2015 | Amarasingham et al. |
| 2015/0213225 A1 | 7/2015 | Amarasingham et al. |
| 2015/0221208 A1 | 8/2015 | Knighton et al. |
| 2015/0227705 A1 | 8/2015 | Zaima et al. |
| 2015/0231288 A1 | 8/2015 | Campagna |
| 2015/0232353 A1 | 8/2015 | Denvir |
| 2015/0233022 A1 | 8/2015 | McCullough |
| 2015/0235549 A1 | 8/2015 | Limbert |
| 2015/0235550 A1 | 8/2015 | Pelland et al. |
| 2015/0251921 A1 | 9/2015 | Sobanski |
| 2015/0254964 A1 | 9/2015 | Raichman et al. |
| 2015/0273408 A1 | 10/2015 | Tachibana et al. |
| 2015/0297771 A1 | 10/2015 | Law |
| 2015/0302150 A1 | 10/2015 | Mazar et al. |
| 2015/0302538 A1 | 10/2015 | Mazar et al. |
| 2015/0302539 A1 | 10/2015 | Mazar et al. |
| 2015/0310180 A1 | 10/2015 | Pattekar et al. |
| 2015/0321279 A1 | 11/2015 | Chen et al. |
| 2015/0322540 A1 | 11/2015 | Chen et al. |
| 2015/0322545 A1 | 11/2015 | Chen et al. |
| 2015/0330007 A1 | 11/2015 | Blaiss et al. |
| 2015/0332007 A1 | 11/2015 | Rosebraugh |
| 2015/0332940 A1 | 11/2015 | Wang et al. |
| 2015/0335037 A1 | 11/2015 | Coufal et al. |
| 2015/0343379 A1 | 12/2015 | Tomimatsu et al. |
| 2015/0352486 A1 | 12/2015 | Xu et al. |
| 2015/0361457 A1 | 12/2015 | Medoff et al. |
| 2015/0368137 A1 | 12/2015 | Miller |
| 2015/0368684 A1 | 12/2015 | Medoff et al. |
| 2015/0373954 A1 | 12/2015 | Kuo |
| 2016/0003564 A1 | 1/2016 | Theberge |
| 2016/0005300 A1 | 1/2016 | Laufer et al. |
| 2016/0008769 A1 | 1/2016 | Dubois et al. |
| 2016/0009581 A1 | 1/2016 | Gordon |
| 2016/0017231 A1 | 1/2016 | Singh et al. |
| 2016/0019666 A1 | 1/2016 | Amarasingham et al. |
| 2016/0021903 A1 | 1/2016 | Dull |
| 2016/0023934 A1 | 1/2016 | Smith et al. |
| 2016/0030883 A1 | 2/2016 | Xu et al. |
| 2016/0042634 A1 | 2/2016 | Alhazme |
| 2016/0042635 A1 | 2/2016 | Rosebraugh et al. |
| 2016/0066572 A1 | 3/2016 | Mathieu et al. |
| 2016/0073646 A1 | 3/2016 | Riley |
| 2016/0074436 A1 | 3/2016 | O'Flaherty et al. |
| 2016/0076155 A1 | 3/2016 | Kim |
| 2016/0088846 A1 | 3/2016 | Lemons |
| 2016/0089463 A1 | 3/2016 | Thorn |
| 2016/0093194 A1 | 3/2016 | Herzog |
| 2016/0125723 A1 | 5/2016 | Marra et al. |
| 2016/0137924 A1 | 5/2016 | Mazanec |
| 2016/0140832 A1 | 5/2016 | Moore |
| 2016/0148489 A1 | 5/2016 | Reeder et al. |
| 2016/0151015 A1 | 6/2016 | Condurso et al. |
| 2016/0160053 A1 | 6/2016 | Thevasahayam |
| 2016/0171874 A1 | 6/2016 | Hermann |
| 2016/0177550 A1 | 6/2016 | Sawaski |
| 2016/0180695 A1 | 6/2016 | Levchenko et al. |

(56) References Cited

U.S. PATENT DOCUMENTS

| | | | |
|---|---|---|---|
| 2016/0183525 A1 | 6/2016 | Curry | |
| 2016/0184791 A1 | 6/2016 | Appelbaum | |
| 2016/0194224 A1 | 7/2016 | Buchanan | |
| 2016/0194584 A1 | 7/2016 | Ngantung | |
| 2016/0197564 A1 | 7/2016 | Buchanan | |
| 2016/0216612 A1 | 7/2016 | Kobayashi et al. | |
| 2016/0220714 A1 | 8/2016 | Weltmann | |
| 2016/0250439 A1 | 9/2016 | Klein et al. | |
| 2016/0253897 A1 | 9/2016 | Wildman et al. | |
| 2016/0295860 A1 | 10/2016 | Dagher et al. | |
| 2016/0318780 A9 | 11/2016 | Bain | |
| 2016/0340487 A1 | 11/2016 | Singh et al. | |
| 2016/0362322 A1 | 12/2016 | Kuo | |
| 2017/0004972 A1 | 1/2017 | Suen | |
| 2017/0014803 A1 | 1/2017 | Sidheswaran | |
| 2017/0021302 A1 | 1/2017 | Galbraith | |
| 2017/0032657 A1 | 2/2017 | Gaisser et al. | |
| 2017/0049713 A1 | 2/2017 | Hille et al. | |
| 2017/0066953 A1 | 3/2017 | Hulse | |
| 2017/0086456 A1 | 3/2017 | Man et al. | |
| 2017/0089004 A1 | 3/2017 | Youn | |
| 2017/0121902 A1 | 5/2017 | Youn | |
| 2017/0135619 A1 | 5/2017 | Felts et al. | |
| 2017/0137953 A1 | 5/2017 | Jonte et al. | |
| 2017/0139333 A1 | 5/2017 | Dierichs | |
| 2017/0191237 A1 | 7/2017 | Fishmann Torres | |
| 2017/0197856 A1 | 7/2017 | Kolstad | |
| 2017/0206771 A1 | 7/2017 | Hermann | |
| 2017/0229003 A1 | 8/2017 | Borke et al. | |
| 2017/0233623 A1 | 8/2017 | Singh et al. | |
| 2017/0233624 A1 | 8/2017 | Thomas et al. | |
| 2017/0235238 A1 | 8/2017 | Shiraishi | |
| 2018/0171491 A1 | 6/2018 | Jonte et al. | |
| 2020/0263312 A1 | 8/2020 | Jonte et al. | |

FOREIGN PATENT DOCUMENTS

| | | |
|---|---|---|
| CN | 1675435 | 9/2005 |
| CN | 1809655 A | 7/2006 |
| CN | 101137797 | 3/2008 |
| CN | 101448744 | 6/2009 |
| CN | 101509576 | 8/2009 |
| CN | 103328690 | 9/2013 |
| CN | 103874786 A | 6/2014 |
| CN | 103987664 | 8/2014 |
| CN | 104159852 A | 11/2014 |
| EP | 0 544 744 | 6/1991 |
| EP | 1841924 | 10/2007 |
| EP | 3002695 | 4/2016 |
| GB | 2458118 | 9/2009 |
| GB | 2492912 | 1/2013 |
| JP | 6306666 A | 11/1994 |
| JP | 7060265 | 3/1995 |
| JP | 7290073 | 11/1995 |
| JP | 8071566 | 3/1996 |
| JP | 8108017 | 4/1996 |
| JP | 8281281 | 10/1996 |
| JP | 9075958 | 3/1997 |
| JP | 10005148 | 1/1998 |
| JP | 10219786 | 8/1998 |
| JP | 10328274 | 12/1998 |
| JP | 11009481 | 1/1999 |
| JP | 11021960 | 1/1999 |
| JP | 11036394 | 2/1999 |
| JP | 11047773 | 2/1999 |
| JP | 11047774 | 2/1999 |
| JP | 11140929 | 5/1999 |
| JP | 11157808 | 6/1999 |
| JP | 11236692 | 8/1999 |
| JP | 11247258 | 9/1999 |
| JP | 2000197891 | 7/2000 |
| JP | 2000317474 | 11/2000 |
| JP | 2001040731 | 2/2001 |
| JP | 2001070770 | 3/2001 |
| JP | 2001205059 | 7/2001 |
| JP | 2001276666 | 10/2001 |
| JP | 2002052327 | 2/2002 |
| JP | 2002126481 | 5/2002 |
| JP | 2002331233 | 11/2002 |
| JP | 2003135944 | 5/2003 |
| JP | 2003247255 | 9/2003 |
| JP | 2003320278 | 11/2003 |
| JP | 2004084445 | 3/2004 |
| JP | 2004324190 | 11/2004 |
| JP | 2005021718 | 1/2005 |
| JP | 2005124797 | 5/2005 |
| JP | 2005131489 | 5/2005 |
| JP | 2005169297 | 6/2005 |
| JP | 2006136862 | 6/2006 |
| JP | 2007111689 | 5/2007 |
| JP | 2007236706 | 9/2007 |
| JP | 2008000666 | 1/2008 |
| JP | 2008018327 | 1/2008 |
| JP | 2008086960 | 4/2008 |
| JP | 2008229491 | 10/2008 |
| JP | 2009189279 | 8/2009 |
| JP | 2009209378 | 9/2009 |
| JP | 2010090586 | 4/2010 |
| JP | 2010150630 | 7/2010 |
| JP | 2011004990 | 1/2011 |
| KR | 199614038 | 10/1996 |
| KR | 2009027908 | 3/2009 |
| KR | 2009030783 | 3/2009 |
| KR | 20090086962 | 8/2009 |
| KR | 1026415 | 4/2011 |
| TW | 200516060 | 5/2005 |
| WO | WO 98/16473 | 4/1998 |
| WO | WO 00/35813 | 6/2000 |
| WO | WO 03/040032 | 5/2003 |
| WO | WO 03/068375 | 8/2003 |
| WO | WO 2003033402 | 11/2003 |
| WO | WO 2004/033376 | 4/2004 |
| WO | WO 2006/076149 | 7/2006 |
| WO | WO 2008/044262 | 4/2008 |
| WO | WO 2009028845 | 3/2009 |
| WO | WO 2011/144285 | 11/2011 |
| WO | WO2012076521 | 6/2012 |
| WO | WO 2013/086217 | 6/2013 |
| WO | WO2014098861 | 6/2014 |
| WO | WO2015055971 | 4/2015 |
| WO | WO2015166406 | 11/2015 |
| WO | WO2016037290 | 3/2016 |
| WO | WO 2016/112922 | 7/2016 |
| WO | WO2016112922 | 7/2016 |
| WO | WO 2017/011506 | 1/2017 |

OTHER PUBLICATIONS

US 7,959,789 B2, 06/2011, Field et al. (withdrawn)
US 8,773,268 B2, 07/2014, Wildman et al. (withdrawn)
US 7,959,787, 09/2017, Oomen et al. (withdrawn).
Scan Unic ApS, CVR-nr. 30 27 94 17, Årsrapporten er godkendt på den ordinaere generalforsamling, d. 19.12.12; Årsrapport for Dec. 2011; 17 pages.
Project-market maturity fund, Market maturation Foundation gives enterprises new products to market faster, "Scan Unic-combat hospital infections", 2016; 2 pages.
International Search Report and Written Opinion, International Application No. PCT/US2012/068283, dated Apr. 13, 2017, 12 pgs.
International Preliminary Report on Patentability received for PCT Patent Application No. PCT/US2016/068081, dated Jul. 5, 2018, 9 pages.
International Search Report and Written Opinion received for PCT Patent Application No. PCT/US2016/068081, dated Apr. 13, 2017, 11 pages.
Ozone Generator, www.alibaba.com/product-gs/267935887/small_ozone_generator_water_sterilizer_w, Jun. 11, 2012.
Ozone Boy, www.cleanwaterstore.com/OS001630-p-ozone-faucet.html; Jun. 11, 2012.

(56) References Cited

OTHER PUBLICATIONS

Medi-Flo$_3$ Sink, available at www.franke-commercial.com, available at least as early as Nov. 27, 2015, 1 page.

* cited by examiner

FLUID DELIVERY SYSTEM INCLUDING A DISINFECTANT DEVICE

CROSS-REFERENCE TO RELATED APPLICATION

The present application is a U.S. 371 national phase filing of PCT International Application No. PCT/US2016/068081, filed Dec. 21, 2016, which claims priority to U.S. Provisional Patent Application Ser. No. 62/270,395, filed Dec. 21, 2015, the disclosures of which are expressly incorporated herein by reference.

BACKGROUND AND SUMMARY OF THE DISCLOSURE

The present invention relates generally to an electronic faucet and, more particularly, to an electronic faucet including a water treatment device.

Fluid delivery devices, such as faucets, may include a fluid treatment device. For example, a treatment device may include a filter, an ozone device, and/or a water softener configured to treat the water before it flows from the faucet. A user input may be provided for controlled use of the fluid treatment device.

In one illustrative embodiment of the present disclosure, the treatment device may include a disinfectant device, such as an antibacterial device to inactivate bacteria and/or viruses that may be present in the fluid. The faucet may be used in a corporate, industrial, medical, and/or residential building to promote hand hygiene among those in the building. In this way, the faucet may be configured to provide feedback to the user or a monitoring system regarding each person's compliance with hand hygiene protocols based on the person's usage of the faucet. The faucet also may be configured to collect and report such usage and/or compliance information to the user and/or a monitoring system. In one illustrative embodiment, the faucet includes capacitive sensing technology to determine if a user's hands are within the flow stream of the faucet and can automatically turn the fluid and the fluid treatment device on and off, based on a user's presence near the faucet.

According to an illustrative embodiment of the present disclosure, a faucet includes a spout having a waterway defining an outlet, at least one valve in fluid communication with the waterway of the spout, a controller in communication with the at least one valve, and a disinfectant device fluidly coupled to the waterway of the spout. The faucet is configured to selectively flow fluid through the disinfectant device in response to an input to the controller. Illustratively, the disinfectant device may comprise an antibacterial device, such as an electrolytic ozone generator.

According to a further illustrative embodiment of the present disclosure, a water treatment dispensing system includes an outer housing defining a chamber, a first fluid device supported by the outer housing and fluidly coupled to a tap water source for delivering tap water to the hands of a user received within the chamber, and a second fluid device supported by the outer housing and fluidly coupled to an ozone generator for delivering ozonated water to the hands of a user received within the chamber. The second fluid device illustratively includes a fluidic chip configured to produce a fan of water within a plane by oscillating water about a center axis.

In another illustrative embodiment, a water treatment dispensing system includes an outer housing defining a chamber, and a plurality of fluid devices supported by the outer housing. An ozone generator is fluidly coupled to the fluid devices for delivering ozonated water to the hands of a user received within the chamber. An electrically operable valve is in fluid communication with the ozone generator for controlling fluid flow therethrough. A controller is in electrical communication with the electrically operable valve. A user detector is in electrical communication with the controller, wherein the controller controls the electrically operably valve in response to the user detector detecting the hands of a user within the chamber. A gas mitigation system in electrical communication with the controller and includes a fan configured to draw ozone outgas from within the chamber.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The detailed description of the drawings particularly refers to the accompanying figures in which.

DETAILED DESCRIPTION OF THE DRAWINGS

The embodiments of the invention described herein are not intended to be exhaustive or to limit the invention to precise forms disclosed. Rather, the embodiments selected for description have been chosen to enable one skilled in the art to practice the invention. Although the disclosure is described in connection with water, it should be understood that additional types of fluids may be used.

Water Treatment Faucet

Figure 1A:
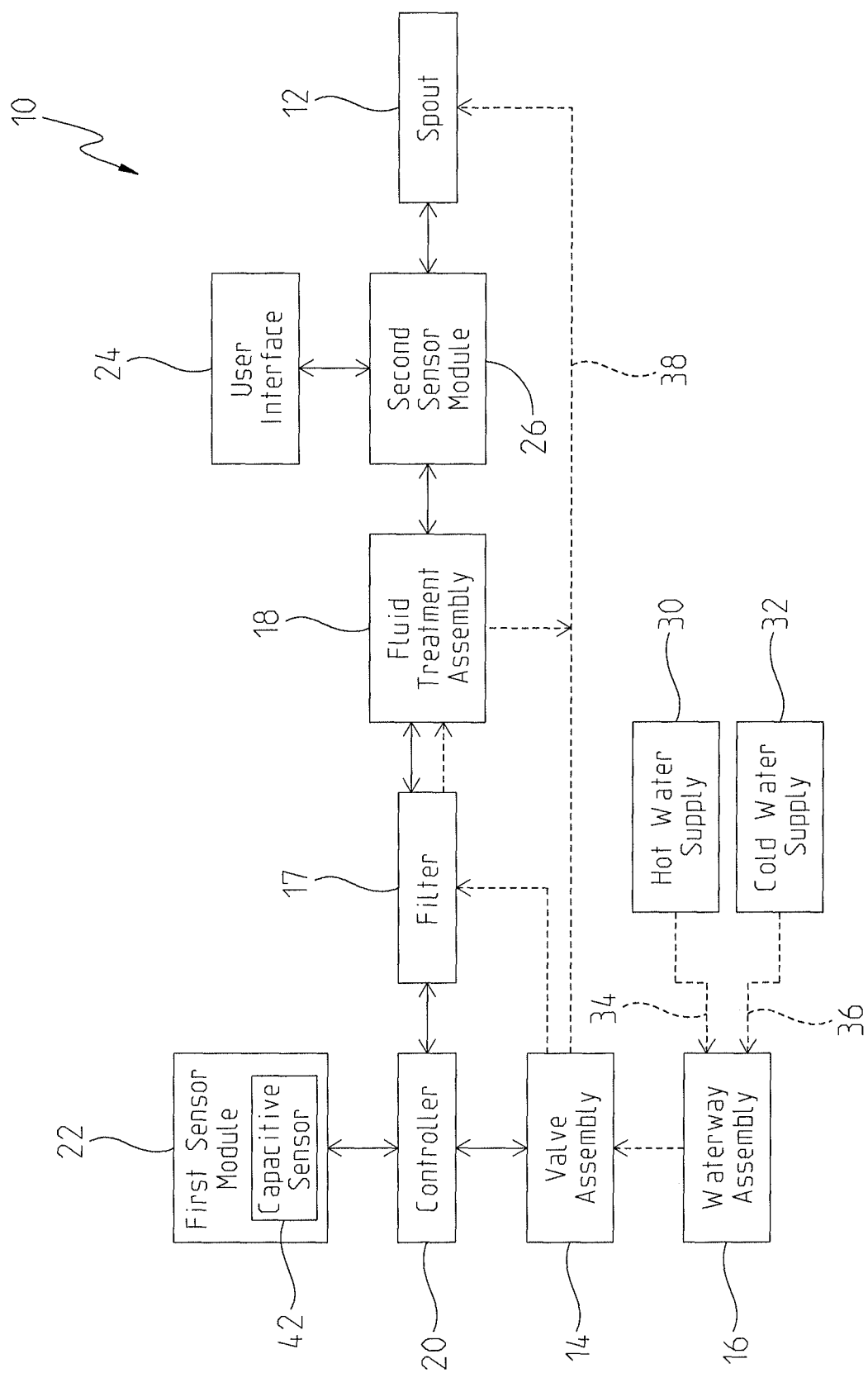
FIG. 1A is a block diagram of an illustrative faucet of the present disclosure.

Referring initially to FIG. 1A, an illustrative embodiment water treatment fluid delivery device in the form of a faucet 10 is shown as including a delivery spout 12, a valve assembly 14, a waterway assembly 16, a filter 17, a fluid treatment assembly 18, a controller 20, a first sensor module 22, a user interface 24, and a second sensor module 26. Faucet 10 also may include a badge or identification (ID) reader 28 (FIG. 2), as disclosed further herein. In operation, valve assembly 14 of faucet 10 receives water from hot and/or cold water supplies 30 and 32 (e.g., conventional water stops) through input lines or tubes 34 and 36, and selectively mixes the incoming water to provide water to spout 12 through an outlet line or tube 38. Outlet tube 38 defines an outlet 39 supported by spout 12. In FIG. 1, hidden connector lines represent illustrative fluid flow paths, while solid connector lines represent illustrative electrical signal paths.

Faucet 10 may be mounted to a sink deck 40 or other suitable surface with spout 12 positioned to direct water from outlet 39 into a conventional sink basin or other area, for example. User interface 24 may be supported on spout 12 or adjacent thereto (e.g., on sink deck 40).

Spout 12 is illustratively coupled to a capacitive sensor 42 which is illustratively part of first sensor module 22 and is electrically coupled to controller 20. At least a portion of the spout 12 is illustratively formed of a metal defining an electrode electrically coupled to the capacitive sensor 42. The capacitive sensor 42 senses a change in its capacitive field caused by a human body. For example, the capacitive field may change when a user touches, grabs, or comes within a predetermined proximity to spout 12 (e.g., 1-5 inches). When a change is sensed that indicates the presence of a user near faucet 10, controller 20 may automatically activate valve assembly 14 to supply water to spout 12. Conversely, when the user is no longer near faucet 10, controller 20 may send a signal to valve assembly 14 to stop the flow of water to spout 12.

Figure 1B:
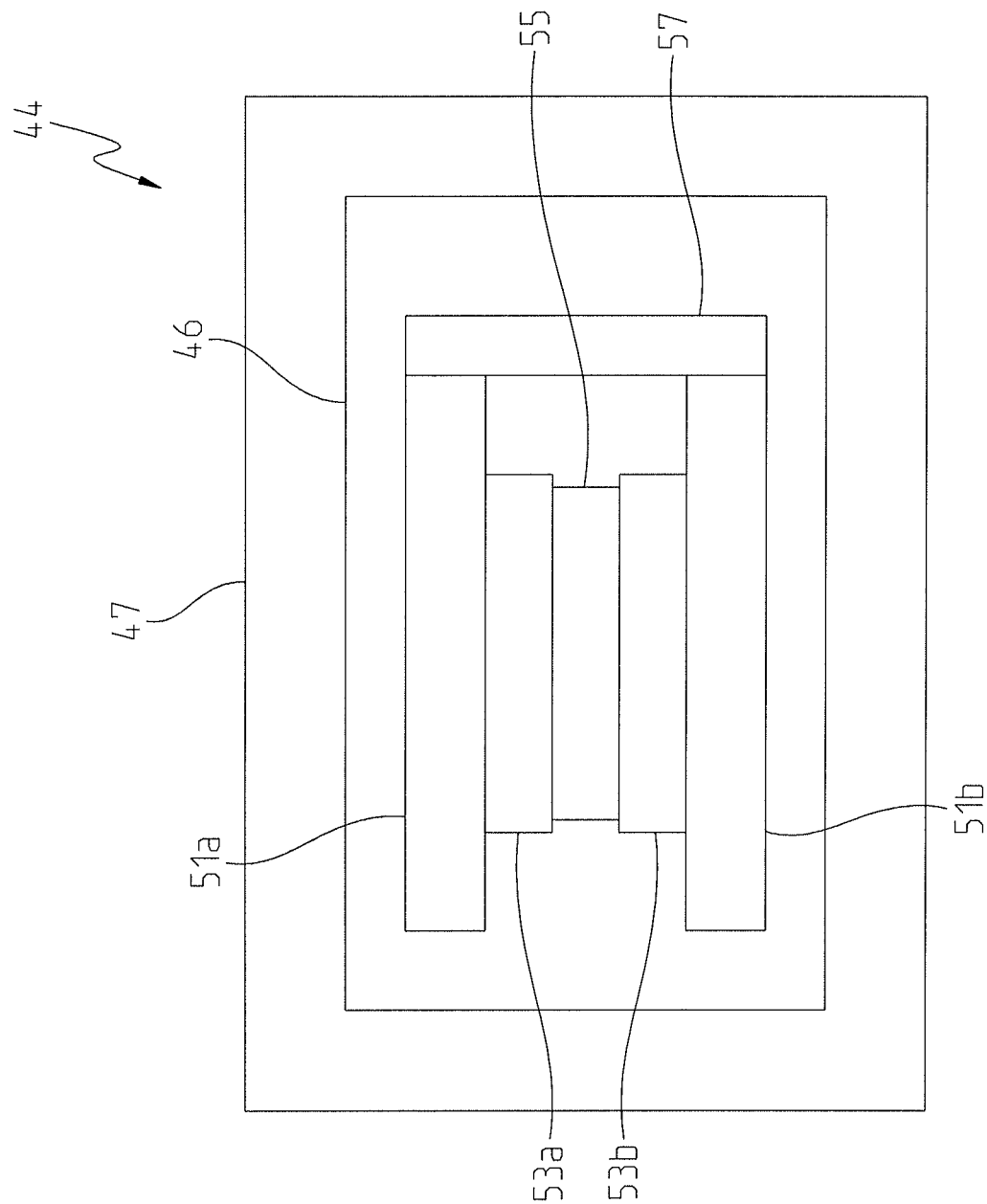
FIG. 1B is a diagrammatic view of an illustrative ozone device for use in the illustrative faucet of FIG. 1A.

With reference to FIGS. 1A and 1B, the fluid treatment assembly 18 illustratively includes a water treatment device and, more particularly, a disinfectant device such as an antibacterial device. As further detailed herein, the antibacterial device 18 may include an ozone device 44 having an electrolytic ozone generator or cell 46. More particularly, the ozone generator may include an outer cartridge 47 and an electrolytic cell assembly 46 received within the outer cartridge 47. The electrolytic cell assembly 46 illustratively includes a first housing 51a, an anode 53a coupled to the first housing 51a, a second housing 51b, a cathode 53b coupled to the second housing 51b, a separator 55 positioned between the anode 53a and the cathode 53b, and a holder 57 that couples the first housing 51a to the second housing 51b independently of the outer cartridge 47. Illustrative ozone generators are further detailed in U.S. Patent Application Ser. No. 62/191,741, filed Jul. 13, 2015, entitled "ELECTRODE FOR AN OZONE GENERATOR", now U.S. Pat. No. 10,767,270 and U.S. Patent Application Ser. No. 62/254,667, filed Nov. 12, 2015, entitled "OZONE GENERATOR FOR A FAUCET", now U.S. Pat. Nos. 10,640,878 and 11,220,754, the complete disclosures of which are expressly incorporated by reference herein.

Sensor modules 22, 26 may include a plurality of sensors, such as flow rate sensors, pressure sensors, temperature sensors, ozone concentration sensors, current sensors, voltage sensors, capacitive sensors, and any other sensor that may be used with faucet 10 and supply information to controller 20. While the following description references oxidation-reduction potential sensors (ORP) as the illustrative ozone concentration sensors, it should be appreciated that other known sensors may be substituted therefor, including polarographic oxygen sensors.

Figure 4:
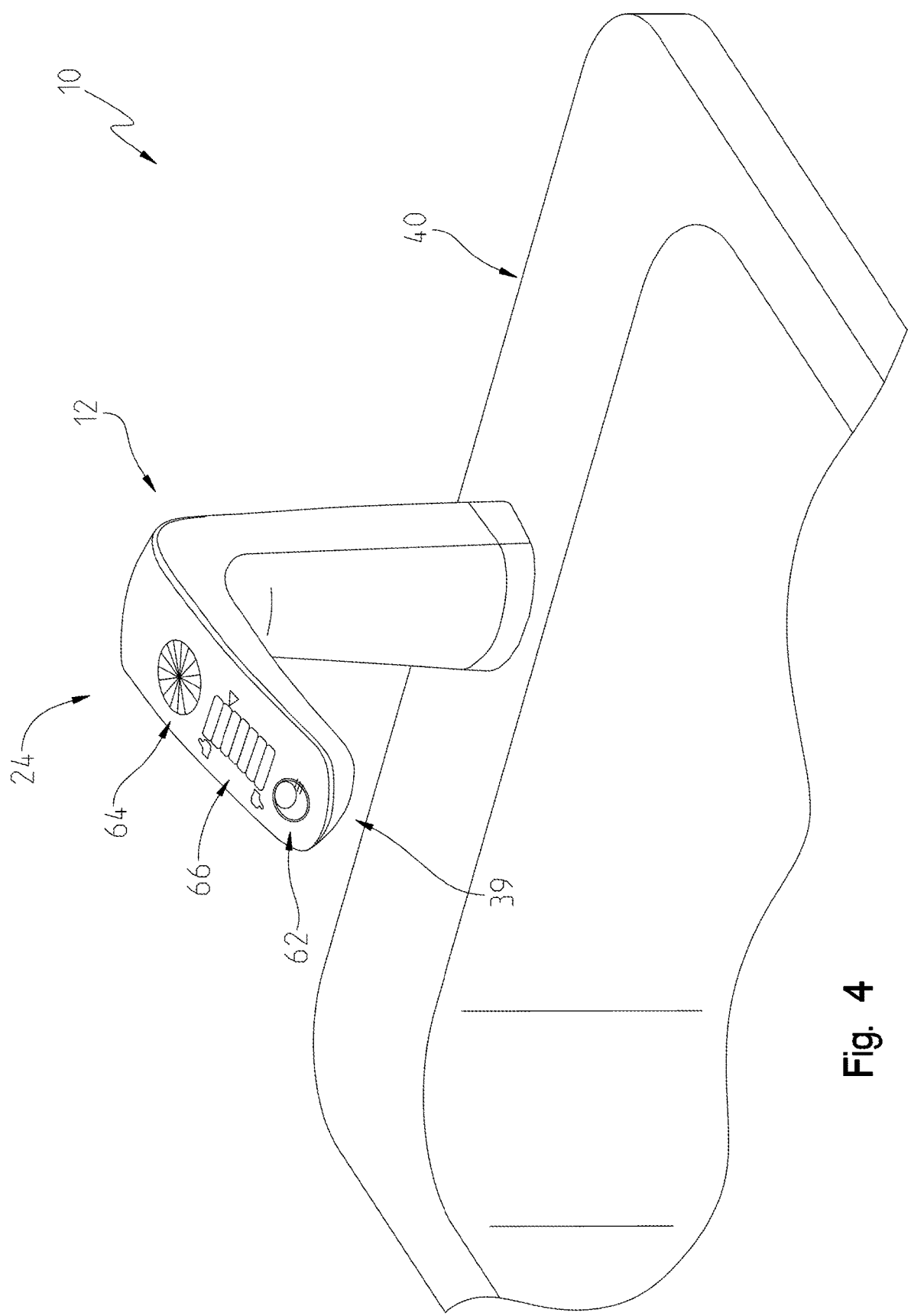
FIG. 4 is a front perspective view of the illustrative faucet of FIG. 3, showing the faucet in a first mode of operation.
Figure 5:
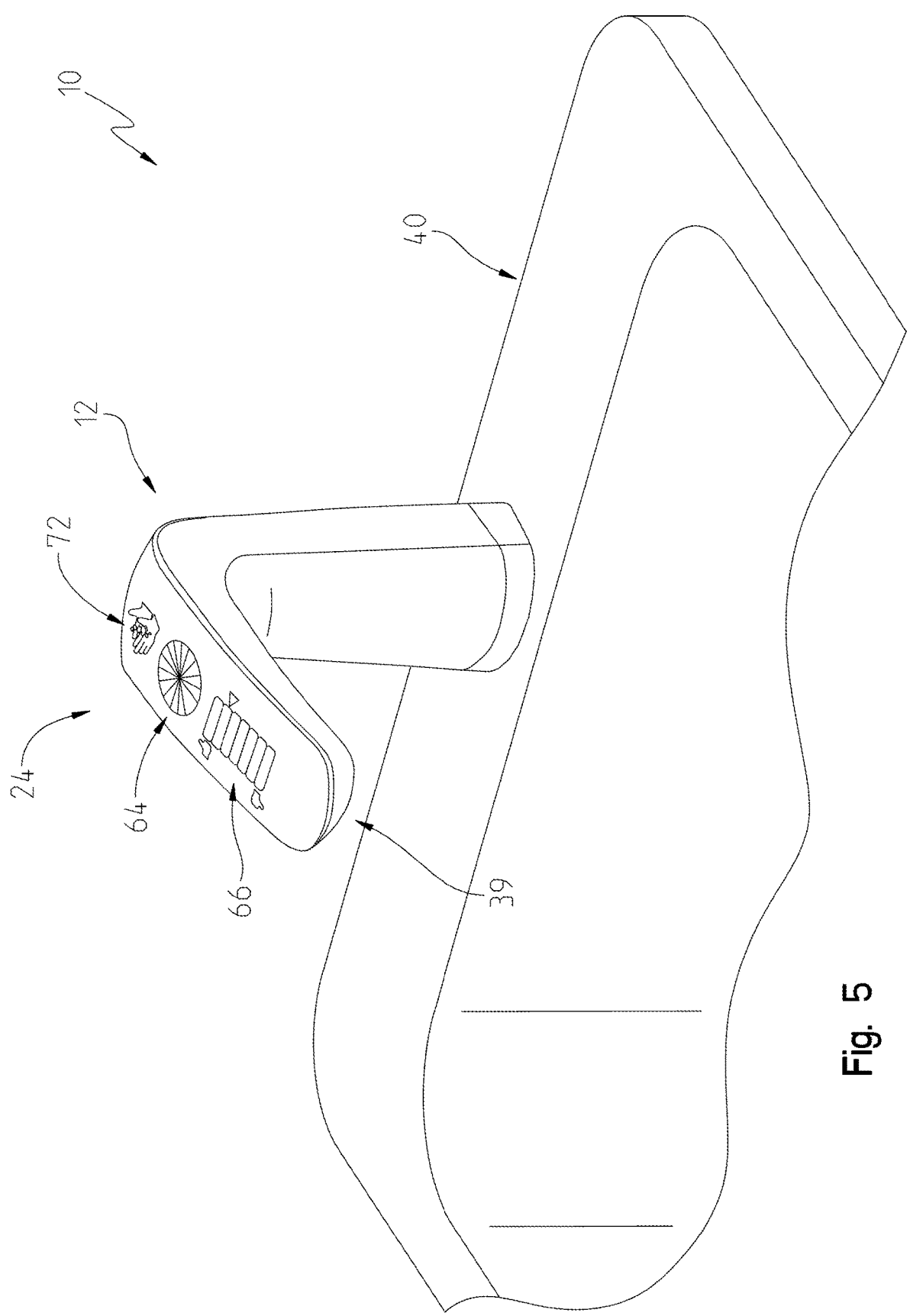
FIG. 5 is a front perspective view of the illustrative faucet of FIG. 3, showing the faucet in a second mode of operation.

Faucet 10 is illustratively configured for operation in at least two modes, including: a first or treatment mode (FIG. 4), and a second, non-treatment or tap water mode (FIG. 5). For example, when operating in the treatment mode, faucet 10 is configured to flow a fluid (e.g., water) through water treatment assembly 18 which disinfects at least a portion of the fluid flowing therethrough to provide fluid with antibacterial properties from spout 12. However, when operating in the non-treatment mode, fluid is configured to bypass water treatment assembly 18 such that fluid from waterway assembly 16, enters valve assembly 14, and is directed to spout 12. In an illustrative embodiment, the water may flow through filter 17 when faucet 10 operates in either the treatment mode or the non-treatment mode.

Figure 2:
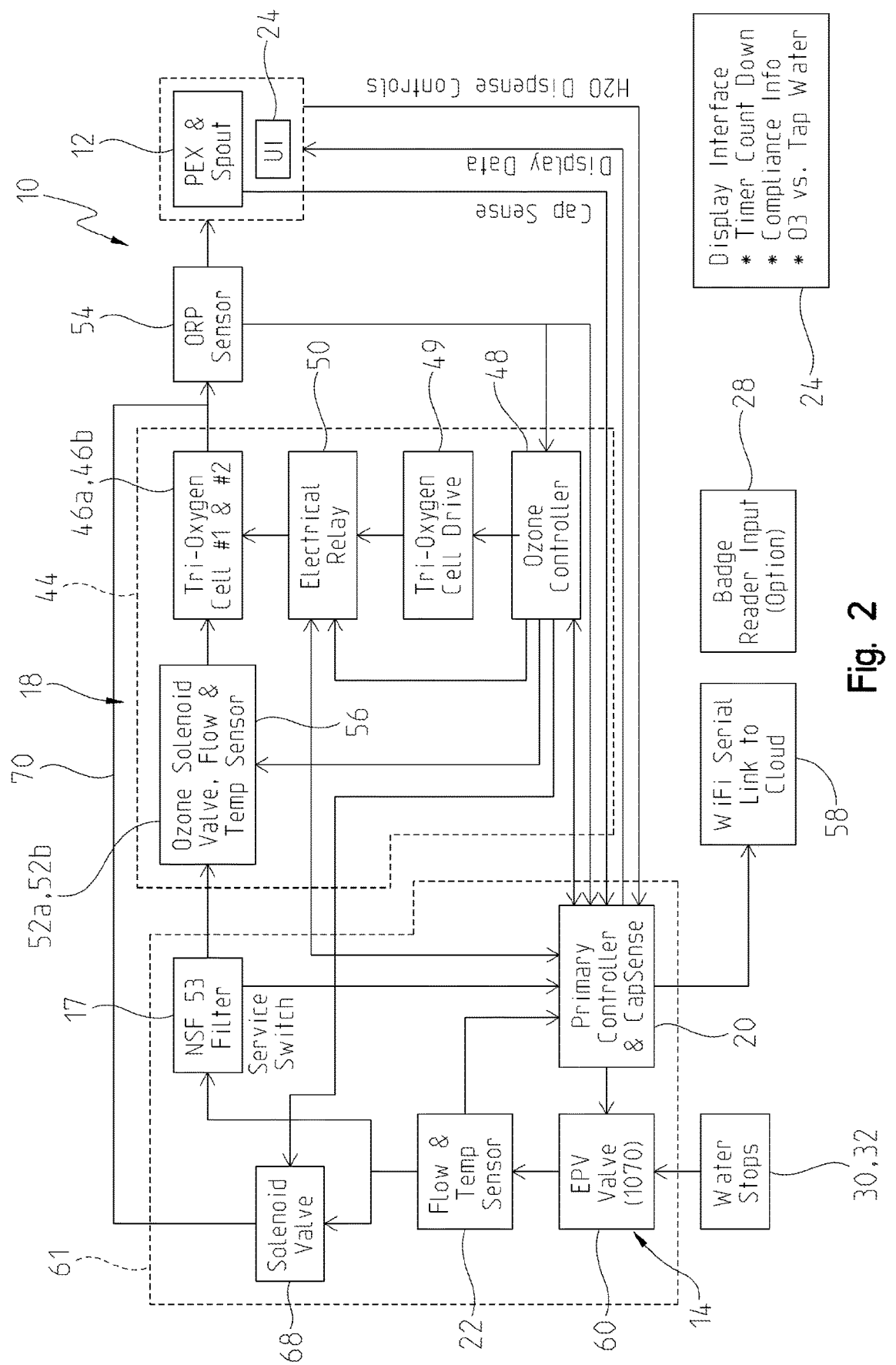
FIG. 2 is a further block diagram of the various components of the illustrative faucet of FIG. 1.

As shown in FIG. 2, in an illustrative embodiment, fluid treatment assembly 18 includes an ozone device 44 which may include at least one ozone cell or electrolytic ozone generator 46, an ozone controller 48, an ozone cell drive 49, an electrical relay 50, and at least one fluid treatment sensor, such as a flow rate sensor 52a and/or a temperature sensor 52b. Additionally, fluid treatment assembly 18 may include a solenoid valve 56. Illustratively, a pair of ozone cells 46a and 46b may be provided in parallel, wherein valve 56 may toggle water flow between the cells 46a and 46b. In another illustrative embodiment, the pair of ozone cells 46a and 46b may be provided in series fluid communication, wherein the controller 48 activates only a single ozone cell 46a, 46b is active at any given time. Alternatively or in addition to ozone generator 46, water treatment assembly 18 may include any device configured to treat fluid, e.g., a filter.

Illustratively, faucet 10 may be configured to monitor various consumable elements such as ozone cells 46a, 46b and filter 17. For example, usage of active ozone cell 46a may be monitored by minutes of usage and may be considered depleted at 100 hours of usage. When depleted, valve 56 may switch water flow from the first ozone cell 46a to the second ozone cell 46b. The user may then replace the first ozone cell 46a without causing interruption of the faucet 10.

Usage of filter 17 may also be monitored by gallons of fluid dispensed and/or overall hours of operation. For example, filter 17 may be considered depleted after 600 gallons of fluid and/or 600 hours of usage. Illustratively, a service switch may be provided to sense removal of the filter 17. Additionally, a pressure vent may be controlled via an electrical circuit to open a solenoid valve.

Information on the consumable elements of faucet 10 that may need to be periodically replaced, replaced, or updated may be uploaded to a server, computer, cloud, or any other device to monitor usage of such components. In one illustrative embodiment, the information on the consumable elements of faucet 10 is wirelessly communicated after every usage of faucet 10 to a cloud 58 (FIG. 2) via a wireless serial link.

Referring still to FIG. 2, valve assembly 14 of faucet 10 may include an electronic proportioning valve (EPV) 60 which controls flow rate and temperature of the water and also may be configured as an emergency shutoff valve. For example, a targeted temperature for the fluid output from spout 12 may be approximately 50-90° F., and more particularly, 70° F. when faucet 10 operates in the treatment mode. However, a targeted temperature for the fluid output from spout 12 may be approximately 90-115° F., and more particularly 102-105° F., when faucet 10 operates in the non-treatment mode.

When faucet 10 includes EPV 60, EPV 60 may include one or more shut-off features, which may provide a safety aspect to faucet 10. For example, if faucet 10 is used in a water system that requires two separate sub-systems (identified as ozone device 44 and water flow device 61 in FIG. 2) and required to operate simultaneously for faucet 10 to operate in the treatment mode, both sub-systems 44 and 61 monitor the parameters of the fluid (e.g., temperature, flow rate, pressure, ORP, and/or current) through sensors in first and/or second sensor modules 22, 26 and determine "agreement" between the readings on each sub-system. If there is disagreement in any reading between the two sub-systems, EPV 60 is configured to stop or shut down operation of faucet 10 such that faucet 10 stops dispensing fluid.

An additional safety feature may be provided by the faucet 10 monitoring the flow rate by flow rate sensor 52a. When the flow rate is active, the controller 48 monitors the levels of ozone from the ORP sensor 54 downstream from the ozone cell 46 (alone over time, or compared to a second ORP sensor 54 upstream from the ozone cell 46). If the ORP level is below a set level, then the controller 48 cuts power to the ozone cell 46 and disables flow by solenoid valve 56. The controller 48 then runs a diagnostics check and recycles power. The controller 48 illustratively attempts several reboots of the water treatment assembly 18 before locking it for maintenance, during which a maintenance code is displayed on the user interface 24.

Treatment Mode

Figure 3:
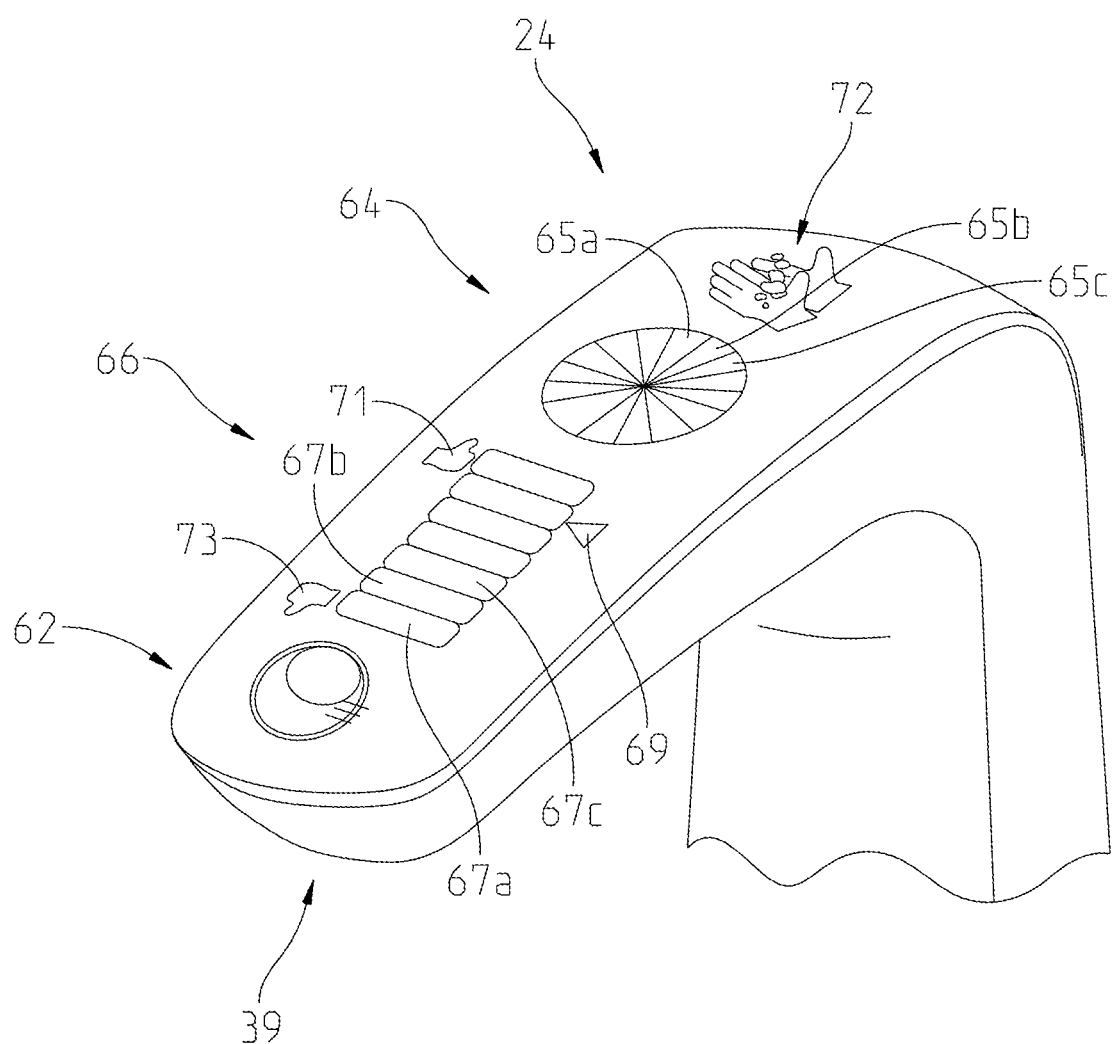
FIG. 3 is a perspective view of a spout supporting a user interface of the illustrative faucet of the present disclosure.

With reference to FIGS. 3-5, during operation of faucet 10, the treatment mode may be set as a default mode such that faucet 10 initially operates in the treatment mode unless the user provides an input indicative of a desire to operate in the non-treatment mode. Alternatively, faucet 10 may operate in the treatment mode only when the user expressly specifies that the treatment mode should be used. For example, the user may input the treatment mode to user interface 24 which sends a signal to controller 20 to activate fluid treatment assembly 18. In this way, fluid from valve assembly 14 is directed through fluid treatment assembly 18 and, more particularly, through ozone device 44, to disinfect at least a portion of the fluid flowing to spout 12.

A light (e.g., LED) or other illumination device (not shown) may be positioned at, on, or near outlet 39 of spout 12 to illuminate the water flowing therefrom when faucet 10 operates in the treatment mode. In this way, the light indicates to the user that faucet 10 is in the treatment mode. Alternatively, spout 12 and/or user interface 24 may provide a visual indicator (e.g., words, graphics, colors, or sounds) that faucet 10 is in the treatment mode. For example, an ozone mode indicator 62 of the user interface 24 may be illuminated when the faucet 10 is operating in the ozone mode.

Fluid treatment assembly 18 may be configured to operate for a predetermined length of time before automatically turning off. For example, fluid treatment assembly 18 may operator for a minimum of 30 seconds before turning off and no longer disinfecting the fluid. After the predetermined length of time, valve assembly 14 also may automatically close to stop the flow of fluid to spout 12. Alternatively, valve assembly 14 may remain open to allow a continuous flow of fluid to spout 12 until the user turns off the fluid, however, the fluid may no longer be disinfected after operation of fluid treatment assembly 18. In such circumstances, the light or visual indicator 62 on spout 12 also may turn off to indicate to the user that the fluid is no longer disinfected.

During the treatment mode, controller 20 sends a serial command to ozone controller 48 to begin generating ozone. Ozone controller 48 enables ozone solenoid valve 56, and outputs a voltage to ozone cell(s) 46 (e.g., tri-oxygen cells) with a current of 0.8-2.0 Amps and, more particularly, a current of 1.2 Amps. Illustratively, the voltage and current to ozone cells 46 are reversed in periodic intervals (e.g., every 20 seconds) to prevent lime build up and keep the electrodes (not shown) within ozone cells 46 clean. The level of current may be adjusted based on the temperature of the water as sensed by temperature sensor 52b. Additionally, depending on the oxidation-reduction potential (ORP) of the water as sensed by ORP sensor 54, the current to the ozone cells 46 may be adjusted. Illustratively, ORP sensors 54 may be provided upstream and downstream from the ozone cells 46 to indicate that ozone is being generated. Current draw of ozone cell 46 indicates relative level of ozone. Finally, ozone gas resulting from outgassing may be collected and destroyed.

Ozone controller 48 also tracks usage and performance level of ozone cells 46. Illustratively, the ozone cells 46 are configured to reduce bacteria and viruses by 2 log or greater by providing an ozone concentration of 0.5 ppm at 0.5 gpm (efficacy determination). When a cell 46 is depleted, ozone controller 48 may operate other ozone cells 46 and/or provide a signal to controller 20 indicative of the depleted ozone cell 46. In this way, controller 20 may provide an output to the user via user interface 24 and/or to the monitoring system for faucet 10 that one of ozone cells 46 is depleted and may be replaced.

During illustrative operation of faucet 10 in the treatment mode, controller 20 provides an output to user interface 24 to show the elapsed time of operation for fluid treatment assembly 18 and/or a particular user's level of compliance with hand hygiene protocols. For example, user interface 24 may include a time indicator, such as a count-down or count-up timer or clock 64 (numeric or graphical) for the run time of ozone device 44, time that water is discharged from the outlet 39 of spout 12, and/or time that a user's hands are in the water stream discharged from the outlet 39 of spout 12. Illustratively, the clock 64 includes a dial including a plurality of sectors that are selectively illuminated in response to run time of the ozone device 44. For example, sectors 65a, 65b, 65c, etc. of the clock 64 may initially all be illuminated and then selectively turned off as time progresses (FIG. 3).

Compliance with hand hygiene protocols may be measured by the capacitive sensor 42 determining that the user's hands are placed and/or moving in the water stream discharged from spout outlet 39 for a period of time. This can be sensed by an absolute shift in measured capacitance (e.g., placement of hands in the water stream) or relative and random signal changes in the capacitive signal (e.g., movement of hands in the water stream) indicative of hand washing activity.

Additional details of capacitive sensing, including sensing a user's hands in a water steam of a faucet, are further detailed in U.S. Pat. No. 8,118,240, entitled "PULL-OUT WAND", U.S. Pat. No. 9,187,884, entitled "FAUCET INCLUDING A CAPACITANCE BASED SENSOR", and U.S. Patent Application Publication No. 2016/0177550, entitled "FAUCET INCLUDING CAPACITIVE SENSORS FOR HANDS FREE FLUID FLOW CONTROL", the complete disclosures of which are expressly incorporated by reference herein.

User interface 24 may also include a compliance indicator 66. More particularly, the compliance indicator 66 illustratively shows incremental increases by illuminating various sections 67a, 67b, 67c, etc. of the indicator 66, and/or by moving an pointer 69 along the indicator 66, while a user's hands are in the fluid stream, showing progress and encouraging the user to complete the disinfectant cycle (e.g., the predetermined 30-second cycle that ozone device 44 automatically operates, as disclosed herein).

Another indicator may be displayed on user interface 24 if the user's hands remained within the fluid stream during the complete operation cycle of ozone device 44. For example, a pass or "reward" indicator 71 (e.g., a green "thumbs up") may be displayed if full compliance is achieved, while a fail indicator 73 (e.g., a red "thumbs down") may be displayed in full compliance is not achieved (FIG. 3). If the designated timeout occurs such that ozone device 44 stops operating or full compliance by the user is achieved, solenoid valve 56 turns off to stop operation of ozone device 44 and the level of compliance is displayed on user interface 24.

Controller 20 also monitors the output of the sensors comprising first and/or second sensor modules 22, 26. More particularly, when fluid flows through valve assembly 14, EPV 60 may continuously adjust the hot/cold fluids to mix the water in a manner to reach a targeted temperature (e.g., 70° F. during treatment mode). Additionally, controller 20 monitors the output from the ORP sensor 54 and ensures that the output is within pre-defined parameters. If the output from the ORP sensor 54 is not within the predefined parameters while in the treatment mode, EPV 60 may turn off water flow by closing valve assembly 14 and controller 20 sends a signal to stop operation of ozone cell(s) 46 via electrical relay 50.

At the end of every use of faucet 10, the compliance data may be uploaded to a monitoring system or device for faucet 10, which may be a computer, server, the "cloud," or any other data device configured to receive information from controller 20. In one embodiment, the compliance data is provided to the monitoring system through a wireless link to the "cloud." If faucet 10 is in a medical facility (e.g., a hospital), the compliance data may be wirelessly transmitted to the monitoring system or device through the medical facility's wireless internet. The compliance data includes a unit ID or badge ID, location, usage time stamp, compliance level (e.g., percentage of time the user's hands were within the fluid stream), and any other data related to maintenance and/or operation of faucet 10. Quality control personnel can access this data to run reports for this location or a grouping of faucets 10.

In one illustrative embodiment, as shown in FIG. 2, the user may be required to scan or otherwise provide identification information through badge reader 28 before faucet 10 will operate in either the treatment mode and/or the non-treatment mode. For example, if faucet 10 is in a medical facility, the user may be required to scan or otherwise provide employee ID information to badge reader 28 to allow faucet 10 to monitor the user's compliance with hand hygiene protocols during operation of faucet 10.

Non-Treatment Mode

With reference to FIGS. 2 and 4, a user may provide an input to the faucet 10 indicative of a desire to operate in the non-treatment or tap water mode. In one illustrative embodiment, when a user wishes to wash his or her hands using traditional tap water, the user may activate a conventional sensor (such as an infrared (IR), potentiometer, membrane switch, $2^{nd}$ capacitive sensor, foot pedal, etc.). This sensor is monitored by the primary controller 20 to send a command to the ozone controller 48 to turn on a tap water solenoid valve 68. When the solenoid valve 68 is open, water flows through a bypass line 70. Once water flow begins, the primary controller 20 will adjust the EPV 60 to deliver 102-105° F. water temperature to the spout 12. The primary controller 20 may illustratively display a hand washing signal on user interface 24 to use soap, and also monitor hands in the water stream, giving an indication for appropriate length and compliance level on user interface 24.

As in the treatment mode, water may be turned off at a preset time or when hands are absent for a set period of time (3-5 seconds). This information may also be illustratively uploaded to the cloud at the end of every usage. Spout 12 and/or user interface 24 may provide a visual indicator (e.g., words, graphics, colors, or sounds) that faucet 10 is in the non-treatment or tap water mode. For example, a tap water mode indicator 72 of the user interface 24 may be illuminated when the faucet 10 is operating in the non-treatment or tap water mode.

Also as in the treatment mode, during illustrative operation of faucet 10 in the non-treatment mode, controller 20 provides an output to user interface 24 to show the elapsed time of operation and/or a particular user's level of compliance with hand hygiene protocols. For example, user interface 24 may include count-down or count-up timer or clock 64 (numeric or graphical) for the time during which the valve 68 is open thereby causing tap water to flow through bypass line 70 to outlet 39 of spout 12, and/or time that a user's hands are in the water stream discharged from the outlet 39 of spout 12. Compliance with hand hygiene protocols may be measured by the capacitive sensor 42 determining that the user's hands are placed in the water stream discharged from spout outlet 39 for a period of time. This can be sensed by an absolute shift in measured capacitance (e.g., placement of hands in the water stream) or relative and random signal changes in the capacitive signal (e.g., movement of hands in the water stream) indicative of hand washing activity.

The compliance indicator 66 illustratively shows incremental increases while a user's hands are in the water stream, showing progress and encouraging the user to complete the hand washing cycle (e.g., a predetermined 30-second). Another indicator may be displayed on user interface 24 if the user's hands remained within the water stream during the complete operation cycle. For example, a "reward" indicator may be displayed if full compliance is achieved, while a fail indicator may be displayed in full compliance is not achieved.

Figure 6:
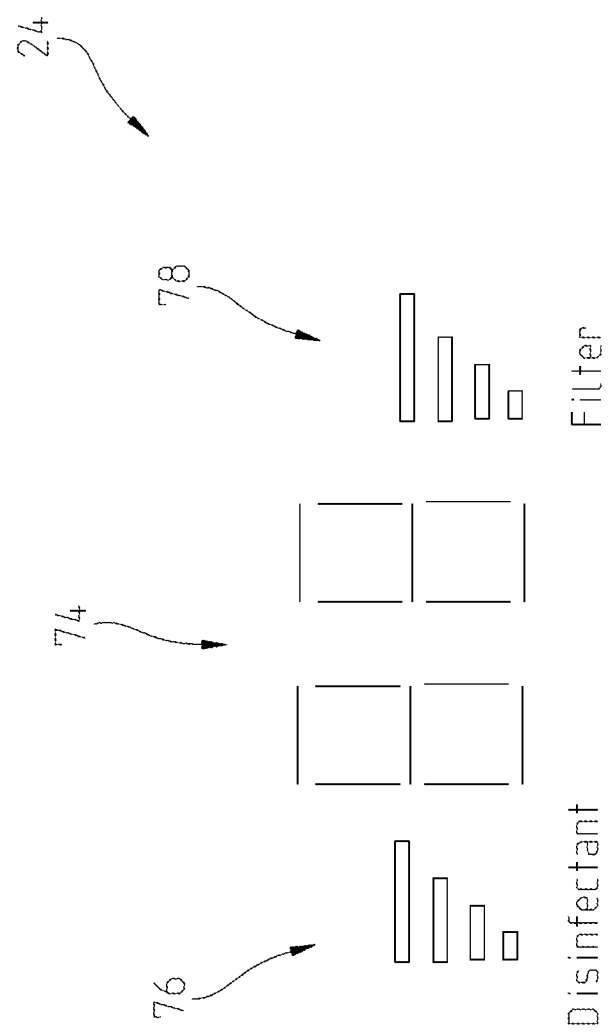
FIG. 6 is a schematic view of a user display for the illustrative faucet of FIG. 3.

With reference to FIG. 6, additional details of a further illustrative user interface 24 are shown. The user interface 24 may include a digital indicator 74 that provides an indication of time (such as clock 64 detailed above, but in a numeric form), and/or of operation or maintenance conditions of the faucet 10. For example, the indicator 74 may display error codes associated with the faucet 10. A first or O3 graphical indicator 76 may provide an indication of the remaining life expectancy of the active ozone cell 46, while a second or filter indicator 78 may provide an indication of the remaining life expectancy of the filter 17.

The illustrative faucet 10 provides improved hand hygiene by dispensing alternately tap water and ozone infused water that inactivates bacteria and viruses on contact, providing feedback to the user regarding their level of compliance to hand hygiene protocol through an interface supported on the spout (or mounted nearby), utilizing capacitive sensing technology to discern when hands are in the water stream, collecting and reporting usage and compliance information for quality control and improvement, and collecting and destroying ozone gas due to outgassing. As an added safety feature, the faucet 10 illustratively requires that two separate sub-systems function properly to dispense ozone water. Finally, the faucet 10 uses ozone to disinfect hands, uses capacitance sensing to know when hands are in the water stream for compliance reporting, integrates user compliance feedback into the spout, and provides real-time compliance reporting.

Additional features of illustrative faucet 10 may be disclosed in U.S. Patent Application Publication No. 2014/0352799, entitled "OZONE DISTRIBUTION IN A FAUCET", and PCT International Patent Publication No. WO 2013/086217, entitled "OZONE DISTRIBUTION IN A FAUCET", the complete disclosures of which are expressly incorporated by reference herein.

Water Treatment Dispensing System

Figure 7:
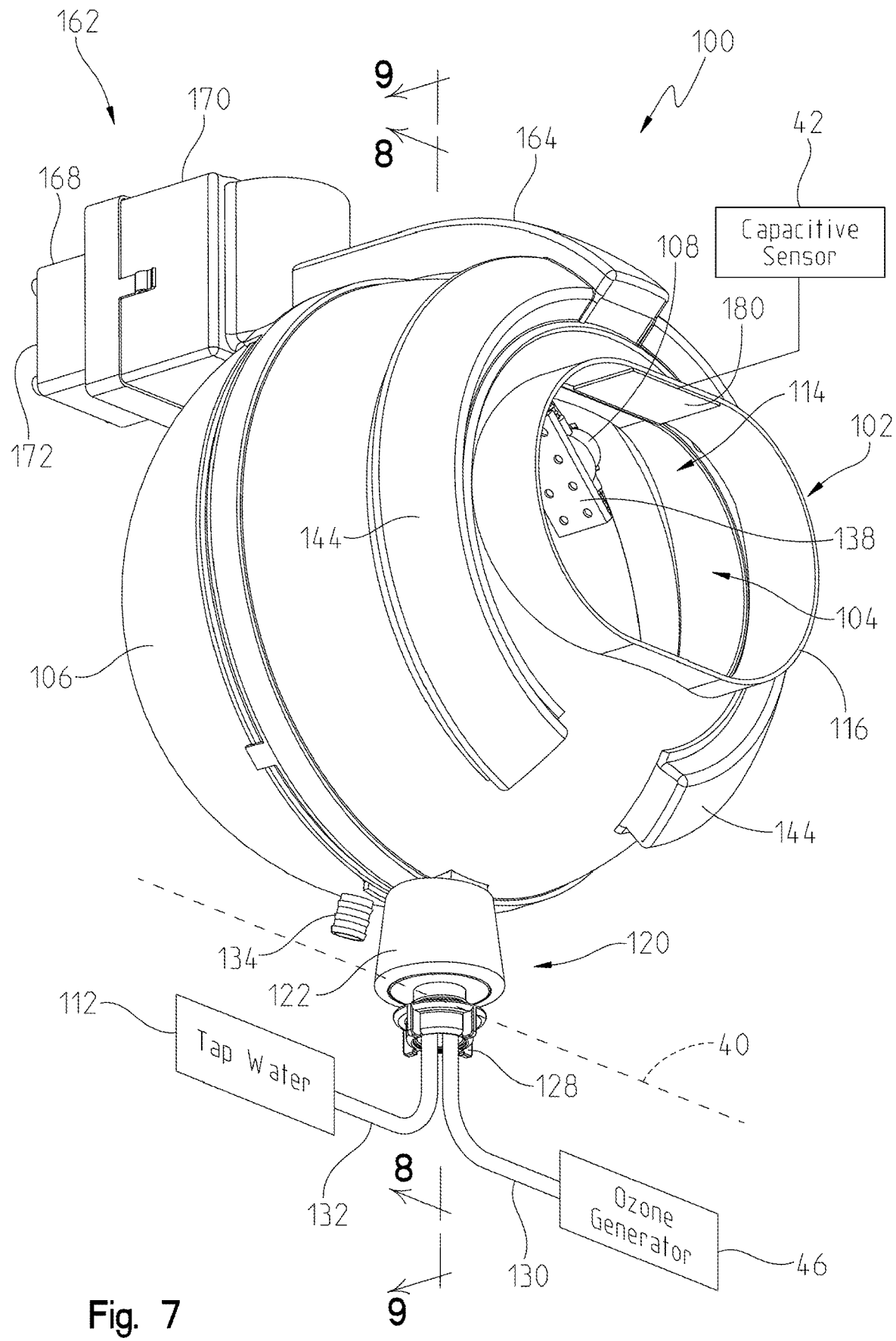
FIG. 7 is a perspective view of an illustrative fluid dispensing system of the present disclosure, the fluid dispensing system including an outer housing having an opening to receive the hands of a user and an ozone off gas collector.
Figure 8:
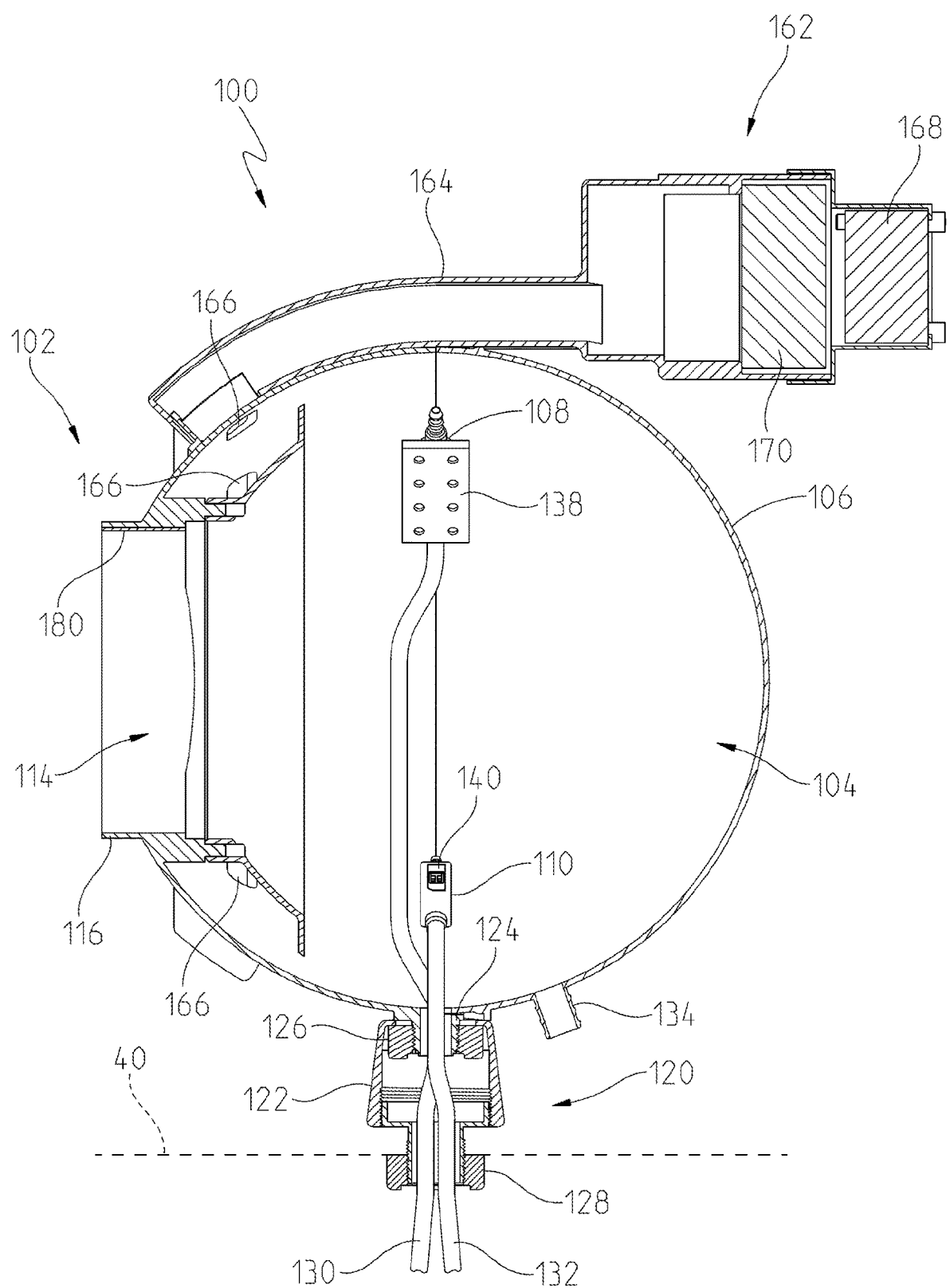
FIG. 8 is a cross-sectional view of the fluid dispensing system of FIG. 7, taken along line 8-8.
Figure 9:
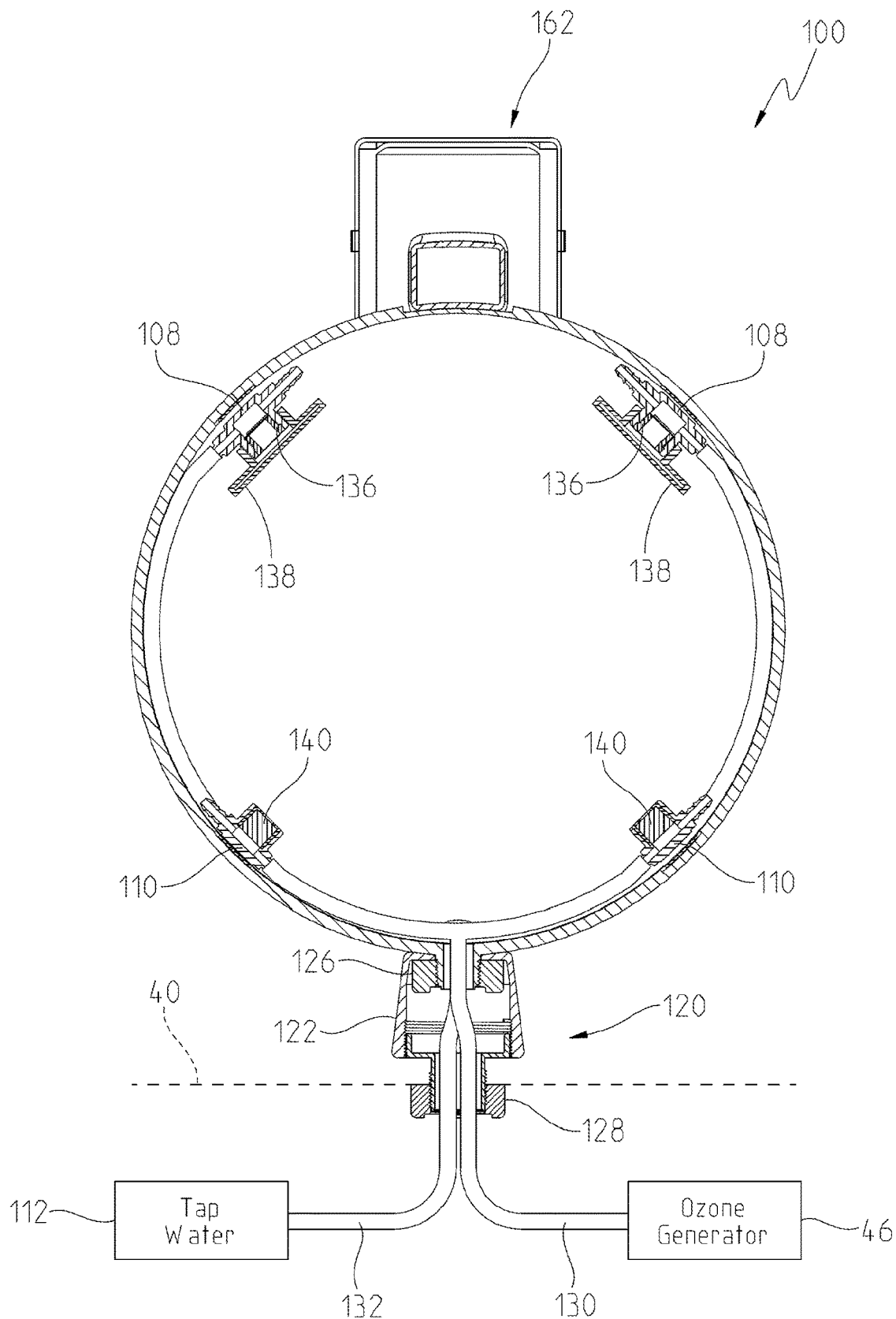
FIG. 9 is a cross-sectional view of the fluid dispensing system of FIG. 7, taken along line 9-9.

With reference to FIGS. 7-9, an illustrative water treatment dispensing system 100 includes an ozone rinsing station 102 including a spherical chamber 104 defined by an outer housing or shell 106. While the outer housing 106 and the internal chamber 104 are illustrated as being spherical, other shapes may be substituted therefore.

A plurality of first fluid device couplers or holders 108 are supported by the outer housing 106 within the chamber 104 and operably coupled to the ozone generator 46 for distributing ozone infused (i.e., ozonated) water. A plurality of second fluid device couplers or holders 110 are supported by the outer housing 106 within the chamber 104 and operably coupled to a tap water source 112 for distributing untreated tap water. The holders 108 and 110 are arranged on an inner surface of the outer housing 106 in a manner to spray ozone infused (ozonated) water evenly on a user's hands when placed within the internal chamber 104.

The outer housing 106 may be formed of a polymer and includes an opening 114 to receive the hands of a user. An oval shield 116 may extend outwardly from the outer housing 106 and surrounds the opening 114. While the opening 114 may be of a variety of shapes and sizes, it is illustratively formed as an elongated slot in order to help prevent the release of outgassing of ozone from within the chamber 104.

A mounting assembly 120 is configured to couple the outer housing 106 to a mounting surface, such as sink deck 40. The mounting assembly 120 includes a shank body 122 coupled to a threaded bushing or sleeve 124 extending downwardly from the outer housing 106 via a first nut 126. In turn, the shank body 122 is coupled to the sink deck 40 by a second nut 128. An ozone water supply tube 130 illustratively extends through the shank body 122 and fluidly couples the ozone generator 46 with the first fluid device holders 108. A tap water supply tube 132 illustratively extends through the shank body 122 and fluidly couples the tap water source 112 with the second fluid device holders 110. A drain bushing or fitting 134 extends downwardly from the outer housing 106 adjacent to the sleeve 124 and is configured to fluidly couple with a drain tube (not shown) for removing waste water.

Each of the first fluid device holders 108 illustratively supports a first fluid device, illustratively configured to deliver ozonated water in a substantially laminar flow to reduce the potential of ozone outgassing. An illustrative first fluid device includes a conventional stream straightener 136 (e.g., an aerator) and/or a conventional spray head 138 (e.g., a rain can). Other fluid devices may be substituted therefore, including laminar flow blades.

Each of the second fluid device holders 110 illustratively supports a second fluid device for delivering an impacting spray providing a physical removal force to assist in removing bacteria and viruses. The disclosed arrangement of first and second fluid devices combine the benefits of physical removal force of tap water with the sanitizing effects of ozone to provide an effective and fast hand cleaning process.

An illustrative second fluid device includes a conventional spray nozzle or a conventional fluidic chip 140. Each fluidic chip 140 may be of conventional design and configured to deliver a multi-dimensional spray pattern of water. Illustratively, the fluidic chips 140 are low-pressure, feedback passage-free fluidic oscillators which provide patternization, spray distribution across a fan angle, shape, and/or articulate a water spray. Illustratively, the fluidic chips 140 may be of the type manufactured by Bowles Fluidics Corporation of Columbia, Md., USA.

Figure 10:
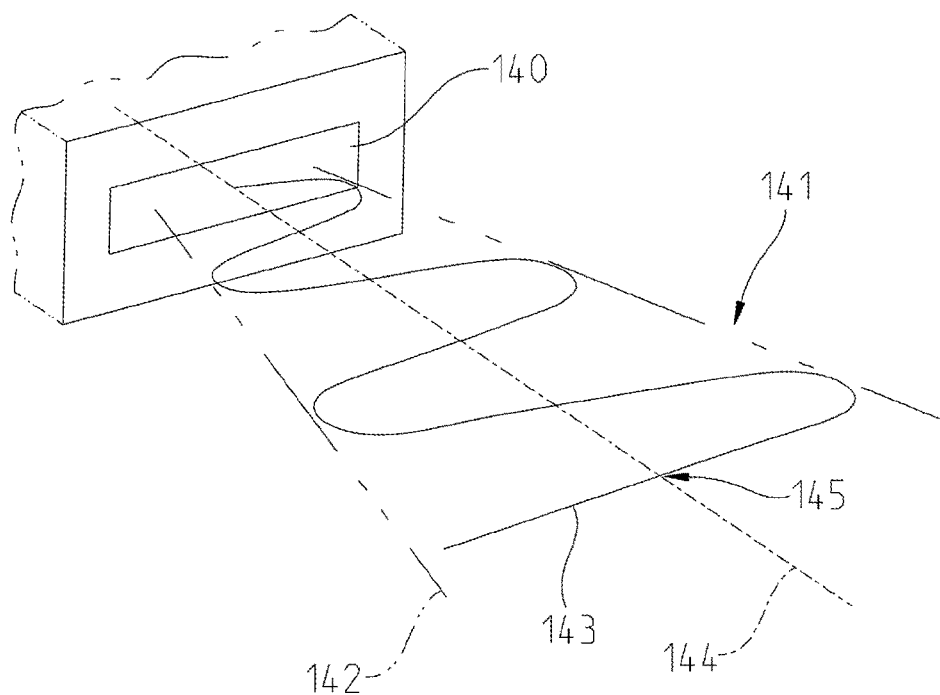
FIG. 10 is a perspective view in partial schematic of water dispensed by a two-dimensional fluidic device of the present disclosure.

With reference to FIG. 10, the fluidic chips 140 are shown as two-dimensional (2D) fluidic chips or nozzles that are configured to produce a fan of water 141 within a plane 142 by oscillating a water stream 143 about a center axis 144. The resulting spray 145 is illustratively a line in cross-section.

Figure 11:
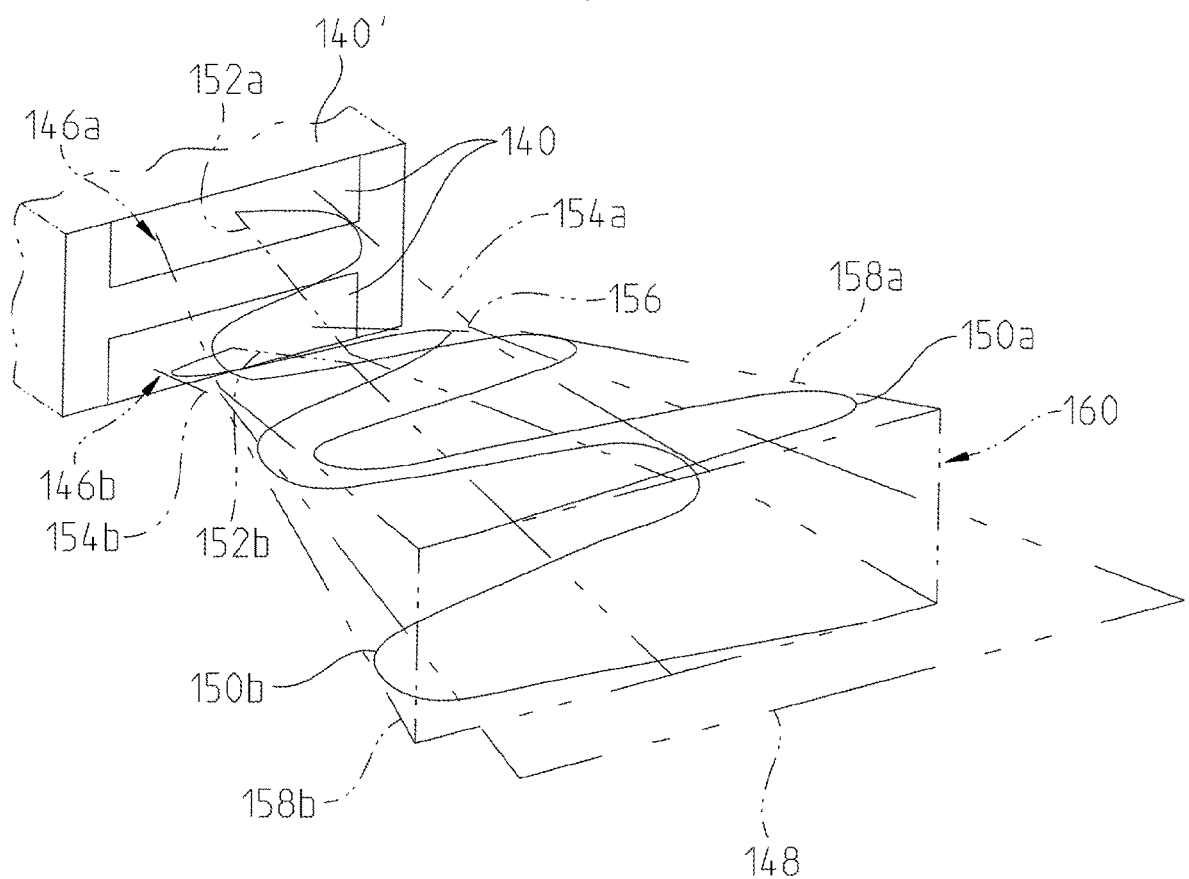
FIG. 11 is a perspective view in partial schematic of the water dispensed by a three-dimensional fluidic device of the present disclosure.

With reference to FIG. 11, the fluidic chips 140' are shown as three-dimensional (3D) fluidic chips or nozzles configured to produce a pair of interacting fans of water 146a, 146b. In general, each 3D fluidic chip 140' comprises a pair of adjacent 2D fluidic chips 140 disposed parallel to each other. Moreover, the 3D effect may be produced by combining two 2D fluidic chips 140 that have initially converging fans of water 146a, 146b that upon contact proximate a center plane 148 reflect outwardly away from each other. Illustratively, the fans of water 146a, 146b are formed by oscillating water streams 150a, 150b about a respective center axis 152a, 152b within initially converging planes 154a, 154b. At convergence point 156, the fans of water 146a, 146b reflect away from each other in diverging planes 158a, 158b, thereby moving in a direction away from center plane 148. The resulting spray 160 illustratively defines a rectangular cross-section.

While two first fluid device holders 108 and two second fluid device holders 110 are shown in the illustrative embodiment, the number, type and orientation of the holders 108, 110 and associated fluid devices 136, 138, 140 may vary. In certain illustrative embodiments, ozonated water is delivered via the holders 108 and fluid devices 136, 138, while tap water is delivered via the holders 110 and fluid devices 140. In other illustrative embodiments, ozonated water is delivered via the holders 110 and fluid devices 140, while tap water is delivered via the holders 108 and fluid devices 136, 138. In yet other illustrative embodiments, ozonated water is delivered via the holders 108 and fluid devices 136, 138, and via the holders 110 and fluid devices 140.

In an illustrative embodiment, the fluidic chips 140 are arranged within the chamber 104 to simultaneously cover the surface area of a user's hands using a flow rate of between 1.0 to 1.4 gallons per minute (gpm) and at an ozone concentration rate of approximately 0.80 parts per million (ppm). In a first illustrative embodiment, two stream straighteners 136 supported in holders 108 are positioned above two 3D fluidic chips 140' positioned in holders 110, wherein the stream straighteners 136 provide laminar streams of tap water and the 3D fluidic chips 140' provide sprays of ozonated water. In a second illustrative embodiment, two 3D fluidic chips 140' are positioned in holders 108 for spraying ozonated water downwardly. In a third illustrative embodiment, two 3D fluidic chips 140' supported in holders 108 are positioned above two stream straighteners 136 supported in holders 110, wherein the 3D fluidic chips 140' provide sprays of ozonated water and the stream straighteners 136 provide laminar streams of tap water. In a fourth illustrative embodiment, two spray heads 138 supported in holders 108 are positioned above two 3D fluidic chips 140' positioned in holders 110, wherein the spray heads 138 provide a plurality of laminar streams of tap water and the 3D fluidic chips 140' provide sprays of ozonated water.

Additional details on illustrative fluidic chips may be found, for example, in U.S. Patent Application Publication No. 2013/0299608, entitled "SHOWERHEAD WITH MULTI-DIMENSIONAL FLUID DISPENSERS", the complete disclosure of which is expressly incorporated by reference herein.

A gas mitigation system 162 may be provided to collect outgas from the ozonated water (i.e., ozone outgassing mitigation). The gas mitigation system 162 illustratively includes intake ducts 164 in fluid communication with the internal chamber 104 through openings 146 formed in the housing 106. A high power fan 168 is configured to draw gas from the chamber 104, through the intake ducts 164 and a filter 170, toward an exhaust outlet 172. The filter 170 illustratively comprises a carbon filter which is known to readily destroy ozone.

An electrode 180, such as a metal plate, is illustratively coupled to the capacitive sensor 42, thereby defining a user detector operably coupled to the controller 20. The user detector is coupled to the controller 20 for controlling the valve assembly 14 and the gas mitigation system 162 (e.g., activating and deactivating water flow through the fluid devices 136, 138, 140, and the fan 168). The user detector may comprise a wide variety of different sensors, including infrared (IR) sensors, ultrasonic sensors, capacitive sensors, etc. The electrode 180 is illustratively supported adjacent to the opening 114 by the shield 116, such that the capacitive sensor 42 will sense when a user's hands are within the opening 114. Based upon the amplitude, frequency and/or duration of signal changes, the capacitive sensor 42 can also sense when the user's hands are moving within the chamber 104. A user interface, similar to user interface 24 detailed above, may be operably coupled to the controller 20.

Figure 12:
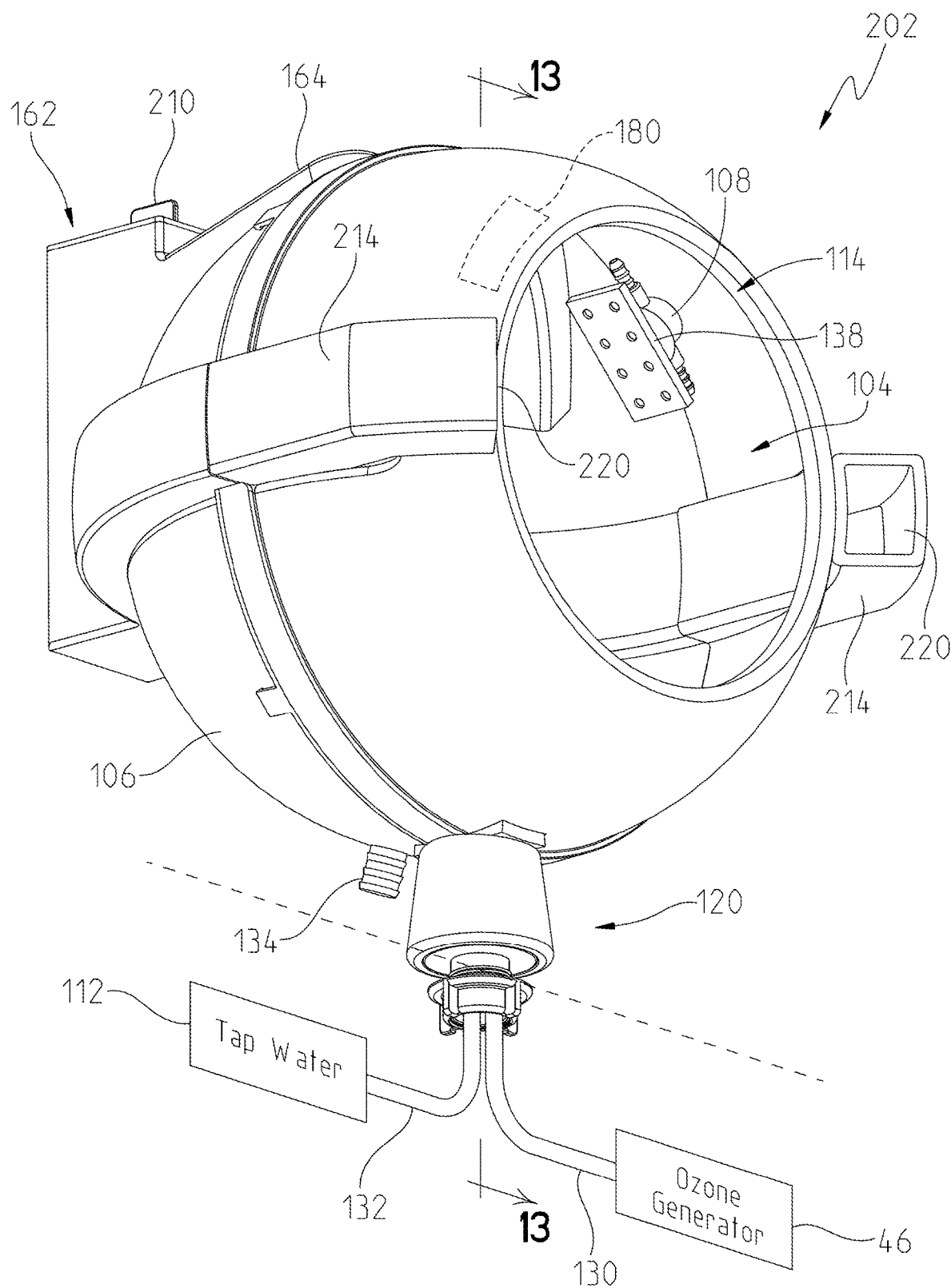
FIG. 12 is a perspective view of another illustrative fluid dispensing system of the present disclosure, the fluid dispensing system including an outer housing having an opening to receive the hands of a user and an ozone off gas collector.
Figure 13:
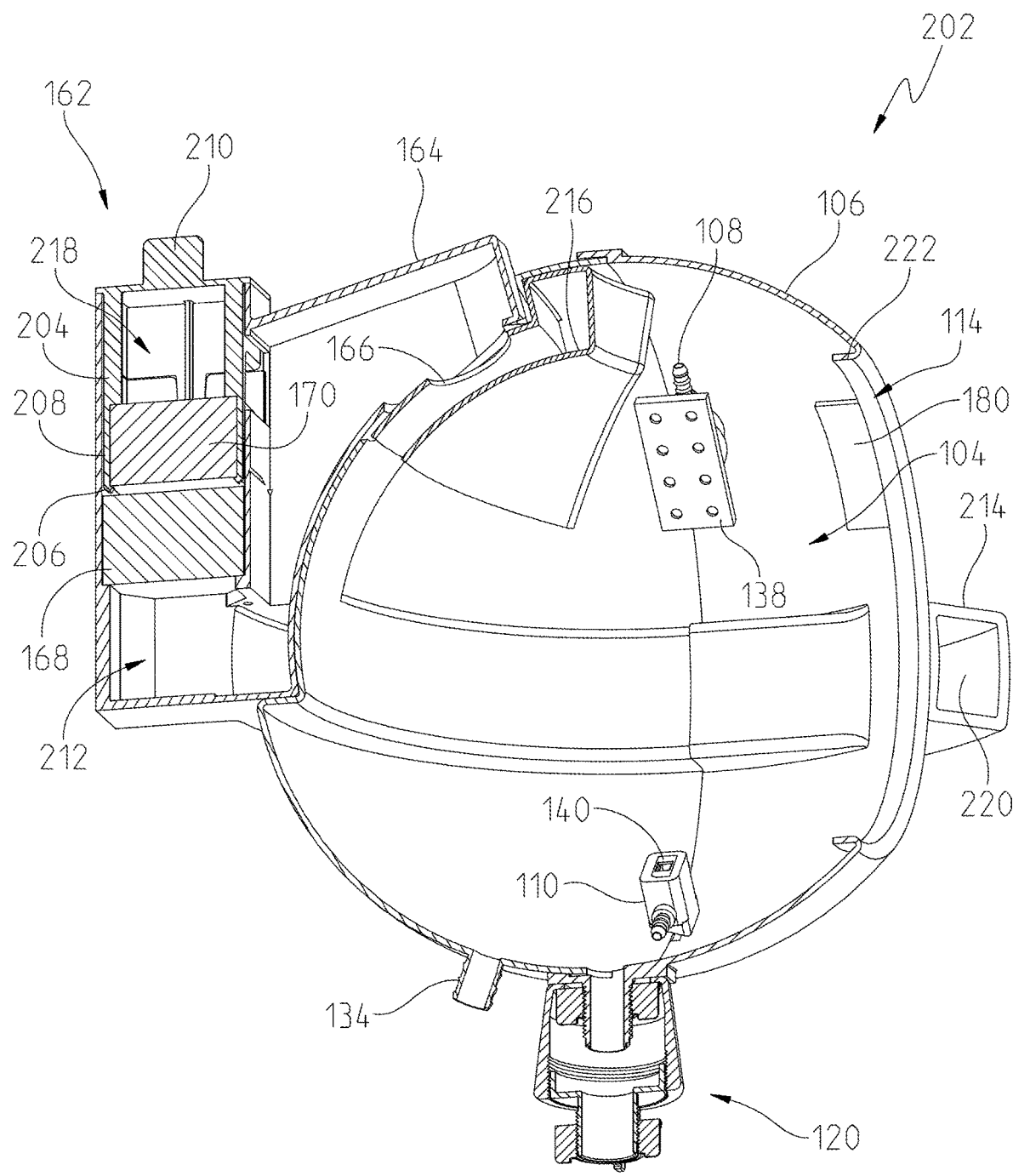
FIG. 13 is a cross-sectional view of the fluid dispensing system of FIG. 12, taken along line 13-13.

FIGS. 12 and 13 show a further illustrative embodiment ozone rinsing station 202 including many similar features to those of the ozone rising station 102 detailed above. In the following description, like reference numbers identify similar components. As shown in FIG. 13, a filter holder 204 holds the carbon block filter 170 in place and makes it easy to replace or service. Undercuts 206 on retention fingers 208 holds the carbon block 170 in place. Pulling up on a tab 210 pulls the block filter 170 out of its housing, thereby allowing for servicing or replacement. Openings 166 allows air to be sucked out of the chamber 104, through the carbon block 170 and into the outlet chamber 212 and out through vent arms 214. A water shield 216 prevents water from the chamber 104 from being drawn into the exhaust chamber 218 and into the carbon filter 170. Air exhausting out of outlet ports 220 agitates the outside air facilitating the mixing of air and ozone to dilute any ozone escaping the chamber 104 and also aids in ozone destruction.

A user's hands are inserted into the opening 114 of the housing 106 to rinse them. Electrode 180 of capacitive sensor 42 is illustratively hidden from sight behind a lip 222 will turn the unit on (activate water flow through fluid devices 136, 138, 140. The electrode 180 may include discrete parts (e.g., four different parts) that will allow the controller 20 to determine whether the user's hands are moving within the chamber 104. Alternatively, a sense wire can be wrapped about a water line energizing the water stream. The controller 20 can use that to determine the 'quality' of the rinse. Feedback may be given to the user through the user interface 24, likely a countdown timer letting them know how long they have to the end of the rinse, and a 'count up timer' that shows the 'quality' of the rinse—how much the hands are moving in the stream. It is desirable for the user's hands to be exposed to tap water discharged from the fluidic chips 140, as well as the ozonated water discharged from the fluid devices 136, 138.

Figure 14:
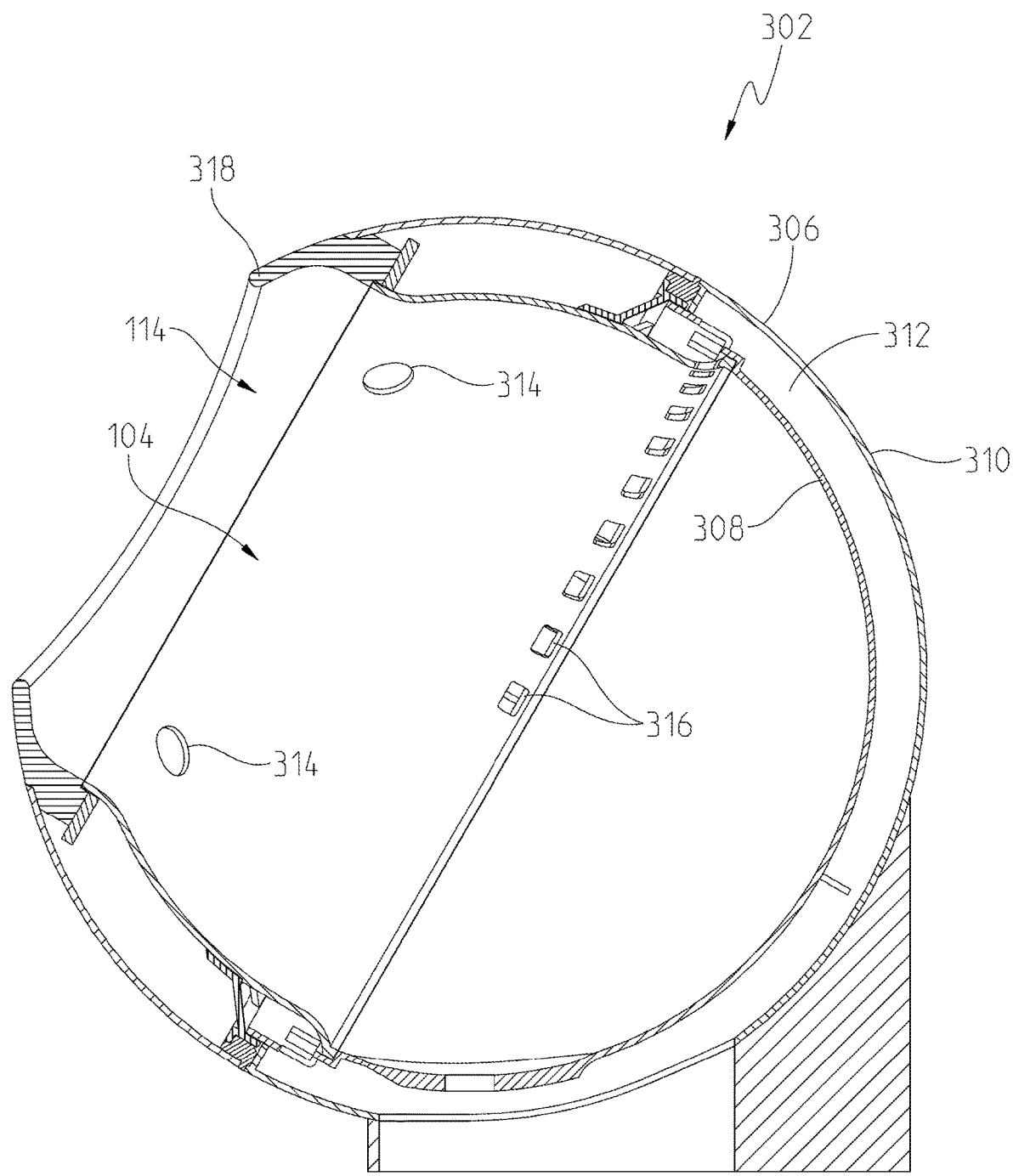
FIG. 14 is a cross-sectional view of a further illustrative fluid dispensing system of the present disclosure.

FIG. 14 shows a further illustrative embodiment ozone rinsing station 302 including many similar features to those of the ozone rising stations 102 and 202 detailed above. In the following description, like reference numbers identify similar components. The outer housing 306 is of a dual walled construction, including an inner wall 308 spaced inwardly from an outer wall 310 and defining a passageway 312 therebetween. The passageway 312 between the walls 308 and 310 allows space for wiring, air passages and for plumbing, including the water outlet devices. More particularly, fluid devices (such as stream straighteners 136, spray heads 138 and/or fluidic chips 140) are configured to project through the inner wall 308 to provide both types of flows inside chamber 104.

The passageway 312 between the walls 308 and 310 also allows air to be drawn out of the chamber 104, through vents 316, through carbon block filter 170 using a fan 168 as previously described (FIG. 13). The dual walled construction allows for an ozone resistant material to be used on the interior components (including inner wall 308) while allowing a material with better appearances to be used on the exterior (including outer wall 310).

A translucent, illustratively transparent, lens 318 may be used as a light pipe to convey feedback information to the user. Illustratively, the lens 318 extends around at least a portion of the opening 114 for receiving the hands of the user. The lens 318 is operably coupled to a light source, such as an LED (not shown) which, in turn, is operably coupled to controller 20.

In operation, the hands of a user are inserted into the opening 114 of the outer housing 106. When the user detector, illustratively the capacitive sensor 42 coupled to the electrode 180, detects the user's hands within the chamber 104, the controller 20 starts the rinse cycle and monitors the actual use/duration of the rinse. More particularly, the controller 20 will cause the valve assembly 14 to cause ozonated water to flow through the fluid devices 136, 138 coupled to the first fluid device holders 108, and tap water to flow through the fluid devices 140 coupled to the second fluid device holders 110. Simultaneously, the controller 20 will activate the fan 168 to draw ozone outgassing through the carbon filter 170. After the user's hands have been removed from the chamber 104, as detected by the capacitive sensor 42 coupled to the electrode 180, the controller 20 will cause the valve assembly 14 to stop water flow through the fluid devices 136, 138 and 140. The fan 168 will illustratively run for a predetermined time after flow of the ozonated water has stopped.

The user interface 24 may indicate the time left for a rinse as well as provide feedback as to whether hands are being moved properly. In certain illustrative embodiments, a radio frequency identification (RFID) reader may be supported by the outer housing 106 for identifying the user (for example, through an identification badge). Bluetooth or similar wireless technology could be used to upload data to the cloud, such as hand washing protocol compliance by users, programming that monitors the 'health' of the system, alerts that can let maintenance know when service deadlines are approaching, and any system problems that have been detected.

There may be several different variations of water treatment dispensing system 100, including those used for higher acuity settings (e.g., operating rooms (OR), intensive care units (ICU), neonatal intensive care units (NICU), etc.), and those for lower acuity settings (e.g., patient rooms). Such systems have different durations and coverage requirements. The higher acuity settings would likely require coverage from finger tips to forearms with a clean time of a relatively long duration clean time (e.g., 30 seconds), while the lower acuity settings would likely require coverage from finger tips to wrists with a shorter duration clean time (e.g., 10 seconds).

Figure 15:
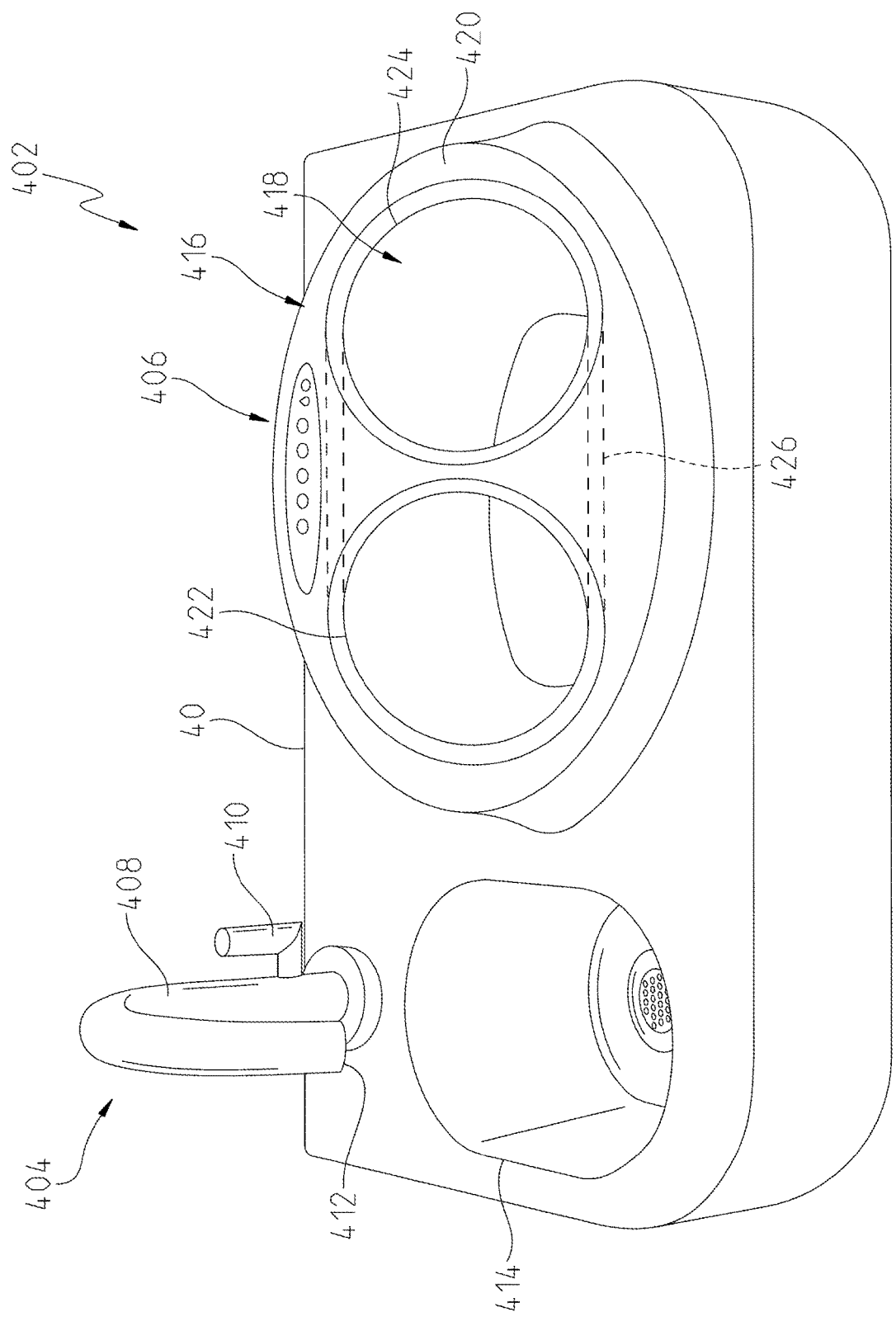
FIG. 15 is a perspective view of another illustrative fluid dispensing system of the present disclosure, the fluid dispensing system including a tap water faucet spout and an outer housing having an opening to receive the hands of a user.

FIG. 15 shows a further illustrative fluid dispensing system 402 including a faucet 404 and a water treatment dispensing system 406 supported adjacent to each other and supported by a sink deck 40. The faucet 404 may be of conventional design as including a spout 408, and a handle 410 coupled to a mixing valve (not shown) for dispensing water from an outlet 412 of the spout 408 into a sink 414.

The water treatment dispensing system 406 may be similar to water treatment dispensing system 100 as detailed above in connection with FIGS. 7-9. For example, the water treatment dispensing system 406 illustratively includes an ozone rinsing station 416 including a chamber 418 defined by an outer housing or shell 420. The user interface 24 may be supported on an external surface of the outer housing 420. Fluid devices 136, 138 are illustratively supported within the chamber 418 for dispensing ozonated water. Similarly, fluid devices 140 are illustratively supported within the chamber 418 for dispensing tap water.

A pair of circular openings 422 and 424 are illustratively formed within an upper portion of the outer housing 420 and are configured to receive the left and right hands of the user. In an alternative illustrative embodiment, the two circular openings 422 and 424 may be replaced with a single elongated or oval opening (represented by hidden lines 426 in FIG. 15).

Although the invention has been described in detail with reference to certain preferred embodiments, variations and modifications exist within the spirit and scope of the invention as described and defined in the following claims.

The invention claimed is:

1. A faucet comprising:
a spout including a waterway defining an outlet
at least one valve in fluid communication with the waterway of the spout
a controller in communication with the at least one valve;
a disinfectant device fluidly coupled to the waterway of the spout, the faucet being configured to selectively flow fluid through the disinfectant device in response to an input to the controller;
wherein the disinfectant device includes an electrolytic ozone generator; and
wherein the ozone generator comprises:
an outer cartridge;
an electrolytic cell assembly received within the outer cartridge, the electrolytic cell assembly comprising:
a first housing;
an anode coupled to the first housing;
a second housing
a cathode coupled to the second housing;
a separator positioned between the anode and the cathode; and
a holder that couples the first housing to the second housing independently of the outer cartridge.

2. The faucet of claim 1, further comprising a gas mitigation system in electrical communication with the controller and including a fan to draw ozone outgas.

3. The faucet of claim 1, wherein the electrolytic ozone generator includes a first electrolytic ozone generator in serial fluid communication with a second electrolytic ozone generator.

4. The faucet of claim 1, further comprising a sensor in communication with the controller and configured to detect a user's hands in proximity to the spout, the controller configured to determine hand washing compliance.

5. The faucet of claim 4, wherein the sensor includes an in-water sensor configured to detect a user's hands in a water stream delivered from the outlet of the spout.

6. The faucet of claim 5, wherein the in-water sensor is configured to detect a user's hands moving in the water stream delivered from the outlet of the spout.

7. The faucet of claim 5, wherein the in-water sensor includes a capacitive sensor.

8. The faucet of claim 1, further comprising a sensor in communication with the controller and configured to detect the status of the antibacterial device.

9. The faucet of claim 1, further comprising a user interface in communication with the controller, the user interface including a time indicator configured to display a representation of the time water is discharged from the outlet of the spout.

10. The faucet of claim 9, wherein the time indicator includes a circular dial including a plurality of sectors that are selectively illuminated based upon the time that water is discharged from the outlet of the spout.

11. The faucet of claim 1, wherein the faucet is configured to selectively operate in a treatment mode and a non-treatment mode, where treated water passes through the disinfectant device in the treatment mode, and non-treated water by-passes the disinfectant device in the non-treatment mode.

12. The faucet of claim 11, wherein a light emitting device illuminates the water stream when the faucet is operating in the treatment mode.

13. The faucet of claim 1, further comprising a user interface in communication with the controller, the user interface including a compliance indicator configured to display a representation of a user's compliance with hand hygiene protocols.

14. The faucet of claim 13, wherein the compliance indicator provides a visual pass/fail indication of compliance with hand hygiene protocols.

15. The faucet of claim 1, further comprising a sensor configured to detect the amount of time that a user's hands are in a water stream discharged from the outlet of the spout.

16. The faucet of claim 15, wherein the controller is configured to provide an indication of the amount of time that the water stream is discharged from the outlet, and the amount of time that a user's hands are in the water stream.

17. The faucet of claim 16, wherein data regarding the amount of time that the a user's hands are in the water stream is stored in a remote database.

18. The faucet of claim 17, wherein the remote database is a cloud.

19. The faucet of claim 1, further comprising an identification device for determining the identity of a user.

20. The faucet of claim 19, wherein the identification device is a badge reader.

21. A water treatment dispensing system comprising:
an outer housing defining a chamber;
a first fluid device supported by the outer housing and fluidly coupled to a tap water source for delivering tap water to the hands of a user received within the chamber; and
a second fluid device supported by the outer housing and fluidly coupled to an ozone generator for delivering ozonated water to the hands of a user received within the chamber, wherein the second fluid device comprises a fluidic chip configured to produce a fan of water within a plane by oscillating water about a center axis.

22. The water treatment dispensing system of claim 21, further comprising a gas mitigation system configured to draw ozone outgas from within the chamber, the gas mitigation system including a fan and a carbon filter operably coupled to the fan.

23. The water treatment dispensing system of claim 21, further comprising a user detector configured to activate water flow upon detecting the hands of a user within the chamber.

24. The water treatment dispensing system of claim 23, wherein the user detector comprises an electrode supported by the outer housing, and a capacitive sensor operably coupled to the electrode.

25. The water treatment dispensing system of claim 21, further comprising:
at least one valve in fluid communication with the first fluid device and the second fluid device;
a controller in communication with the at least one valve;
a user interface in communication with the controller, the user interface including a compliance indicator configured to display a representation of a user's compliance with hand hygiene protocols.

26. The water treatment dispensing system of claim 21, wherein the fluidic chip is configured to produce a plurality of fans of water within diverging planes, the water oscillating within each of the planes about a center axis.

27. A water treatment dispensing system comprising:
an outer housing defining a chamber;
a plurality of fluid devices supported by the outer housing;
an ozone generator fluidly coupled to the fluid devices for delivering ozonated water to the hands of a user received within the chamber;
an electrically operable valve in fluid communication with the ozone generator for controlling fluid flow therethrough;
a controller in electrical communication with the electrically operable valve;
a user detector in electrical communication with the controller, wherein the controller controls the electrically operably valve in response to the user detector detecting the hands of a user within the chamber; and
a gas mitigation system in electrical communication with the controller and including a fan configured to draw ozone outgas from within the chamber.

28. The water treatment dispensing system of claim 27, wherein the fluid devices comprise at least one fluidic chip configured to produce a fan of water within a plane by oscillating water about a center axis.

29. The water treatment dispensing system of claim 28, wherein the fluid devices comprise at least one laminar flow device fluidly coupled to a tap water source for delivering tap water to the hands of a user received within the chamber.

30. The water treatment dispensing system of claim 27, wherein the gas mitigation system includes a carbon filter operably coupled to the fan and configured to treat the ozone outgas.

31. The water treatment dispensing system of claim 27, wherein the user detector comprises an electrode supported by the outer housing, and a capacitive sensor operably coupled to the electrode.

32. The water treatment dispensing system of claim 27, further comprising a user interface in communication with the controller, the user interface including a compliance indicator configured to display a representation of a user's compliance with hand hygiene protocols.

* * * * *